US007217549B2

(12) United States Patent
Gilbert et al.

(10) Patent No.: US 7,217,549 B2
(45) Date of Patent: May 15, 2007

(54) β 1,3-GALACTOSYLTRANSFERASES FROM C. JEJUNI

(75) Inventors: Michel Gilbert, Hull (CA); Warren W. Wakarchuk, Gloucester (CA)

(73) Assignee: National Research Council of Cananda, Ottawa (CA)

( * ) Notice: Subject to any disclaimer, the term of this patent is extended or adjusted under 35 U.S.C. 154(b) by 216 days.

(21) Appl. No.: 10/850,807

(22) Filed: May 21, 2004

(65) Prior Publication Data
US 2004/0259140 A1  Dec. 23, 2004

Related U.S. Application Data

(60) Continuation of application No. 10/303,134, filed on Nov. 21, 2002, now Pat. No. 6,825,019, which is a division of application No. 09/816,028, filed on Mar. 21, 2001, now Pat. No. 6,699,705, which is a continuation-in-part of application No. 09/495,406, filed on Jan. 31, 2000, now Pat. No. 6,503,744.

(60) Provisional application No. 60/118,213, filed on Feb. 1, 1999.

(51) Int. Cl.
*C12N 9/10* (2006.01)
*C12N 1/20* (2006.01)
*C07H 21/04* (2006.01)

(52) U.S. Cl. .................. 435/193; 435/69.7; 435/252.3; 536/23.2

(58) Field of Classification Search ...................... None
See application file for complete search history.

(56) References Cited

U.S. PATENT DOCUMENTS

| 5,352,670 A | 10/1994 | Venot et al. |
| 5,374,541 A | 12/1994 | Wong et al. |
| 5,545,553 A | 8/1996 | Gotschlich |

FOREIGN PATENT DOCUMENTS

| WO | WO 92/16640 | 10/1992 |
| WO | WO 96/32491 | 10/1996 |
| WO | WO 99/49051 A1 | 9/1999 |
| WO | WO 00/46379 A1 | 8/2000 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Goodyear et al, Monoclonal antibodies raised against Guillain-Barre syndrome-associated *Campylobacter jejuni* lipopolysaccharides react with neuronal gangliosides and paralyze muscle-nerve preparations. J Clin Invest. Sep. 1999;104(6):697-708. Erratum in: J Clin Invest Dec. 1999;104(12):1771.*

Aspinall et al., "Lipopolysaccharides of *Campylobacter jejuni* Serotype O:19: Structures of Core Oligosaccharide Regions from the Serostrain and Two Bacterial Isolates from Patients with the Guillain-Barré Syndrome" Biochemistry, 33: 241-249 (1994b).
Aspinall et al., "Lipopolysaccharides of *Campylobacter jejuni* Serotype O:19: Antigen Chains from the Serostrain and Two Bacterial Isolates from Patients with the Guillain-Barré Syndrome" Biochemistry, 33: 250-255 (1994c).
Aspinall et al. "Chemical Structures of the Core Regions of *Campylobacter jejuni* Serotypes 0:1, 0:4, 0:23, and 0:38 Lipopolysaccharides," European Journal of Biochemistry, vol. 213, No. 3, pp. 1017-1027, (May 1993).
Aspinall, et al. "Lipopolysaccharides from *Campylobacter jejuni* Associated with Guillain-Barré Syndrome Patients Mimic Human Gangliosides in Structure," Infection and Immunity, vol. 62, No. 5, pp. 2122-2125, (May 1994).
Belunis et al., "Biosynthesis of Endotoxin" J. Biol. Chem., 267:9988-9997 (1992).
Gaudino et al., "A Novel and Efficient Synthesis of Neolacto Series Gangliosides 3'-nLM1 and 6'-nLM1" J. Am. Chem. Soc., 116:1149-1150 (1994).
Gilbert et al., "Cloning of the Lipooligosaccharide α-2,3-Sialyltransferase from the Bacterial Pathogens Neisseria Meningitidis and Neisseria Gonorrhoeae", Journal of Biological Chemistry, vol. 271, No. 45, pp. 28271-28276, The American Society for Biochemistry and Molecular Biology, Inc., USA, (Nov. 8, 1996).
Gilbert, et al., "Biosynthesis of Ganglioside Mimics In *Campylobacter jejuni* OH4384," The Journal of Biolofical Chemistry, vol. 275, No. 6, pp. 3896-3906, The American Society for Biochemistry and Molecular Biology, Inc., USA, (Feb. 11, 2000).
Ito et al., "Synthesis of Bioactive Sialosides" Pure Appl. Chem., 65: 753 (1993).
Kuroki, "*Campylobacter jejuni* Strains from Patients with Guillain-Barré Syndrome Belong Mostly to Penner Serogroup 19 Contain β-N-Acetylglucosamine Residues" Ann. Neurol., 33: 243-247 (1993).
Parkhill, et al. "The Genome Sequence of the Food-Borne Pathogen *Campylobacter jejuni* Reveals Hypervariable Sequences," Nature, vol. 403, pp. 665-668, (Feb. 10, 2000).
Penner, et al., "Diversity of Lipopolysaccharide Structures in *Campylobacter jejuni*," The Journal of Infectious Diseases, vol. 176, No. 2, pp. S135-S138, (Dec. 1997).

(Continued)

*Primary Examiner*—Sheridan Swope
(74) *Attorney, Agent, or Firm*—Townsend and Townsend and Crew, LLP

(57) ABSTRACT

This invention provides prokaryotic glycosyltransferases, including a bifunctional sialyltransferase that has both an α2,3- and an α2,8-activity. A β1,4-GalNAc transferase and a β1,3-galactosyltransferase are also provided by the invention, as are other glycosyltransferases and enzymes involved in synthesis of lipooligosaccharide (LOS). The glycosyltransferases can be obtained from, for example, *Campylobacter* species, including *C. jejuni*. In additional embodiments, the invention provides nucleic acids that encode the glycosyltransferases, as well as expression vectors and host cells for expressing the glycosyltransferases.

6 Claims, 4 Drawing Sheets

OTHER PUBLICATIONS

Prendergast, et al., "Lipopolysaccharides form *Campylobacter jejuni* O:41 Strains Associated with Guillain-Barré Syndrome Exhibit Mimicry of GM1 Ganglioside," Infection and Immunity, vol. 66, No. 6, pp. 3649-3677, (Aug. 1998).

Preston, et al., "The Lipooligosaccharides of Pathogenic Gram-Negative Bacteria," Critical Reviews in Microbiology, vol. 22. No. 3, pp. 139-180, (1996).

Sabesan et al., "Combined Chemical and Enzymatic Synthesis of Sialyloligosaccharides and Characterization by 500-MHz 1H and C NMR Spectroscopy" J. Am. Chem. Soc., 108: 2068-2080 (1988).

Salloway, et al., "Miller-Fisher Syndrome Associated with *Campylobacter jejuni* Bearing Lipopolysaccharide Molecules that Mimic Human Ganglioside GD3," Infection and Immunity, vol. 64, No. 8, pp. 2945-2949, (Aug. 1996).

Wakarchuk et al., "Functional Relationships of the Genetic Locus Encoding the Glycosyltransferase Enzymes Involved in Expression of the Lacto-N-neotetraose Terminal Lipopolysaccharide Structure In Neisseria meningitidis" J. Biol. Chem., 271: 19166-19173 (1996).

Wood, et al., "Cloning, Mutation and Distribution of a Putative Lipopolysaccharide Biosynthesis Locus in *Campylobacter jejuni*," Microbiology, vol. 145, No. 2, pp. 379-388, (Feb. 1999).

Ausubel, et al., "Protein Expression In: Current Protocols in Molecular Biology," Wiley and Sons, Inc., 1987 Chapter 16.

Tomb, et al., The complete genome sequence of the gastric pathogen *Helicobacter pylori*. Swiss-Prot Acc#A64547. Alignment with SEQ ID NO:17.

\* cited by examiner

Figure 1

A   O:19 serostrain

Neu5Ac-α-2,3-Gal-β-1,3-GalNAc-β-1,4-Gal-β-1,3-Hep-
                                           3
                                           |
                                           2
                                         Neu5Acα

B   O:19 strain OH4384

Neu5Ac-α-2,3-Gal-β-1,3-GalNAc-β-1,4-Gal-β-1,3-Hep-
       8                                   3
       |                                   |
       2                                   2
     Neu5Acα                             Neu5Acα

C   O:19 strain OH4382

Neu5Ac-α-2,8-Neu5Ac-α-2,3-Gal-β-1,3-Hep-

Figure 3

```
OH4384    ---------------MKKVIIAGNGPSLKEIDYSRLPNDFDVFRCNQFYFEDKYYLGKKC
O:19      ---------------MKKVIIAGNGPSLKEIDYSRLPNDFDVFRCNQFYFEDKYYLGKKC
Cst-I     MTRTRMENELIVSKNMQNIIIAGNGPSLKNINYKRLPREYDVFRCNQFYFEDKYYLGKKI
11168     ------------MSMNINALVCGNGPSLKNIDYKRLPKQFDVFRCNQFYFEDRYFVGKDV
Hi_ORF    ------------------------------------------------------------
                         ^^^^^^^ ^ ^ ^^^   ^^^^^^^^^^^^^  ^  ^^

OH4384    KAVFYNPILFFEQYYTLKHLIQNQEYETELIMCSNYNQAHLENENFVKTFYDYFPDAHLG
O:19      KAVFYTPNFFFEQYYTLKHLIQNQEYETELIMCSNYNQAHLENENFVKTFYDYFPDAHLG
Cst-I     KAVFFNPGVFLQQYHTAKQLILKNEYEIKNIFCSTFNLPFIESNDFLHQFYNFFPDAKLG
11168     KYVFFNPFVFFEQYYTSKKLIQNEEYNIENIVCSTINLEYIDGFQFVDNFELYFSDAFLG
Hi_ORF    ----------------MQLIKNNEYEYADIILSSFVNLGDSELKKIKNVQKLLTQVDIG
          ^ ^^    ^  ^    ^^ ^ ^  **  ^  **^    *  ^*   ^    ^  ^ ^^ ^*

OH4384    YDFFKQLKDFNAYFKFHEIYFNQRITSGVYMCAVAIALGYKEIYLSGIDFYQN-GSSYAF
O:19      YDFFKQLKEFNAYFKFHEIYFNQRITSGVYMCAVAIALGYKEIYLSGIDFYQN-GSSYAF
Cst-I     YEVIENLKEFYAYIKYNEIYFNKRITSGVYMCAIAIALGYKTIYLCGIDFYEG-DVIYPF
11168     HEIIKKLKDFFAYIKYNEIYNRQRITSGVYMCATAVALGYKSIYISGIDFYQDTNNLYAF
Hi_ORF    HYYLNKLPAFDAYLQYNELYENKRITSGVYMCAVATVMGYKDLYLTGIDFYQEKGNPYAF
          *^  * ** ^  *^* ^ ********** *  ^  *** ^*^ *****^    *^*

OH4384    DTKQKNLLKLAPNFKNDNSHYIGHSKNTDIKALEFLEKTYKIKLYCLCPNSLLANFIELA
O:19      DTKQENLLKLAPDFKNDRSHYIGHSKNTDIKALEFLEKTYKIKLYCLCPNSLLANFIELA
Cst-I     EAMSTNIKTIFPGIK-DFKPSNCHSKEYDIEALKLLKSIYKVNIYALCDDSILANHFPLS
11168     DNNKKNLLNKCTGFKNQKFKFINHSMACDLQALDYLMKRYDVNIYSLNSD----EYFKLA
Hi_ORF    HHQKENIIKLLPSFSQNKSQSDIHSMEYDLNALYFLQKHYGVNIYCISPESPLCNYFPLS
              *     ^   ^^      **     *   **     *       ^ ^    ^  *

OH4384    PNLN-SNFIIQEK-NNYTKDILIPSSEAYGKFSKN---------INFKKIK-IKENIYYK
O:19      PNLN-SNFIIQEK-NNYTKDILIPSSEAYGKFSKN---------INFKKIK-IKENVYYK
Cst-I     ININ-NNFTLENKHNNSINDILLTDNTPGVSFYKNQLKADNKIMLNFYNILHSKDNLIKF
11168     PDIG-SDFVLSKKPKKYINDILIPDKYAQERYYGK-----------KSR-LKENLHYK
Hi_ORF    PLNNPITFILEEK-KNYTQDILIPPKFVYKKIGIYS-----------KPR-IYQNLIFR
          ^  ^    *      ^^  ***^^                    ^      ^   *

OH4384    LIKDLLRLPSDIKHYFKGK------    291
O:19      LIKDLLRLPSDIKHYFKGK------    291
Cst-I     LNKEIAVLKKQTTQRAKARIQNHLS    322
11168     LIKDLIRLPSDIKHYLKEKYANKNR    294
Hi_ORF    LIWDILRLPNDIKHALKSRKWD---    231
          *^^^    *^^ ^^^^    *
```

β 1,3-GALACTOSYLTRANSFERASES FROM C. JEJUNI

CROSS-REFERENCE TO RELATED APPLICATIONS

This application is a continuation application of U.S. patent application Ser. No. 10/303,134, filed Nov. 21, 2002, now U.S. Pat. No. 6,825,019, which is a divisional application of U.S. patent application Ser. No. 09/816,028, filed Mar. 21, 2001, now U.S. Pat. No. 6,699,705; which is a continuation-in-part of U.S. application Ser. No. 09/495,406, filed Jan. 31, 2000, now U.S. Pat. No. 6,503,744; which claims benefit of US Provisional Application No. 60/118,213, which was filed on Feb. 1, 1999 all four applications are incorporated herein by reference for all purposes.

BACKGROUND OF THE INVENTION

1. Field of the Invention

This invention pertains to the field of enzymatic synthesis of oligosaccharides, including gangliosides and ganglioside mimics.

2. Background

Gangliosides are a class of glycolipids, often found in cell membranes, that consist of three elements. One or more sialic acid residues are attached to an oligosaccharide or carbohydrate core moiety, which in turn is attached to a hydrophobic lipid (ceramide) structure which generally is embedded in the cell membrane. The ceramide moiety includes a long chain base (LCB) portion and a fatty acid (FA) portion. Gangliosides, as well as other glycolipids and their structures in general, are discussed in, for example, Lehninger, *Biochemistry* (Worth Publishers, 1981) pp. 287–295 and Devlin, *Textbook of Biochemistry* (Wiley-Liss, 1992). Gangliosides are classified according to the number of monosaccharides in the carbohydrate moiety, as well as the number and location of sialic acid groups present in the carbohydrate moiety. Monosialogangliosides are given the designation "GM", disialogangliosides are designated "GD", trisialogangliosides "GT", and tetrasialogangliosides are designated "GQ". Gangliosides can be classified further depending on the position or positions of the sialic acid residue or residues bound. Further classification is based on the number of saccharides present in the oligosaccharide core, with the subscript "1" designating a ganglioside that has four saccharide residues (Gal-GalNAc-Gal-Glc-Ceramide), disaccharide (Gal-Glc-Ceramide) and monosaccharide (Gal-Ceramide) gangliosides, respectively.

Gangliosides are most abundant in the brain, particularly in nerve endings. They are believed to be present at receptor sites for neurotransmitters, including acetylcholine, and can also act as specific receptors for other biological macromolecules, including interferon, hormones, viruses, bacterial toxins, and the like. Gangliosides are have been used for treatment of nervous system disorders, including cerebral ischemic strokes. See, e.g., Mahadnik et al. (1988) *Drug Development Res.* 15: 337–360; U.S. Pat. Nos. 4,710,490 and 4,347,244; Horowitz (1988) *Adv. Exp. Med. and Biol.* 174: 593–600; Karpiatz et al. (1984) *Adv. Exp. Med. and Biol.* 174: 489–497. Certain gangliosides are found on the surface of human hematopoietic cells (Hildebrand et al. (1972) *Biochim. Biophys. Acta* 260: 272–278; Macher et al. (1981) *J. Biol. Chem.* 256: 1968–1974, Dacremont et al. *Biochim. Biophys. Acta* 424: 315–322; Klock et al. (1981) *Blood Cells* 7: 247) which may play a role in the terminal granulocytic differentiation of these cells. Nojiri et al. (1988) *J. Biol. Chem.* 263: 7443–7446. These gangliosides, referred to as the "neolacto" series, have neutral core oligosaccharide structures having the formula $[Gal\beta\text{-}(1,4)GlcNAc\beta(1,3)]_n$ $Gal\beta(1,4)Glc$, where n=1–4. Included among these neolacto series gangliosides are 3'-nLM$_1$ (NeuAc$\alpha(2,3)$Gal$\beta(1,4)$ GlcNAc$\beta(1,3)$Gal$\beta(1,4)$-Glc$\beta(1,1)$-Cerarmide) and 6'-nLM$_1$ (NeuAc$\alpha(2,6)$Gal$\beta(1,4)$GlcNAc$\beta(1,3)$Gal$\beta(1,4)$-Glc$\beta(1,1)$-Cerarmide).

Ganglioside "mimics" are associated with some pathogenic organisms. For example, the core oligosaccharides of low-molecular-weight LPS of *Campylobacter jejuni* O:19 strains were shown to exhibit molecular mimicry of gangliosides. Since the late 1970s, *Campylobacter jejuni* has been recognized as an important cause of acute gastroenteritis in humans (Skirrow (1977) *Brit. Med. J.* 2: 9–11). Epidemiological studies have shown that *Campylobacter* infections are more common in developed countries than *Salmonella* infections and they are also an important cause of diarrheal diseases in developing countries (Nachamkin et al. (1992) *Campylobacter jejuni: Current Status and Future Trends*. American Society for Microbiology, Washington, D.C.). In addition to causing acute gastroenteritis, *C. jejuni* infection has been implicated as a frequent antecedent to the development of Guillain-Barré syndrome, a form of neuropathy that is the most common cause of generalyzed paralysis (Ropper (1992) *N. Engl. J. Med.* 326: 1130–1136). The most common *C. jejuni* serotype associated with Guillain-Barré syndrome is O:19 (Kuroki (1993) *Ann. Neurol.* 33: 243–247) and this prompted detailed study of the lipopolysaccharide (LPS) structure of strains belonging to this serotype (Aspinall et al. (1994a) *Infect. Immun.* 62: 2122–2125; Aspinall et al. (1994b) *Biochemistry* 33: 241–249; and Aspinall et al. (1994c) *Biochemistry* 33: 250–255).

Terminal oligosaccharide moieties identical to those of GD1a, GD3, GM1 and GT1a gangliosides have been found in various *C. jejuni* O:19 strains. *C. jejuni* OH4384 belongs to serotype O:19 and was isolated from a patient who developed the Guillain-Barre syndrome following a bout of diarrhea (Aspinall et al. (1994a), supra.). It was showed to possess an outer core LPS that mimics the tri-sialylated ganglioside GT1a. Molecular mimicry of host structures by the saccharide portion of LPS is considered to be a virulence factor of various mucosal pathogens which would use this strategy to evade the immune response (Moran et al. (1996a) *FEMS Immunol. Med. Microbiol.* 16: 105–115; Moran et al. (1996b) *J. Endotoxin Res.* 3: 521–531).

Consequently, the identification of the genes involved in LPS synthesis and the study of their regulation is of considerable interest for a better understanding of the pathogenesis mechanisms used by these bacteria. Moreover, the use of gangliosides as therapeutic reagents, as well as the study of ganglioside function, would be facilitated by convenient and efficient methods of synthesizing desired gangliosides and ganglioside mimics. A combined enzymatic and chemical approach to synthesis of 3'-nLM$_1$ and 6'-nLM$_1$ has been described (Gaudino and Paulson (1994) *J. Am. Chem. Soc.* 116: 1149–1150). However, previously available enzymatic methods for ganglioside synthesis suffer from difficulties in efficiently producing enzymes in sufficient quantities, at a sufficiently low cost, for practical large-scale ganglioside synthesis. Thus, a need exists for new enzymes involved in ganglioside synthesis that are amenable to large-scale production. A need also exists for more efficient methods for synthesizing gangliosides. The present invention fulfills these and other needs.

BRIEF DESCRIPTION OF THE DRAWINGS

FIGS. 1A–1C show lipooligosaccharide (LOS) outer core structures from *C. jejuni* O:19 strains. These structures were described by Aspinall et al. (1994) *Biochemistry* 33, 241–249, and the portions showing similarity with the oligosaccharide portion of gangliosides are delimited by boxes. FIG. 1A: LOS of *C. jejuni* O:19 serostrain (ATCC #43446) has structural similarity to the oligosaccharide portion of ganglioside GD1a. FIG. 1B: LOS of *C. jejuni* O:19 strain OH4384 has structural similarity to the oligosaccharide portion of ganglioside GT1a. FIG. 1C: LOS of *C. jejuni* OH4382 has structural similarity to the oligosaccharide portion of ganglioside GD3.

FIG. 2A shows a schematic representation of the OH4384 cst-I locus, based on the nucleotide sequence which is available from GenBank (#AF130466). The partial prfB gene is somewhat similar to a peptide chain release factor (GenBank #AE000537) from *Helicobacter pylori*, while the cysD gene and the partial cysN gene are similar to *E. coli* genes encoding sulfate adenylyltransferase subunits (GenBank #AE000358). FIG. 2B shows a schematic representation of the OH4384 LOS biosynthesis locus, which is based on the nucleotide sequence from GenBank (#AF130984). The nucleotide sequence of the OH4382 LOS biosynthesis locus is identical to that of OH4384 except for the cgtA gene, which is missing an "A" (see text and GenBank #AF167345). The sequence of the NCTC 11168 LOS biosynthesis locus is available from the Sanger Centre. Corresponding homologous genes have the same number with a trailing "a" for the OH4384 genes and a trailing "b" for the NCTC 11168 genes. A gene unique to the OH4384 strain is shown in black and genes unique to NCTC 11168 are shown in grey. The OH4384 ORF's #5a and #10a are found as an in-frame fusion ORF (#5b/10b) in NCTC 11168 and are denoted with an asterisk (*). Proposed functions for each ORF are found in Table 4.

FIG. 3 shows an alignment of the deduced amino acid sequences for the sialyltransferases. The OH4384 cst-I gene (SEQ ID NO:48, first 300 residues), OH4384 cst-II gene (SEQ ID NO:3, identical to OH4382 cst-II), O:19 (serostrain) cst-II gene (SEQ ID NO:9, GenBank #AF167344), NCTC 11168 cst-II gene (SEQ ID NO: 10) and an *H. influenzae* putative ORF (SEQ ID NO:49, GenBank #U32720) were aligned using the ClustalX alignment program (Thompson et at. (1997) *Nucleic Acids Res.* 25, 4876–82). The shading was produced by the program Gene-Doc (Nicholas, K. B., and Nicholas, H. B. (1997).

SUMMARY OF THE INVENTION

Figure 2:
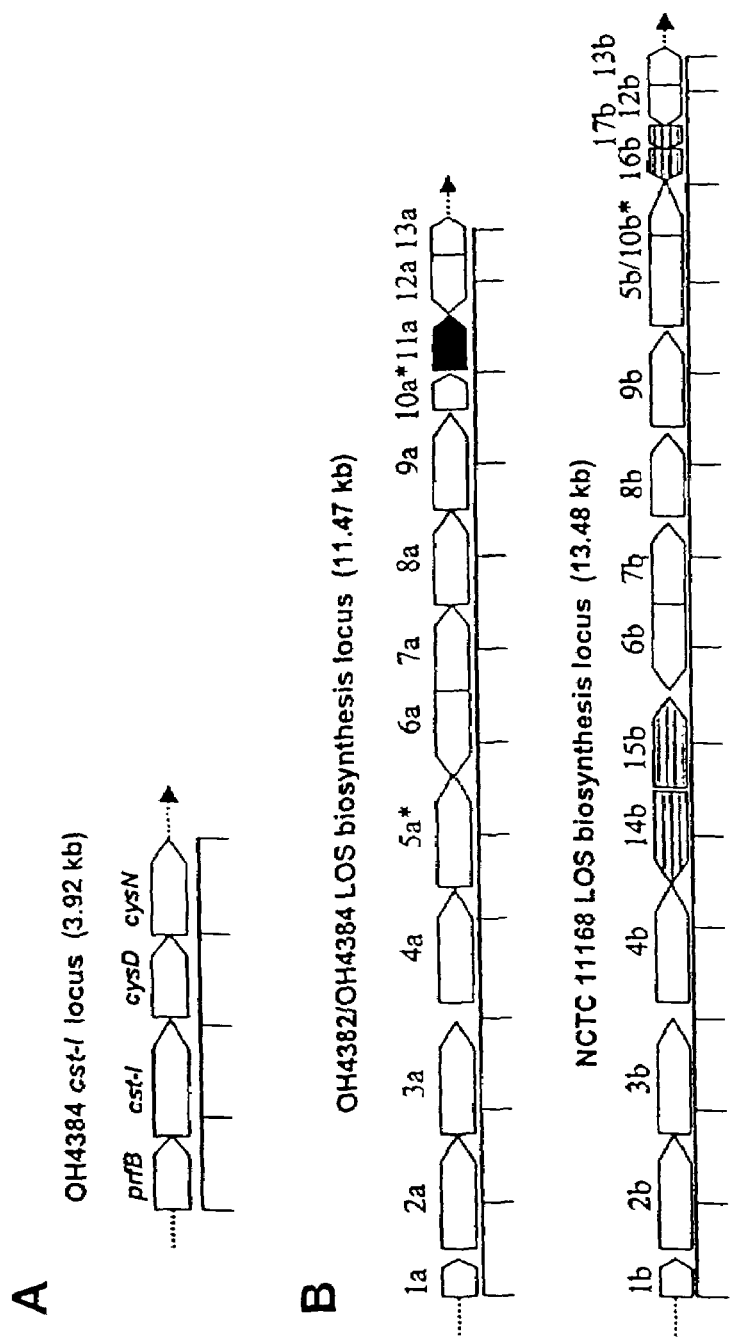
FIGS. 2A–2B show the genetic organization of the cst-I locus from OH4384 and comparison of the LOS biosynthesis loci from OH4384 and NCTC 11168. The distance between the scale marks is 1 kb.

The present invention provides prokaryotic glycosyltransferase enzymes and nucleic acids that encode the enzymes. In one embodiment, the invention provides isolated and/or recombinant nucleic acid molecules that include a polynucleotide sequence that encodes a polypeptide selected from the group consisting of:

a) a polypeptide having lipid A biosynthesis acyltransferase activity, wherein the polypeptide comprises an amino acid sequence that is at least about 70% identical to an amino acid sequence encoded by nucleotides 350–1234 (ORF 2a) of the LOS biosynthesis locus of *C. jejuni* strain OH4384 as shown in SEQ ID NO:1;

b) a polypeptide having glycosyltransferase activity, wherein the polypeptide comprises an amino acid sequence that is at least about 70% identical to an amino acid sequence encoded by nucleotides 1234–2487 (ORF 3a) of the LOS biosynthesis locus of *C. jejuni* strain OH4384 as shown in SEQ ID NO:1;

c) a polypeptide having glycosyltransferase activity, wherein the polypeptide comprises an amino acid sequence that is at least about 50% identical to an amino acid sequence encoded by nucleotides 2786–3952 (ORF 4a) of the LOS biosynthesis locus of *C. jejuni* strain OH4384 as shown in SEQ ID NO:1 over a region at least about 100 amino acids in length;

d) a polypeptide having β1,4-GalNAc transferase activity, wherein the GalNAc transferase polypeptide has an amino acid sequence that is at least about 77% identical to an amino acid sequence as set forth in SEQ ID NO:17 over a region at least about 50 amino acids in length;

e) a polypeptide having β1,3-galactosyltransferase activity, wherein the galactosyltransferase polypeptide has an amino acid sequence that is at least about 75% identical to an amino acid sequence as set forth in SEQ ID NO:27 or SEQ ID NO:29 over a region at least about 50 amino acids in length;

f) a polypeptide having either α2,3 sialyltransferase activity or both α2,3- and α2,8 sialyltransferase activity, wherein the polypeptide has an amino acid sequence that is at least about 66% identical over a region at least about 60 amino acids in length to an amino acid sequence as set forth in one or more of SEQ ID NO:3, SEQ ID NO:5, SEQ ID NO:7 or SEQ ID NO:10;

g) a polypeptide having sialic acid synthase activity, wherein the polypeptide comprises an amino acid sequence that is at least about 70% identical to an amino acid sequence encoded by nucleotides 6924–7961 of the LOS biosynthesis locus of *C. jejuni* strain OH4384 as shown in SEQ ID NO:1;

h) a polypeptide having sialic acid biosynthesis activity, wherein the polypeptide comprises an amino acid sequence that is at least about 70% identical to an amino acid sequence encoded by nucleotides 8021–9076 of the LOS biosynthesis locus of *C. jejuni* strain OH4384 as shown in SEQ ID NO:1;

i) a polypeptide having CMP-sialic acid synthetase activity, wherein the polypeptide comprises an amino acid sequence that is at least about 65% identical to an amino acid sequence encoded by nucleotides 9076–9738 of the LOS biosynthesis locus of *C. jejuni* strain OH4384 as shown in SEQ ID NO:1;

j) a polypeptide having acetyltransferase activity, wherein the polypeptide comprises an amino acid sequence that is at least about 65% identical to an amino acid sequence-encoded by nucleotides 9729–10559 of the LOS biosynthesis locus of *C. jejuni* strain OH4384 as shown in SEQ ID NO:1; and k) a polypeptide having glycosyltransferase activity, wherein the polypeptide comprises an amino acid sequence that is at least about 65% identical to an amino acid sequence encoded by a reverse complement of nucleotides 10557–11366 of the LOS biosynthesis locus of *C. jejuni* strain OH4384 as shown in SEQ ID NO:1.

In presently preferred embodiments, the invention provides an isolated nucleic acid molecule that includes a polynucleotide sequence that encodes one or more polypeptides selected from the group consisting of: a) a sialyltransferase polypeptide that has both an α2,3 sialyltransferase activity and an α2,8 sialyltransferase activity, wherein the sialyltransferase polypeptide has an amino acid sequence that is at least about 76% identical to an amino acid sequence as set forth in SEQ ID NO:3 over a region at least about 60 amino acids in length; b) a GalNAc transferase polypeptide that has a β1,4-GalNAc transferase activity, wherein the GalNAc transferase polypeptide has an amino acid sequence that is at least about 75% identical to an amino acid sequence as set forth in SEQ ID NO:17 over a region at least about 50 amino acids in length; and c) a galactosyltransferase polypeptide that has β1,3-galactosyltransferase activity, wherein the galactosyltransferase polypeptide has an amino acid sequence that is at least about 75% identical to an amino acid sequence as set forth in SEQ ID NO:27 over a region at least about 50 amino acids in length.

Also provided by the invention are expression cassettes and expression vectors in which a glycosyltransferase nucleic acid of the invention is operably linked to a promoter and other control sequences that facilitate expression of the glycosyltransferases in a desired host cell. Recombinant host cells that express the glycosyltransferases of the invention are also provided.

The invention also provides isolated and/or recombinantly produced polypeptides selected from the group consisting of:

a) a polypeptide having lipid A biosynthesis acyltransferase activity, wherein the polypeptide comprises an amino acid sequence that is at least about 70% identical to an amino acid sequence encoded by nucleotides 350–1234 (ORF 2a) of the LOS biosynthesis locus of *C. jejuni* strain OH4384 as shown in SEQ ID NO:1;

b) a polypeptide having glycosyltransferase activity, wherein the polypeptide comprises an amino acid sequence that is at least about 70% identical to an amino acid sequence encoded by nucleotides 1234–2487 (ORF 3a) of the LOS biosynthesis locus of *C. jejuni* strain OH4384 as shown in SEQ ID NO:1;

c) a polypeptide having glycosyltransferase activity, wherein the polypeptide comprises an amino acid sequence that is at least about 50% identical to an amino acid sequence encoded by nucleotides 2786–3952 (ORF 4a) of the LOS biosynthesis locus of *C. jejuni* strain OH4384 as shown in SEQ ID NO:1 over a region at least about 100 amino acids in length;

d) a polypeptide having β1,4-GalNAc transferase activity, wherein the GalNAc transferase polypeptide has an amino acid sequence that is at least about 77% identical to an amino acid sequence as set forth in SEQ ID NO:17 over a region at least about 50 amino acids in length;

e) a polypeptide having β1,3-galactosyltransferase activity, wherein the galactosyltransferase polypeptide has an amino acid sequence that is at least about 75% identical to an amino acid sequence as set forth in SEQ ID NO:27 or SEQ ID NO:29 over a region at least about 50 amino acids in length;

f) a polypeptide having either α2,3 sialyltransferase activity or both α2,3 and α2,8 sialyltransferase activity, wherein the polypeptide has an amino acid sequence that is at least about 66% identical to an amino acid sequence as set forth in SEQ ID NO:3, SEQ ID NO:5, SEQ ID NO:7 or SEQ ID NO:10 over a region at least about 60 amino acids in length;

g) a polypeptide having sialic acid synthase activity, wherein the polypeptide comprises an amino acid sequence that is at least about 70% identical to an amino acid sequence encoded by nucleotides 6924–7961 of the LOS biosynthesis locus of *C. jejuni* strain OH4384 as shown in SEQ ID NO:1;

h) a polypeptide having sialic acid biosynthesis activity, wherein the polypeptide comprises an amino acid sequence that is at least about 70% identical to an amino acid sequence encoded by nucleotides 8021–9076 of the LOS biosynthesis locus of *C. jejuni* strain OH4384 as shown in SEQ ID NO:1;

i) a polypeptide having CMP-sialic acid synthetase activity, wherein the polypeptide comprises an amino acid sequence that is at least about 65% identical to an amino acid sequence encoded by nucleotides 9076–9738 of the LOS biosynthesis locus of *C. jejuni* strain OH4384 as shown in SEQ ID NO:1;

j) a polypeptide having acetyltransferase activity, wherein the polypeptide comprises an amino acid sequence that is at least about 65% identical to an amino acid sequence encoded by nucleotides 9729–10559 of the LOS biosynthesis locus of *C. jejuni* strain OH4384 as shown in SEQ ID NO:1; and k) a polypeptide having glycosyltransferase activity, wherein the polypeptide comprises an amino acid sequence that is at least about 65% identical to an amino acid sequence encoded by a reverse complement of nucleotides 10557–11366 of the LOS biosynthesis locus of *C. jejuni* strain OH4384 as shown in SEQ ID NO:1.

In presently preferred embodiments, the invention provides glycosyltransferase polypeptides including: a) a sialyltransferase pol%peptide that has both an α2,3 sialyltransferase activity and an α2,8 sialyltransferase activity, wherein the sialyltransferase polypeptide has an amino acid sequence that is at least about 76% identical to an amino acid sequence as set forth in SEQ ID NO:3 over a region at about 60 amino acids in length; b) a GalNAc transferase polypeptide that has a β1,4-GalNAc transferase activity, wherein the GalNAc transferase polypeptide has an amino acid sequence that is at least about 75% identical to an amino acid sequence as set forth in SEQ ID NO:17 over a region at least about 50 amino acids in length; and c) a galactosyltransferase polypeptide that has β1,3-galactosyltransferase activity, wherein the galactosyltransferase polypeptide has an amino acid sequence that is at least about 75% identical to an amino acid sequence as set forth in SEQ ID NO:27 or SEQ ID NO:29 over a region at least about 50 amino acids in length.

The invention also provides reaction mixtures for the synthesis of a sialylated oligosaccharide. The reaction mixtures include a sialyltransferase polypeptide which has both an α2,3 sialyltransferase activity and an α2,8 sialyltransferase activity. Also present in the reaction mixtures are a galactosylated acceptor moiety and a sialyl-nucleotide sugar. The sialyltransferase transfers a first sialic acid residue from the sialyl-nucleotide sugar (e.g., CMP-sialic acid) to the galactosylated acceptor moiety in an α2,3 linkage, and further adds a second sialic acid residue to the first sialic acid residue in an α2,8 linkage.

In another embodiment, the invention provides methods for synthesizing a sialylated oligosaccharide. These methods involve incubating a reaction mixture that includes a sialyltransferase polypeptide which has both an α2,3 sialyltransferase activity and an α2,8 sialyltransferase activity, a galactosylated acceptor moiety, and a sialyl-nucleotide sugar, under suitable conditions wherein the sialyltransferase polypeptide transfers a first sialic acid residue from the sialyl-nucleotide sugar to the galactosylated acceptor moiety in an α2,3 linkage, and further transfers a second sialic acid residue to the first sialic acid residue in an α2,8 linkage.

DETAILED DESCRIPTION

Definitions

The glycosyltransferases, reaction mixtures, and methods of the invention are useful for transferring a monosaccharide from a donor substrate to an acceptor molecule. The addition generally takes place at the non-reducing end of an oligosaccharide or carbohydrate moiety on a biomolecule. Biomolecules as defined here include, but are not limited to, biologically significant molecules such as carbohydrates, proteins (e.g., glycoproteins), and lipids (e.g., glycolipids, phospholipids, sphingolipids and gangliosides).

The following abbreviations are used herein:
Ara=arabinosyl;
Fru=fructosyl;
Fuc=fucosyl;
Gal=galactosyl;
GalNAc=N-acetylgalactosaminyl;
Glc=glucosyl;
GlcNAc=N-acetylglucosaminyl;
Man=mannosyl; and
NeuAc=sialyl (N-acetylneuraminyl).

The term "sialic acid" refers to any member of a family of nine-carbon carboxylated sugars. The most common member of the sialic acid family is N-acetyl-neuraminic acid (2-keto-5-acetamindo-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550–11557; Kanamori et al. (1990) *J. Biol. Chem.* 265: 21811–21819. Also included are 9-substituted sialic acids such as a 9-O-$C_1$–$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki (1992) *Glycobiology* 2: 25–40; *Sialic Acids: Chemistry, Metabolism and Function*, R. Schauer, Ed. (Springer-Verlag, New York (1992); Schauer, *Methods in Enzymology*, 50: 64–89 (1987), and Schaur, *Advances in Carbohydrate Chemistry and Biochemistry*, 40: 131–234. The synthesis and use of sialic acid compounds in a sialylation procedure is disclosed in international application WO 92/16640, published Oct. 1, 1992.

Donor substrates for glycosyltransferases are activated nucleotide sugars. Such activated sugars generally consist of uridine and guanosine diphosphates, and cytidine monophosphate derivatives of the sugars in which the nucleoside diphosphate or monophosphate serves as a leaving group. Bacterial, plant, and fungal systems can sometimes use other activated nucleotide sugars.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g:, GlcNAc). The linkage between two sugars may be expressed, for example, as 2,3, 2→3, or (2,3). Each saccharide is a pyranose or furanose.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes, the complementary sequence thereof.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

A "heterologous polynucleotide" or a "heterologous nucleic acid", as used herein, is one that originates from a source foreign to the particular host cell, or, if from the same source, is modified from its original form. Thus, a heterologous glycosyltransferase gene in a host cell includes a glycosyltransferase gene that is endogenous to the particular host cell but has been modified. Modification of the heterologous sequence may occur, e.g., by treating the DNA with a restriction enzyme to generate a DNA fragment that is capable of being operably linked to a promoter. Techniques such as site-directed mutagenesis are also useful for modifying a heterologous sequence.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells also include those that contain genes that are found in the native form of the cell, but are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques known to those of skill in the art.

A "recombinant nucleic acid" is a nucleic acid that is in a form that is altered from its natural state. For example, the term "recombinant nucleic acid" includes a coding region that is operably linked to a promoter and/or other expression control region, processing signal, another coding region, and the like., to which the nucleic acid is not linked in its naturally occurring form. A "recombinant nucleic acid" also includes, for example, a coding region or other nucleic acid in which one or more nucleotides have been substituted, deleted, inserted, compared to the corresponding naturally occurring nucleic acid. The modifications include those introduced by in vitro manipulation, in vivo modification, synthesis methods, and the like.

A "recombinantly produced polypeptide" is a polypeptide that is encoded by a recombinant and/or heterologous nucleic acid. For example, a polypeptide that is expressed from a *C. jejuni* glycosyltrrnsferase-encoding nucleic acid which is introduced into *E. coli* is a "recombinantly produced polypeptide." A protein expressed from a nucleic acid that is operably linked to a non-native promoter is one example of a "recombinantly produced polypeptide. Recombinantly produced polypeptides of the invention can be used to synthesize gangliosides and other oligosaccharides in their unpurified form (e.g., as a cell lysate or an intact cell), or after being completely or partially purified.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "subsequence" refers to a sequence of nucleic acids or amino acids that comprise a part of a longer sequence of nucleic acids or amino acids (e.g., polypeptide) respectively.

The term "isolated" is meant to refer to material that is substantially or essentially free from components which normally accompany the material as found in its native state. Typically, isolated proteins or nucleic acids of the invention are at least about 80% pure, usually at least about 90%, and preferably at least about 95% pure. Purity or homogeneity can be indicated by a number of means well known in the art, such as agarose or polyacrylamide gel electrophoresis of a protein or nucleic acid sample, followed by visualization upon staining. For certain purposes high resolution will be needed and HPLC or a similar means for purification utilized. An "isolated" enzyme, for example, is one which is substantially or essentially free from components which interfere with the activity of the enzyme. An "isolated" nucleic acid" includes, for example, one that is not present in the chromosome of the cell in which the nucleic acid naturally occurs.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et at. (1990) *J. Mol. Biol.* 215: 403–410 and Altschuel et at. (1977) *Nucleic Acids Res.* 25: 3389–3402, respectively. Software for performing BLAST analyses is publicly available through the National Center for Biotechnology Information. For example, the comparisons can be performed using a BLASTN Version 2.0 algorithm with a wordlength (W) of 11, G=5, E=2, q=−2, and r=1., and a comparison of both strands. For amino acid sequences, the BLASTP Version 2.0 algorithm can be used, with the default values of wordlength (W) of 3, G=11, E=1, and a BLOSUM62 substitution matrix. (see Henikoff & Henikoff, *Proc. Nati. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. One of skill will appreciate that many conservative variations of the fusion proteins and nucleic acid which encode the fusion proteins yield essentially identical products. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. As described herein, sequences are preferably optimized for expression in a particular host cell used to produce the enzymes (e.g., yeast, human, and the like). Similarly, "conservative amino acid substitutions," in one or a few amino acids in an amino acid sequence are substituted with different amino acids with highly similar properties (see, the definitions section, supra), are also readily identified as being highly similar to a particular amino acid sequence, or to a particular nucleic acid sequence which encodes an amino acid. Such conservatively substituted variations of any particular sequence arela feature of the present invention. See also, Creighton (1984) *Proteins*, W. H. Freeman and Company. In addition, individual substitutions, deletions or additions which alter, add or delete a single amino acid or a small percentage of amino acids in an encoded sequence are also "conservatively modified variations".

DESCRIPTION OF THE PREFERRED EMBODIMENTS

The present invention provides novel glycosyltransferase enzymes, as well as other enzymes that are involved in enzyme-catalyzed oligosaccharide synthesis. The glycosyltransferases of the invention include sialyltransferases, including a bifunctional sialyltransferase that has both an α2,3 and an α2,8 sialyltransferase activity. Also provided are β1,3-galactosyltransferases, β1,4-GalNAc transferases, sialic acid synthases, CMP-sialic acid synthetases, acetyltransferases, and other glycosyltransferases. The enzymes of the invention are prokaryotic enzymes, include those involved in the biosynthesis of lipooligosaccharides (LOS) in various strains of *Campylobacter jejuni*. The invention also provides nucleic acids that encode these enzymes, as well as expression cassettes and expression vectors for use in expressing the glycosyltransferases. In additional embodiments, the invention provides reaction mixtures and methods in which one or more of the enzymes is used to synthesize an oligosaccharide.

The glycosyltransferases of the invention are useful for several purposes. For example, the glycosyltransferases are useful as tools for the chemo-enzymatic syntheses of oligosaccharides, including gangliosides and other oligosaccharides that have biological activity. The glycosyltransferases of the invention, and nucleic acids that encode the glycosyltransferases, are also useful for studies of the pathogenesis mechanisms of organisms that synthesize ganglioside mimics, such as *C. jejuni*. The nucleic acids can be used as probes, for example, to study expression of the genes involved in ganglioside mimetic synthesis. Antibodies raised against the glycosyltransferases are also useful for analyzing the expression patterns of these genes that are involved in pathogenesis. The nucleic acids are also useful for designing antisense oligonucleotides for inhibiting expression of the *Campylobacter* enzymes that are involved in the biosynthesis of ganglioside mimics that can mask the pathogens from the host's immune system.

The glycosyltransferases of the invention provide several advantages over previously available glycosyltransferases. Bacterial glycosyltransferases such as those of the invention can catalyze the formation of oligosaccharides that are identical to the corresponding mammalian structures. Moreover, bacterial enzymes are easier and less expensive to produce in quantity, compared to mammalian glycosyltransferases. Therefore, bacterial glycosyltransferases such as those of the present invention are attractive replacements for mammalian glycosyltransferases, which can be difficult to obtain in large amounts. That the glycosyltransferases of the invention are of bacterial origin facilitates expression of large quantities of the enzymes using relatively inexpensive prokaryotic expression systems. Typically, prokaryotic systems for expression of polypeptide products involves a much lower cost than expression of the polypeptides in mammalian cell culture systems.

Moreover, the novel bifunctional sialyltransferases of the invention simplify the enzymatic synthesis of biologically important molecules, such as gangliosides, that have a sialic acid attached by an α2,8 linkage to a second sialic acid, which in turn is α2,3-linked to a galactosylated acceptor. While previous methods for synthesizing these structures required two separate sialyltransferases, only one sialyltransferase is required when the bifunctional sialyltransferase of the present invention is used. This avoids the costs associated with obtaining a second enzyme, and can also reduce the number of steps involved in synthesizing these compounds.

A. Glycosyltransferases and Associated Enzymes

The present invention provides prokaryotic glycosyltransferase polypeptides, as well as other enzymes that are involved in the glycosyltransferase-catalyzed synthesis of oligosaccharides, including gangliosides and ganglioside mimics. In presently preferred embodiments, the polypeptides include those that are encoded by open reading frames within the lipooligosaccharide (LOS) locus of *Campylobacter* species (FIG. 1). Included among the enzymes of the invention are glycosyltransferases, such as sialyltransferases (including a bifunctional sialyltransferase), β1,4-GalNAc transferases, and β1,3-galactosyltransferases, among other enzymes as described herein. Also provided are accessory enzymes such as, for example, CMP-sialic acid synthetase, sialic acid synthase, acetyltransferase, an acyltransferase that is involved in lipid A biosynthesis, and an enzyme involved in sialic acid biosynthesis.

The glycosyltransferases and accessory polypeptides of the invention can be purified from natural sources, e.g., prokaryotes such as *Campylobacter* species. In presently preferred embodiments, the glycosyltransferases are obtained from *C. jejuni*, in particular from *C. jejuni* serotype O:19, including the strains OH4384 and OH4382. Also provided are glycosyltransferases and accessory enzymes obtained from *C. jejuni* serotypes O:10, O:41, and O:2. Methods by which the glycosyltransferase polypeptides can be purified include standard protein purification methods including, for example, ammonium sulfate precipitation, affinity columns, column chromatography, gel electrophoresis and the like (see, generally, R. Scopes, *Protein Purification*, Springer-Verlag, N.Y. (1982) Deutscher, *Methods in Enzymology* Vol. 182: *Guide to Protein Purification*., Academic Press, Inc. N.Y. (1990)).

In presently preferred embodiments, the glycosyltransferase and accessory enzyme polypeptides of the invention are obtained by recombinant expression using the glycosyltransferase- and accessory enzyme-encoding nucleic acids described herein. Expression vectors and methods for producing the glycosyltransferases are described in detail below.

In some embodiments, the glycosyltransferase polypeptides are isolated from their natural milieu, whether recombinantly produced or purified from their natural cells. Substantially pure compositions of at least about 90 to 95% homogeneity are preferred for some applications, and 98 to 99% or more homogeneity are most preferred. Once purified, partially or to homogeneity as desired, the polypeptides may then be used (e.g., as immunogens for antibody production or for synthesis of oligosaccharides, or other uses as described herein or apparent to those of skill in the art). The glycosyltransferases need not, however, be even partially purified for use to synthesize a desired saccharide structure. For example, the invention provides recombinantly produced enzymes that are expressed in a heterologous host cell and/or from a recombinant nucleic acid. Such enzymes of the invention can be used when present in a cell lysate or an intact cell, as well as in purified form.

1. Sialyltransferases

Figure 4:
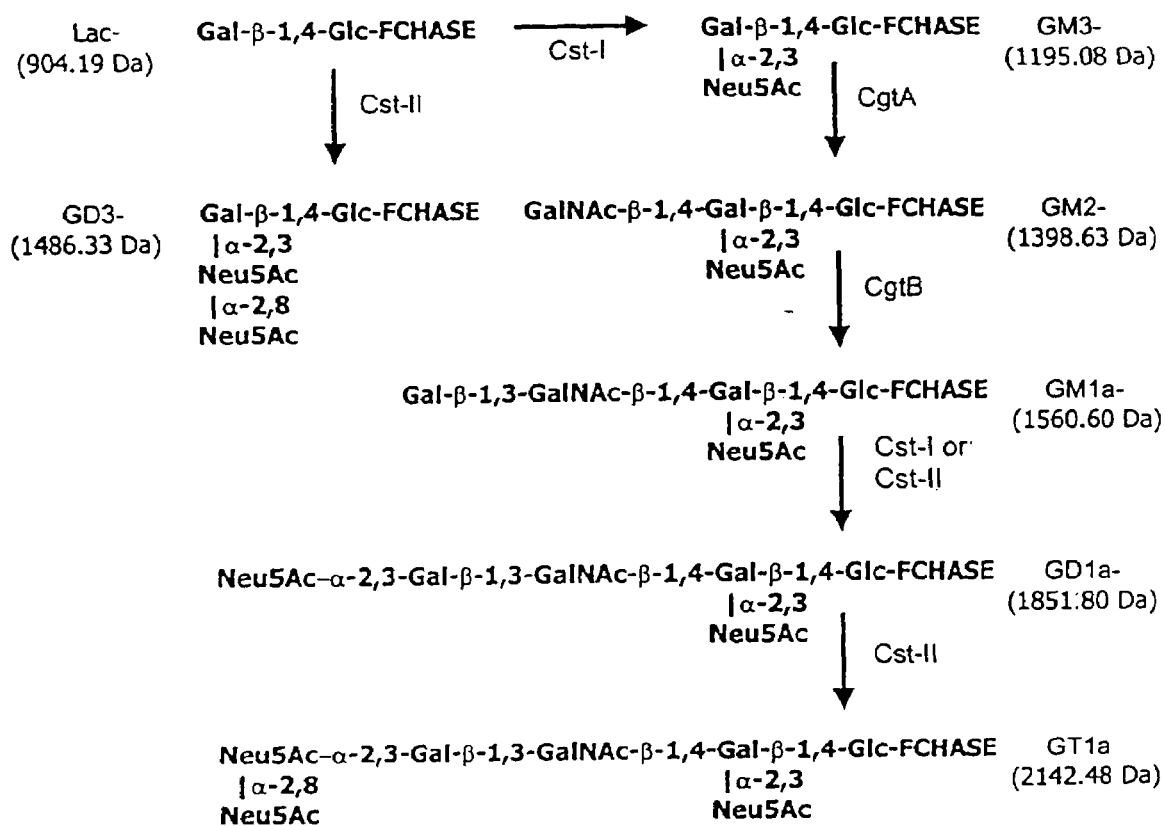
FIG. 4 shows a scheme for the enzymatic synthesis of ganglioside mimics using *C. jejuni* OH4384 glycosyltransferases. Starting from a synthetic acceptor molecule, a series of ganglioside mimics was synthesized with recombinant α-2,3-sialyltransferase-(Cst-I), β-1,4-N-acetylgalactosaminyltransferase (CgtA), β-1,3-galactosyltransferase (CgtB), and a bi-functional α-2,3/α-2,8-sialyltransferase (Cst-II) using the sequences shown. All the products were analyzed by mass spectrometry and the observed monoisotopic masses (shown in parentheses) were all within 0.02% of the theoretical masses. The GM3, GD3, GM2 and GM1a mimics were also analyzed by NMR spectroscopy (see Table 4).

In some embodiments, the invention provides sialyltransferase polypeptides. The sialyltransferases have an α2,3-sialyltransferase activity, and in some cases also have an α2,8 sialyltransferase activity. These bifunctional sialyltransferases, when placed in a reaction mixture with a suitable saccharide acceptor (e.g., a saccharide having a terminal galactose) and a sialic acid donor (e.g., CMP-sialic acid) can catalyze the transfer of a first sialic acid from the donor to the acceptor in an α2,3 linkage. The sialyltransferase then catalyzes the transfer of a second sialic acid from a sialic acid donor to the first sialic acid residue in an α2,8 linkage. This type of Siaα2,8-Siaα2,3-Gal structure is often found in gangliosides, including GD3 and GT1a as shown in FIG. 4.

Examples of bifunctional sialyltransferases of the invention are those that are found in *Campylobacter* species, such as *C. jejuni*. A presently preferred bifunctional sialyltransferase of the invention is that of the *C. jejuni* serotype O:19. One example of a bifunctional sialyltransferase is that of *C. jejuni* strain OH 4384; this sialyltransferase has an amino acid sequence as shown in SEQ ID NO:3. Other bifunctional sialyltransferases of the invention generally have an amino acid sequence that is at least about 76% identical to the amino acid sequence of the *C. jejuni* OH4384 bifunctional sialyltransferase over a region at least about 60 amino acids in length. More preferably, the sialyltransferases of the invention are at least about 85% identical to the OH 4384 sialyltransferase amino acid sequence, and still more preferably at least about 95% identical to the amino acid sequence of SEQ ID NO:3, over a region of at least 60 amino acids in length. In presently preferred embodiments, the region of percent identity extends over a region longer than 60 amino acids. For example, in more preferred embodiments, the region of similarity extends over a region of at least about 100 amino acids in length, more preferably a region of at least about 150 amino acids in length, and most preferably over the full length of the sialyltransferase. Accordingly, the bifunctional sialyltransferases of the invention include polypeptides that have either or both the α2,3- and α2,8-sialyltransferase activity and are at least about 65% identical, more preferably at least about 70% identical, more preferably at least about 80% identical, and most preferably at least about 90% identical to the amino acid sequence of the *C. jejuni* OH 4384 CstII sialyltransferase (SEQ ID NO:3) over a region of the polypeptide that is required to retain the respective sialyltransferase activities. In some embodiments, the bifunctional sialyltransferases of the invention are identical to *C. jejuni* OH 4384 CstII sialyltransferase over the entire length of the sialyltransferase.

The invention also provides sialyltransferases that have α2,3 sialyltransferase activity, but little or no α2,8 sialyltransferase activity. For example, CstII sialyltransferase of the *C. jejuni* O:19 serostrain (SEQ ID NO:9) differs from that of strain OH 4384 by eight amino acids, but nevertheless substantially lacks α2,8 sialyltransferase activity (FIG. 3). The corresponding sialyltransferase from the O:2 serotype strain NCTC 11168 (SEQ ID NO:10) is 52% identical to that of OH4384, and also has little or no α2,8-sialyltransferase activity. Sialyltransferases that are substantially identical to the CstII sialyltransferase of *C. jejuni* strain O:10 (SEQ ID NO:5) and O:41 (SEQ ID NO:7) are also provided. The sialyltransferases of the invention include those that are at least about 65% identical, more preferably at least about 70% identical, more preferably at least about 80% identical, and most preferably at least about 90% identical to the amino acid sequences of the *C. jejuni* O:10 (SEQ ID NO:5), O:41 (SEQ ID NO:7), O:19 serostrain (SEQ ID NO:9), or O:2 serotype strain NCTC 11168 (SEQ ID NO:10). The sialyltransferases of the invention, in some embodiments, have an amino acid sequence that is identical to that of the O:10, O:41, O:19 serostrain or NCTC 11168 *C. jejuni* strains.

The percent identities can be determined by inspection, for example, or can be determined using an alignment algorithm such as the BLASTP Version 2.0 algorithm using the default parameters, such as a wordlength (W) of 3, G=11, E=1, and a BLOSUM62 substitution matrix.

Sialyltransferases of the invention can be identified, not only by sequence comparison, but also by preparing antibodies against the *C. jejuni* OH4384 bifunctional sialyltransferase, or other sialyltransferases provided herein, and determining whether the antibodies are specifically immunoreactive with a sialyltransferase of interest. To obtain a bifunctional sialyltransferase in particular, one can identify an organism that is likely to produce a bifunctional sialyltransferase by determining whether the organism displays both α2,3 and α2,8-sialic acid linkages on its cell surfaces. Alternatively, or in addition, one can simply do enzyme assays of an isolated sialyltransferase to determine whether both sialyltransferase activities are present.

2. β1,4-GalNAc Transferase

The invention also provides β1,4-GalNAc transferase polypeptides (e.g., CgtA). The β1,4-GalNAc transferases of the invention, when placed in a reaction mixture, catalyze the transfer of a GalNAc residue from a donor (e.g., UDP-GalNAc) to a suitable acceptor saccharide (typically a saccharide that has a terminal galactose residue). The resulting structure, GalNAcβ1,4-Gal-, is often found in gangliosides and other sphingoids, among many other saccharide compounds. For example, the CgtA transferase can catalyze the conversion of the ganglioside GM3 to GM2 (FIG. 4).

Examples of the β1,4-GalNAc transferases of the invention are those that are produced by *Campylobacter* species, such as *C. jejuni*. One example of a β1,4-GalNAc transferase polypeptide is that of *C. jejuni* strain OH4384, which has an amino acid sequence as shown in SEQ ID NO:17. The β1,4-GalNAc transferases of the invention generally include an amino acid sequence that is at least about 75% identical to an amino acid sequence as set forth in SEQ ID NO:17 over a region at least about 50 amino acids in length. More preferably, the β1,4-GalNAc transferases of the invention are at least about 85% identical to this amino acid sequence, and still more preferably are at least about 95% identical to the amino acid sequence of SEQ ID NO:17, over a region of at least 50 amino acids in length. In presently preferred embodiments, the region of percent identity extends over a longer region than 50 amino acids, more preferably over a region of at least about 100 amino acids, and most preferably over the full length of the GalNAc transferase. Accordingly, the β1,4-GalNAc transferases of the invention include polypeptides that have β1,4-GalNAc transferase activity and are at least about 65% identical, more preferably at least about 70% identical, more preferably at least about 80% identical, and most preferably at least about 90% identical to the amino acid sequence of the *C. jejuni* OH 4384 β1,4-GalNAc transferases (SEQ ID NO:17) over a region of the polypeptide that is required to retain the β1,4-GalNAc transferase activity. In some embodiments, the β1,4-GalNAc transferases of the invention are identical to *C. jejuni* OH 4384 β1,4-GalNAc transferase over the entire length of the β1,4-GalNAc transferase.

Again, the percent identities can be determined by inspection, for example, or can be determined using an alignment algorithm such as the BLASTP Version 2.0 algorithm with a wordlength (W) of 3, G=11, E=1, and a BLOSUM62 substitution matrix.

One can also identify β1,4-GalNAc transferases of the invention by immunoreactivity. For example, one can prepare antibodies against the *C. jejuni* OH4384 β1,4-GalNAc transferase of SEQ ID NO:17 and determine whether the antibodies are specifically immunoreactive with a β1,4-GalNAc transferase of interest.

3. β1,3-Galactosyltransferases

Also provided by the invention are β1,3-galactosyltransferases (CgtB). When placed in a suitable reaction medium, the β1,3-galactosyltransferases of the invention catalyze the transfer of a galactose residue from a donor (e.g., UDP-Gal) to a suitable saccharide acceptor (e.g., saccharides having a terminal GalNAc residue). Among the reactions catalyzed by the β1,3-galactosyltransferases is the transfer of a galactose residue to the oligosaccharide moiety of GM2 to form the GM1a oligosaccharide moiety.

Examples of the β1,3-galactosyltransferases of the invention are those produced by *Campylobacter* species, such as *C. jejuni*. For example, one β1,3-galactosyl-transferase of the invention is that of *C. jejuni* strain OH4384, which has th-e amino acid sequence shown in SEQ ID NO:27.

Another example of a β1,3-galactosyltransferase of the invention is that of the *C. jejuni* O:2 serotype strain NCTC 11168. The amino acid sequence of this galactosyltransferase is set forth in SEQ ID NO:29. This galactosyltransferase expresses well in *E. Coli*, for example, and exhibits a high amount of soluble activity. Moreover, unlike the OH4384 CgtB, which can add more than one galactose if a reaction mixture contains an excess of donor and is incubated for a sufficiently long period of time, the NCTC 11168 β1,3-galactose does not have a significant amount of polygalactosyltransferase activity. For some applications, the polygalactosyltransferase activity of the OH4384 enzyme is desirable, but in other applications such as synthesis of GM1 mimics, addition of only one terminal galactose is desirable.

The β1,3-galactosyltransferases of the invention generally have an amino acid sequence that is at least about 75% identical to an amino acid sequence of the OH 4384 or NCTC 11168 CgtB as set forth in SEQ ID NO:27 and SEQ ID NO:29, respectively, over a region at least about 50 amino acids in length. More preferably, the β1,3-galactosyltransferases of the invention are at least about 85% identical to either of these amino acid sequences, and still more preferably are at least about 95% identical to the amino acid sequences of SEQ ID NO:27 or SEQ ID NO:29, over a region of at least 50 amino acids in length. In presently preferred embodiments, the region of percent identity extends over a longer region than 50 amino acids, more preferably over a region of at least about 100 amino acids, and most preferably over the full length of the galactosyltransferase. Accordingly, the β1,3-galactosyltransferases of the invention include polypeptides that have β1,3-galactosyltransferase activity and are at least about 65% identical, more preferably at least about 70% identical, more preferably at least about 80% identical, and most preferably at least about 90% identical to the amino acid sequence of the C. jejuni OH4384 β1,3-galactosyltransferase (SEQ ID NO:27) or the NCTC 11168 galactosyltransferase (SEQ ID NO:29) over a region of the polypeptide that is required to retain the β1,3-galactosyltransferase activity. In some embodiments, the β1,3-galactosyltransferase of the invention are identical to C. jejuni OH 4384 or NCTC 11168 β1,3-galactosyltransferase over the entire length of the β1,3-galactosyltransferase.

The percent identities can be determined by inspection, for example, or can be determined using an alignment algorithm such as the BLASTP Version 2.0 algorithm with a wordlength (W) of 3, G=21, E=1, and a BLOSUM62 substitution matrix.

The β1,3-galactosyltransferases of the invention can be obtained from the respective Campylobacter species, or can be produced recombinantly. One can identify the glycosyltransferases by assays of enzymatic activity, for example, or by detecting specific immunoreactivity with antibodies raised against the C. jejuni OH4384 β1,3-galactosyltransferase having an amino acid sequence as set forth in SEQ ID NO:27 or the C. jejuni NCTC 11168 β1,3 galactosyltransferase as set forth in SEQ ID NO:29.

4. Additional Enzymes Involved in LOS Biosynthetic Pathway

The present invention also provides additional enzymes that are involved in the biosynthesis of oligosaccharides such as those found on bacterial lipooligosaccharides. For example, enzymes involved in the synthesis of CMP-sialic acid, the donor for sialyltransferases, are provided. A sialic acid synthase is encoded by open reading frame (ORF) 8a of C. jejuni strain OH 4384 (SEQ ID NO:35) and by open reading frame 8b of strain NCTC 11168 (see, Table 3). Another enzyme involved in sialic acid synthesis is encoded by ORF 9a of OH 4384 (SEQ ID NO:36) and 9b of NCTC 11168. A CMP-sialic acid synthetase is encoded by ORF 10a (SEQ ID NO:37) and 10b of OH 4384 and NCTC 11168, respectively.

The invention also provides an acyltransferase that is involved in lipid A biosynthesis. This enzyme is encoded by open reading frame 2a of C. jejuni strain OH4384 (SEQ ID NO:32) and by open reading frame 2B of strain NCTC 11168. An acetyltransferase is also provided; this enzyme is encoded by ORF 11a of strain OH 4384 (SEQ ID NO:38); no homolog is found in the LOS biosynthesis locus of strain NCTC 11168.

Also provided are three additional glycosyltransferases. These enzymes are encoded by ORFs 3a (SEQ ID NO:33), 4a (SEQ ID NO:34), and 12a (SEQ ID NO:39) of strain OH 4384 and ORFs 3b, 4b, and 12b of strain NCTC 11168.

The invention includes, for each of these enzymes, polypeptides that include an an amino acid sequence that is at least about 75% identical to an amino acid sequence as set forth herein over a region at least about 50 amino acids in length. More preferably, the enzymes of the invention are at least about 85% identical to the respective amino acid sequence, and still more preferably are at least about 95% identical to the amino acid sequence, over a region of at least 50 amino acids in length. In presently preferred embodiments, the region of percent identity extends over a longer region than 50 amino acids, more preferably over a region of at least about 100 amino acids, and most preferably over the full length of the enzyme. Accordingly, the enzymes of the invention include polypeptides that have the respective activity and are at least about 65% identical, more preferably at least about 70% identical, more preferably at least about 80% identical, and most preferably at least about 90% identical to the amino acid sequence of the corresponding enzyme as set forth herein over a region of the polypeptide that is required to retain the respective enzymatic activity. In some embodiments, the enzymes of the invention are identical to the corresponding C. jejuni OH 4384 enzymes over the entire length of the enzyme.

B. Nucleic Acids that Encode Glycosyltransferases and Related Enzymes

The present invention also provides isolated and/or recombinant nucleic acids that encode the glycosyltransferases and other enzymes of the invention. The glycosyltransferase-encoding nucleic acids of the invention are useful for several purposes, including the recombinant expression of the corresponding glycosyltransferase polypeptides, and as probes to identify nucleic acids that encode other glycosyltransferases and to study regulation and expression of the enzymes.

Nucleic acids of the invention include those that encode an entire glycosyltransferase enzyme such as those described above, as well as those that encode a subsequence of a glycosyltransferase polypeptide. For example, the invention includes nucleic acids that encode a polypeptide which is not a full-length glycosyltransferase enzyme, but nonetheless has glycosyltransferase activity. The nucleotide sequences of the LOS locus of C. jejuni strain OH4384 is provided herein as SEQ ID NO:1, and the respective reading frames are identified. Additional nucleotide sequences are also provided, as discussed below. The invention includes not only nucleic acids that include the nucleotide sequences as set forth herein, but also nucleic acids that are substantially identical to, or substantially complementary to, the exemplified embodiments. For example, the invention includes nucleic acids that include a nucleotide sequence that is at least about 70% identical to one that is set forth herein, more preferably at least 75%, still more preferably at least 80%, more preferably at least 85%, still more preferably at least 90%, and even more preferably at least about 95% identical to an exemplified nucleotide sequence. The region of identity extends over at least about 50 nucleotides, more preferably over at least about 100 nucleotides, still more preferably over at least about 500 nucleotides. The region of a specified percent identity, in some embodiments, encompasses the coding region of a sufficient portion of the encoded enzyme to retain the respective enzyme activity. The specified percent identity, in preferred embodiments, extends over the full length of the coding region of the enzyme.

The nucleic acids that encode the glycosyltransferases of the invention can be obtained using methods that are known to those of skill in the art. Suitable nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) *C&EN* 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077–1080; Van Brunt (1990) *Biotechnology* 8: 291–294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039.

Nucleic acids that encode the glycosyltransferase polypeptides of the invention, or subsequences of these nucleic acids, can be prepared by any suitable method as described above, including, for example, cloning and restriction of appropriate sequences. As an example, one can obtain a nucleic acid that encodes a glycosyltransferase of the invention by routine cloning methods. A known nucleotide sequence of a gene that encodes the glycosyltransferase of interest, such as are described herein, can be used to provide probes that specifically hybridize to a gene that encodes a suitable enzyme in a genomic DNA sample, or to a mRNA in a total RNA sample (e.g., in a Southern or Northern blot). Preferably, the samples are obtained from prokaryotic organisms, such as *Campylobacter* species. Examples of *Campylobacter* species of particular interest include *C. jejuni*. Many *C. jejuni* O:19 strains synthesize ganglioside mimics and are useful as a source of the glycosyltransferases of the invention.

Once the target glycosyltransferase nucleic acid is identified, it can be isolated according to standard methods known to those of skill in the art (see, e.g., Sambrook et al. (1989) *Molecular Cloning: A Laboratory Manual*, 2nd Ed., Vols. 1–3, Cold Spring Harbor Laboratory; Berger and Kimmel (1987) *Methods in Enzymology*, Vol. 152: *Guide to Molecular Cloning Techniques*, San Diego: Academic Press, Inc.; or Ausubel et al. (1987) *Current Protocols in Molecular Biology*, Greene Publishing and Wiley-Interscience, New York).

A nucleic acid that encodes a glycosyltransferase of the invention can also be cloned by detecting its expressed product by means of assays based on the physical, chemical, or immunological properties. For example, one can identify a cloned bifunctional sialyltransferase-encoding nucleic acid by the ability of a polypeptide encoded by the nucleic acid to catalyze the coupling of a sialic acid in an α2,3-linkage to a galactosylated acceptor, followed by the coupling of a second sialic acid residue to the first sialic acid in an α2,8 linkage. Similarly, one can identify a cloned nucleic acid that encodes a β1,4-GalNAc transferase or a β1,3-galactosyltransferase by the ability of the encoded polypeptide to catalyze the transfer of a GalNAc residue from UDP-GalNAc, or a galactose residue from UDP-Gal, respectively, to a suitable acceptor. Suitable assay conditions are known in the art, and include those that are described in the Examples. Other physical properties of a polypeptide expressed from a particular nucleic acid can be compared to properties of known glycosyltransferase polypeptides of the invention, such as those described herein, to provide another method of identifying nucleic acids that encode glycosyltransferases of the invention. Alternatively, a putative glycosyltransferase gene can be mutated; and its role as a glycosyltransferase established by detecting a variation in the ability to produce the respective glycoconjugate.

In other embodiments, glycosyltransferase-encoding nucleic acids can be cloned using DNA amplification methods such as polymerase chain reaction (PCR). Thus, for example, the nucleic acid sequence or subsequence is PCR amplified, preferably using a sense primer containing one restriction site (e.g., XbaI) and an antisense primer containing another restriction site (e.g., HindIII). This will produce a nucleic acid encoding the desired glycosyltransferase amino acid sequence or subsequence and having terminal restriction sites. This nucleic acid can then be easily ligated into a vector containing a nucleic acid encoding the second molecule and having the appropriate corresponding restriction sites. Suitable PCR primers can be determined by one of skill in the art using the sequence information provided herein. Appropriate restriction sites can also be added to the nucleic acid encoding the glycosyltransferase of the invention, or amino acid subsequence, by site-directed mutagenesis. The plasmid containing the glycosyltransferase-encoding nucleotide sequence or subsequence is cleaved with the appropriate restriction endonuclease and then ligated into an appropriate vector for amplification and/or expression according to standard methods.

Examples of suitable primers suitable for amplification of the glycosyltransferase-encoding nucleic acids of the invention are shown in Table 2; some of the primer pairs are designed to provide a 5' NdeI restriction site and a 3' SalI site on the amplified fragment. The plasmid containing the enzyme-encoding sequence or subsequence is cleaved with the appropriate restriction endonuclease and then ligated into an appropriate vector for amplification and/or expression according to standard methods.

As an alternative to cloning a glycosyltransferase-encoding nucleic acid, a suitable nucleic acid can be chemically synthesized from a known sequence that encodes a glycosyltransferase of the invention. Direct chemical synthesis methods include, for example, the phosphotriester method of Narang et al. (1979) *Meth. Enzymol.* 68: 90–99; the phosphodiester method of Brown et al. (1979) *Meth. Enzymol.*

68: 109–151; the diethylphosphoramidite-method of Beaucage et al. (1981) *Tetra. Lett.,* 22: 1859–1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is often limited to sequences of about 100 bases, longer sequences may be obtained by the ligation of shorter sequences. Alternatively, subsequences may be cloned and the appropriate subsequences cleaved using appropriate restriction enzymes. The fragments can then be ligated to produce the desired DNA sequence.

In some embodiments, it may be desirable to modify the enzyme-encoding nucleic acids. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81–97, Roberts et al. (1987) *Nature* 328: 731–734.

In a presently preferred embodiment, the recombinant nucleic acids present in the cells of the invention are modified to provide preferred codons which enhance translation of the nucleic acid in a selected organism (e.g., *E. coli* preferred codons are substituted into a coding nucleic acid for expression in *E. coli*).

The present invention includes nucleic acids that are isolated (i.e., not in their native chromosomal location) and/or recombinant (i.e., modified from their original form, present in a non-native organism, etc.).

1. Sialyltransferases

The invention provides nucleic acids that encode sialyltransferases such as those described above. In some embodiments, the nucleic acids of the invention encode bifunctional sialyltransferase polypeptides that have both an α2,3 sialyltransferase activity and an α2,8 sialyltransferase activity. These sialyltransferase nucleic acids encode a sialyltransferase polypeptide that has an amino acid sequence that is at least about 76% identical to an amino acid sequence as set forth in SEQ ID NO:3 over a region at least about 60 amino acids in length. More preferably the sialyltransferases encoded by the nucleic acids of the invention are at least about 85% identical to the amino acid sequence of SEQ ID NO:3, and still more preferably at least about 95% identical to the amino acid sequence of SEQ ID NO:3, over a region of at least 60 amino acids in length. In presently preferred embodiments, the region of percent identity extends over a longer region than 60 amino acids, more preferably over a region of at least about 100 amino acids, and most preferably over the full length of the sialyltransferase. In a presently preferred embodiment, the sialyltransferase-encoding nucleic acids of the invention encode a polypeptide having the amino acid sequence as shown in SEQ ID NO:3.

An example of a nucleic acid of the invention is an isolated and/or recombinant form of a bifunctional sialyltransferase-encoding nucleic acid of *C. jejuni* OH4384. The nucleotide sequence of this nucleic acid is shown in SEQ ID NO:2. The sialyltransferase-encoding polynucleotide sequences of the invention are typically at least about 75% identical to the nucleic acid sequence of SEQ ID NO:2 over a region at least about 50 nucleotides in length. More preferably, the sialyltransferase-encoding nucleic acids of the invention are at least about 85% identical to this nucleotide sequence, and still more preferably are at least about 95% identical to the nucleotide sequence of SEQ ID NO:2, over a region of at least 50 amino acids in length. In presently preferred embodiments, the region of the specified percent identity threshold extends over a longer region than 50 nucleotides, more preferably over a region of at least about 100 nucleotides, and most preferably over the full length of the sialyltransferase-encoding region. Accordingly, the invention provides bifunctional sialyltransferase-encoding nucleic acids that are substantially identical to that of the *C. jejuni* strain OH4384 cstII as set forth in SEQ ID NO:2 or strain O:10 (SEQ ID NO:4). *C. jejuni* OH4384. This nucleic acid has a nucleotide sequence as shown in SEQ ID NO:16. The GalNAc transferase-encoding polynucleotide sequences of the invention are typically at least about 75% identical to the nucleic acid sequence of SEQ ID NO:16 over a region at least about 50 nucleotides in length. More preferably, the GalNAc transferase-encoding nucleic acids of the invention are at least about 85% identical to this nucleotide sequence, and still more preferably are at least about 95% identical to the nucleotide sequence of SEQ ID NO:16, over a region of at least 50 amino acids in length. In presently preferred embodiments, the region of percent identity extends over a longer region than 50 nucleotides, more preferably over a region of at least about 100 nucleotides, and most preferably over the full length of the GalNAc transferase-encoding region.

To identify nucleic acids of the invention, one can use visual inspection, or can use a suitable alignment algorithm. An alternative method-by which one can identify a GalNAc transferase-encoding nucleic acid of the invention is by hybridizing, under stringent conditions, the nucleic acid of interest to a nucleic acid that includes a polynucleotide sequence of SEQ ID NO:16.

3. β1,3-Galactosyltransferases

The invention also provides nucleic acids that include polynucleotide sequences that encode a polypeptide that has β1,3-galactosyltransferase activity (CgtB). The β1,3-galactosyltransferase polypeptides encoded by these nucleic acids of the invention preferably include an amino acid sequence that is at least about 75% identical to an amino acid sequence of a *C. jejuni* strain OH4384 β1,3-galactosyltransferase as set forth in SEQ ID NO:27, or to that of a strain NCTC 11168 β1,3-galactosyltransferase as set forth in SEQ ID NO:29, over a region at least about 50 amino acids in length. More preferably, the galactosyltransferase polypeptides encoded by these nucleic acids of the invention are at least about 85% identical to this amino acid sequence, and still more preferably are at least about 95% identical to the amino acid sequence of SEQ ID NO:27 or SEQ ID NO:29, over a region of at least 50 amino acids in length. In presently preferred embodiments, the region of percent identity extends over a longer region than 50 amino acids, more preferably over a region of at least about 100 amino acids, and most preferably over the full length of the galactosyltransferase polypeptide-encoding region.

Other sialyltransferase-encoding nucleic acids of the invention encode sialyltransferases have α2,3 sialyltransferase activity but lack substantial α2,8 sialyltransferase activity. For example, nucleic acids that encode a CstII α2,3 sialyltransferase from *C. jejuni* serostrain O:19 (SEQ ID NO:8) and NCTC 11168 are provided by the invention; these enzymes have little or no α2,8-sialyltransferase activity (Table 6).

To identify nucleic acids of the invention, one can use visual inspection, or can use a suitable alignment algorithm.

An alternative method by which one can identify a bifunctional sialyltransferase-encoding nucleic acid of the invention is by hybridizing, under stringent conditions, the nucleic acid of interest to a nucleic acid that includes a polynucleotide sequence of a sialyltransferase as set forth herein.

2. β1,4-GalNAc Transferases

Also provided by the invention are nucleic acids that include polynucleotide sequences that encode a GalNAc transferase polypeptide that has β1,4-GalNAc transferase activity. The polynucleotide sequences encode a GalNAc transferase polypeptide that has an amino acid sequence that is at least about 70% identical to the C. jejuni OH4384 β1,4-GalNAc transferase, which has an amino acid sequence as set forth in SEQ ID NO:17, over a region at least about 50 amino acids in length. More preferably the GalNAc transferase polypeptide encoded by the nucleic acids of the invention are at least about 80% identical to this amino acid sequence, and still more preferably at least about 90% identical to the amino acid sequence of SEQ ID NO:17, over a region of at least 50 amino acids in length. In presently preferred embodiments, the region of percent identity extends over a longer region than 50 amino acids, more preferably over a region of at least about 100 amino acids, and most preferably over the full length of the GalNAc transferase polypeptide. In a presently preferred embodiment, the GalNAc transferase polypeptide-encoding nucleic acids-f the invention encode a polypeptide having the amino acid sequence as shown in SEQ ID NO:17. To identify nucleic acids of the invention, one can use visual inspection, or can use a suitable alignment algorithm.

One example of a GalNAc transferase-encoding nucleic acid of the invention is an isolated and/or recombinant form of the GalNAc transferase-encoding nucleic acid of C. jejuni OH4384. This nucleic acid has a nucleotide sequence as shown in SEQ ID NO:16. The GalNAc transferase-encoding polynucleotide sequences of the invention are typically at least about 75% identical to the nucleic acid sequence of SEQ ID NO:16 over a region at least about 50 nucleotides in length. More preferably, the GalNAc transferase-encoding nucleic acids of the invention are at least about 85% identical to this nucleotide sequence, and still more preferably are at least about 95% identical to the nucleotide sequence of SEQ ID NO:16, over a region of at least 50 amino acids in length. In presently preferred embodiments, the region of percent identity extends over a longer region than 50 nucleotides, more preferably over a region of at least about 100 nucleotides, and most preferably over the full length of the GalNAc transferase-encoding region.

To identify nucleic acids of the invention, one can use visual inspection, or can use a suitable alignment algorithm. An alternative method by which one can identify a GalNAc transferase-encoding nucleic acid of the invention is by hybridizing, under stringent conditions, the nucleic acid of interest to a nucleic acid that includes a polynucleotide sequence of SEQ ID NO: 16.

3. β1,3-Galactosyltransferases

The invention also provides nucleic acids that include polynucleotide sequences that encode a polypeptide that has β1,3-galactosyltransferase activity (CgtB). The β1,3-galactosyltransferase polypeptides encoded by these nucleic acids of the invention preferably include an amino acid sequence that is at least about 75% identical to an amino acid sequence of a C. jejuni strain OH4384 β1,3-galactosyltransferase as set forth in SEQ ID NO:27, or to that of a strain NCTC 11168 β1,3-galactosyltransferase as set forth in SEQ ID NO:29, over a region at least about 50 amino acids in length. More preferably, the galactosyltransferase polypeptides encoded by these nucleic acids of the invention are at least about 85% identical to this amino acid sequence, and still more preferably are at least about 95% identical to the amino acid sequence of SEQ ID NO:27 or SEQ ID NO:29, over a region of at least 50 amino acids in length. In presently preferred embodiments, the region of percent identity extends over a longer region than 50 amino acids, more preferably over a region of at least about 100 amino acids, and most preferably over the full length of the galactosyltransferase polypeptide-encoding region.

One example of a β1,3-galactosyltransferase-encoding nucleic acid of the invention is an isolated and/or recombinant form of the β1,3-galactosyltransferase-encoding nucleic acid of C. jejuni OH4384. This nucleic acid includes a nucleotide sequence as shown in SEQ ID NO:26. Another suitable β1,3-galactosyltransferase-encoding nucleic acid includes a nucleotide sequence of a C. jejuni NCTC 11168 strain, for which the nucleotide sequence is shown in SEQ ID NO:28. The β1,3-galactosyltransferase-encoding polynucleotide sequences of the invention are typically at least about 75% identical to the nucleic acid sequence of SEQ ID NO:26 or that of SEQ ID NO:28 over a region at least about 50 nucleotides in length. More preferably, the β1,3-galactosyltransferase-encoding nucleic acids of the invention are at least about 85% identical to at least one of these nucleotide sequences, and still more preferably are at least about 95% identical to the nucleotide sequences of SEQ ID NO:26 and/or SEQ ID NO:28, over a region of at least 50 amino acids in length. In presently preferred embodiments, the region of percent identity extends over a longer region than 50 nucleotides, more preferably over a region of at least about 100 nucleotides, and most preferably over the full length of the β1,3-galactosyltransferase-encoding region.

To identify nucleic acids of the invention, one can use visual inspection, or can use a suitable alignment algorithm. An alternative method by which one can identify a galactosyltransferase polypeptide-encoding nucleic acid of the invention is by hybridizing, under stringent conditions, the nucleic acid of interest to a nucleic acid that includes a polynucleotide sequence of SEQ ID NO:26 or SEQ ID NO:28.

4. Additional Enzymes Involved in LOS Biosynthetic Pathway

Also provided are nucleic acids that encode other enzymes that are involved in the LOS biosynthetic pathway of prokaryotes such as Campylobacter. These nucleic acids encode enzymes such as, for example, sialic acid synthase, which is encoded by open reading frame (ORF) 8a of C. jejuni strain OH 4384 and by open reading frame 8b of strain NCTC 11168 (see, Table 3), another enzyme involved in sialic acid synthesis, which is encoded by ORF 9a of OH 4384 and 9b of NCTC 11168, and a CNP-sialic acid synthetase which is encoded by ORF 10a and 10b of OH 4384 and NCTC 11168, respectively.

The invention also provides nucleic acids that encode an acyltransferase that is involved in lipid A biosynthesis. This enzyme is encoded by open reading frame 2a of C. jejuni strain OH4384 and by open reading frame 2B of strain NCTC 11168. Nucleic acids that encode an acetyltransferase are also provided; this enzyme is encoded by ORF 11a of strain OH 4384; no homolog is found in the LOS biosynthesis locus of strain NCTC 11168.

Also provided are nucleic acids that encode three additional glycosyltransferases. These enzymes are encoded by ORFs 3a, 4a, and 12a of strain OH 4384 and ORFs 3b, 4b, and 12b of strain NH 11168 (FIG. 1).

C. Expression Cassettes and Expression of the Glycosyltransferases

The present invention also provides expression cassettes, expression vectors, and recombinant host cells that can be used to produce the glycosyltransferases and other enzymes of the invention. A typical expression cassette contains a promoter operably linked to a nucleic acid that encodes the glycosyltransferase or other enzyme of interest. The expression cassettes are typically included on expression vectors that are introduced into suitable host cells, preferably prokaryotic host cells. More than one glycosyltransferase polypeptide can be expressed in a single host cell by placing multiple transcriptional cassettes in a single expression vector, by constructing a gene that encodes a fusion protein consisting of more than one glycosyltransferase, or by utilizing different expression vectors for each glycosyltransferase.

In a preferred embodiment, the expression cassettes are useful for expression of the glycosyltransferases in prokaryotic host cells. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21–25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

Either constitutive or regulated promoters can be used in the present invention. Regulated promoters can be advantageous because the host cells can be grown to high densities before expression of the glycosyltransferase polypeptides is induced. High level expression of heterologous proteins slows cell growth in some situations. Regulated promoters especially suitable for use in *E. coli* include the bacteriophage lambda $P_L$ promoter, the hybrid trp-lac promoter (Amann et al., *Gene* (1983) 25: 167; de Boer et al., *Proc. Natl. Acad. Sci. USA* (1983) 80: 21, and the bacteriophage T7 promoter (Studier et al., *J. Mol. Biol.* (1986); Tabor et al., (1985). These promoters and their use are discussed in Sambrook et al., supra. A presently preferred regulable promoter is the dual tac-gal promoter, which is described in PCT/US97/20528 (Int'l. Publ. No. WO 9820111).

For expression of glycosyltransferase polypeptides in prokaryotic cells other than *E. coli*, a promoter that functions in the particular prokaryotic species is required. Such promoters can be obtained from genes that have been cloned from the species, or heterologous promoters can be used. For example, a hybrid trp-lac promoter functions in *Bacillus* in addition to *E. coli*. Promoters suitable for use in eukaryotic host cells are well known to those of skill in the art.

A ribosome binding site (RBS) is conveniently included in the expression cassettes of the invention that are intended for use in prokaryotic host cells. An RBS in *E. coli*, for example, consists of a nucleotide sequence 3–9 nucleotides in length located 3–11 nucleotides upstream of the initiation codon (Shine and Dalgarno, *Nature* (1975) 254: 34; Steitz, *In Biological regulation and development: Gene expression* (ed. R. F. Goldberger), vol. 1, p. 349, 1979, Plenum Publishing, NY).

Translational coupling can be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary-structure in the RNA, allowing for the efficient initiation of translation. See Squires et. al. (1988) *J. Biol. Chem.* 263: 16297–16302.

The glycosyltransferase polypeptides of the invention can be expressed intracellularly, or can be secreted from the cell. Intracellular expression often results in high yields. If necessary, the amount of soluble, active glycosyltransferase polypeptides can be increased by performing refolding procedures (see, e.g., Sambrook et al., supra.; Marston et al., *Bio/Technology* (1984) 2: 800; Schoner et al., *Bio/Technology* (1985) 3: 151). In embodiments in which the glycosyltransferase polypeptides are secreted from the cell, either into the periplasm or into the extracellular medium, the polynucleotide sequence that encodes the glycosyltransferase is linked to a polynucleotide sequence that encodes a cleavable signal peptide sequence. The signal sequence directs translocation of the glycosyltransferase polypeptide through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad. Sci. USA* (1985) 82: 7212; Talmadge et al., *Proc. Natl. Acad. Sci. USA* (1980) 77: 3988; Takahara et al., *J. Biol. Chem.* (1985) 260: 2670).

The glycosyltransferase polypeptides of the invention can also be produced as fusion proteins. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.). For certain applications, it may be desirable to cleave the non-glycosyltransferase amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

A suitable system for obtaining recombinant proteins from *E. coli* which maintains the integrity of their N-termini has been described by Miller et al. *Biotechnology* 7:698–704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal residue.

Glycosyltransferases of the invention can be expressed in a variety of host cells, including *E. coli*, other bacterial hosts, yeast, and various higher eukaryotic cells such as the COS, CHO and HeLa cells lines and myeloma cell lines. Examples of useful bacteria include, but are not limited to, *Escherichia, Enterobacter, Azotobacter, Erwinia, Bacillus, Pseudomonas, Klebsielia, Proteus, Salmonella, Serratia, Shigella, Rhizobia, Vitreoscilla,* and *Paracoccus*. The recombinant glycosyltransferase-encoding nucleic acid is operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The expression vectors of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant glycosyltransferase polypeptides can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology* Vol. 182: *Guide to Protein Purification*., Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production). The glycosyltransferases can also be used in an unpurified or semi-purified state. For example, a host cell that expresses the glycosyltransferase can be used directly in a glycosyltransferase reaction, either with or without processing such as permeabilization or other cellular disruption.

One of skill would recognize that modifications can be made to the glycosyltransferase proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

D. Methods and Reaction Mixtures for Synthesis of Oligosaccharides

The invention provides reaction mixtures and methods in which the glycosyltransferases of the invention are used to prepare desired oligosaccharides (which are composed of two or more saccharides). The glycosyltransferase reactions of the invention take place in a reaction medium comprising at least one glycosyltransferase, a donor substrate, an acceptor sugar and typically a soluble divalent metal cation. The methods rely on the use of the glycosyltransferase to catalyze the addition of a saccharide to a substrate (also referred to as an "acceptor") saccharide. A number of methods of using glycosyltransferases to synthesize desired oligosaccharide structures are known. Exemplary methods are described, for instance, WO 96/32491, Ito et al. (1993) *Pure Appl. Chem.* 65:753, and U.S. Pat. Nos. 5,352,670, 5,374,541, and 5,545,553.

For example, the invention provides methods for adding sialic acid in an α2,3 linkage to a galactose residue, by contacting a reaction mixture comprising an activated sialic acid (e.g., CMP-NeuAc, CMP-NeuGc, and the like) to an acceptor moiety that includes a terminal galactose residue in the presence of a bifunctional sialyltransferase of the invention. In presently preferred embodiments, the methods also result in the addition of a second sialic acid residue which is linked to the first sialic acid by an α2,8 linkage. The product of this method is Siaα2,8-Siaα2,3-Gal-. Examples of suitable acceptors include a terminal Gal that is linked to GlcNAc or Glc by a β1,4 linkage, and a terminal Gal that is β1,3-linked to either GlcNAc or GalNAc. The terminal residue to which the sialic acid is attached can itself be attached to, for example, H, a saccharide, oligosaccharide, or an aglycone group having at least one carbohydrate atom. In some embodiments, the acceptor residue is a portion of an oligosaccharide that is attached to a protein, lipid, or proteoglycan, for example.

In some embodiments, the invention provides reaction mixtures and methods for synthesis of gangliosides, lysogangliosides, ganglioside mimics, lysoganglioside mimics, or the carbohydrate portions of these molecules. These methods and reaction mixtures typically include as the galactosylated acceptor moiety a compound having a formula selected from the group consisting of Gal4Glc-R$^1$ and Gal3GalNAc-R$^2$; wherein R$^1$ is selected from the group consisting of ceramide or other glycolipid, R$^2$ is selected from the group consisting of Gal4GlcCer, (Neu5Ac3) Gal4GlcCer, and (Neu5Ac8Neu5c3)Gal4GlcCer. For example, for ganglioside synthesis the galactosylated acceptor can be selected from the group consisting of Gal4GlcCer, Gal3GalNAc4(Neu5Ac3)Gal4GlcCer, and Gal3GalNAc4 (Neu5Ac8Neu5c3) Gal4GlcCer.

The methods and reaction mixtures of the invention are useful for producing any of a large number of gangliosides, lysogangliosides, and related structures. Many gangliosides of interest are described in Oettgen, H. F., ed., *Gangliosides and Cancer*, VCH, Germany, 1989, pp. 10–15, and references cited therein. Gangliosides of particular interest include, for example, those found in the brain as well as other sources which are listed in Table 1.

TABLE 1

| Ganglioside Formulas and Abbreviations | |
|---|---|
| Structure | Abbreviation |
| Neu5Ac3Gal4GlcCer | GM3 |
| GalNAc4(Neu5Ac3)Gal4GlcCer | GM2 |
| Gal3GalNAc4(Neu5Ac3)Gal4GlcCer | GM1a |
| Neu5Ac3Gal3GalNAc4Gal4GlcCer | GM1b |
| Neu5Ac8Neu5Ac3Gal4GlcCer | GD3 |

TABLE 1-continued

Ganglioside Formulas and Abbreviations

| Structure | Abbreviation |
|---|---|
| GalNAc4(Neu5Ac8Neu5Ac3)Gal4GlcCer | GD2 |
| Neu5Ac3Gal3GalNAc4(Neu5Ac3)Gal4GlcCer | GD1a |
| Neu5Ac3Gal3(Neu5Ac6)GalNAc4Gal4GlcCer | GD1α |
| Gal3GalNAc4(Neu5Ac8Neu5Ac3)Gal4GlcCer | GD1b |
| Neu5Ac8Neu5Ac3Gal3GalNAc4(Neu5Ac3)Gal4GlcCer | GT1a |
| Neu5Ac3Gal3GalNAc4(Neu5Ac8Neu5Ac3)Gal4GlcCer | GT1b |
| Gal3GalNAc4(Neu5Ac8Neu5Ac8Neu5Ac3)Gal4GlcCer | GT1c |
| Neu5Ac8Neu5Ac3Gal3GalNAc4(Neu5Ac8Neu5c3)Gal4GlcCer | GQ1b |

Nomenclature of Glycolipids, IUPAC-IUB Joint Commission on Biochemical Nomenclature (Recommendations 1997); Pure Appl. Chem. (1997) 69: 2475–2487; Eur. J. Biochem (1998) 257: 293–298) (www.chem.qmw.ac.uk/iupac/misc/glylp.html).

The bifunctional sialyltransferases of the invention are particularly useful for synthesizing the gangliosides GD1a, GD1b, GT1a, GT1b, GT1c, and GQ1b, or the carbohydrate portions of these gangliosides, for example. The structures for these gangliosides, which are shown in Table 1, requires both an α2,3- and an α2,8-sialyltransferase activity. An advantage provided by the methods and reaction mixtures of the invention is that both activities are present in a single polypeptide.

The glycosyltransferases of the invention can be used in combination with additional glycosyltransferases and other enzymes. For example, one can use a combination of sialyltransferase and galactosyltransferases. In some embodiments of the invention, the galactosylated acceptor that is utilized by the bifunctional sialyltransferase is formed by contacting a suitable acceptor with UDP-Gal and a galactosyltransferase. The galactosyltransferase polypeptide, which can be one that is described herein, transfers the Gal residue from the UDP-Gal to the acceptor.

Similarly, one can use the β1,4-GalNAc transferases of the invention to synthesize an acceptor for the galactosyltransferase. For example, the acceptor saccharide for the galactosyltransferase can formed by contacting an acceptor for a GalNAc transferase with UDP-GalNAc and a GalNAc transferase polypeptide, wherein the GalNAc transferase polypeptide transfers the GalNAc residue from the UDP-GalNAc to the acceptor for the GalNAc transferase.

In this group of embodiments, the enzymes and substrates can be combined in an initial reaction mixture, or the enzymes and reagents for a second glycosyltransferase cycle can be added to the reaction medium once the first glycosyltransferase cycle has neared completion. By conducting two glycosyltransferase cycles in sequence in a single vessel; overall yields are improved over procedures in which an intermediate species is isolated. Moreover, cleanup and disposal of extra solvents and by-products is reduced.

The products produced by the above processes can be used without purification. However, it is usually preferred to recover the product. Standard, well known techniques for recovery of glycosylated saccharides such as thin or thick layer chromatography, or ion exchange chromatography. It is preferred to use membrane filtration, more preferably utilizing a reverse osmotic membrane, or one or more column chromatographic techniques for the recovery.

E. Uses of Glycoconjugates Produced using Glycosyltransferases and Methods of the Invention The oligosaccharide compounds that are made using the glycosyltransferases and methods of the invention can be used in a variety of applications, e.g., as antigens, diagnostic reagents, or as therapeutics. Thus, the present invention also provides pharmaceutical compositions which can be used in treating a variety of conditions. The pharmaceutical compositions are comprised of oligosaccharides made according to the methods described above.

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985). For a brief review of methods for drug delivery, see, Langer, *Science* 249:1527–1533 (1990).

The pharmaceutical compositions are intended for parenteral, intranasal, topical, oral or local administration, such as by aerosol or transdermally, for prophylactic and/or therapeutic treatment. Commonly, the pharmaceutical compositions are administered parenterally, e.g., intravenously. Thus, the invention provides compositions for parenteral administration which comprise the compound dissolved or suspended in an acceptable carrier, preferably an aqueous carrier, e.g., water, buffered water, saline, PBS and the like. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the oligosaccharides of the invention can be incorporated into liposomes formed from standard vesicle-forming lipids. A variety of methods are available for preparing liposomes, as described in, e.g., Szoka et al., *Ann. Rev. Biophys. Bioeng.* 9:467 (1980), U.S. Pat. Nos. 4,235,871, 4,501,728 and 4,837,028. The targeting of liposomes using a variety of targeting agents (e.g., the sialyl galactosides of the invention) is well known in the art (see, e.g., U.S. Pat. Nos. 4,957,773 and 4,603,044).

The compositions containing the oligosaccharides can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective dose." Amounts effective for this use will depend on the severity of the disease and the weight and general state of the patient, but generally range from about 0.5 mg to about 40 g of oligosaccharide per day for a 70 kg patient, with dosages of from about 5 mg to about 20 g of the compounds per day being more commonly used.

Single or multiple administrations of the compositions can be carried out with dose levels and pattern being selected by the treating physician. In any event, the pharmaceutical formulations should provide a quantity of the oligosaccharides of this invention sufficient to effectively treat the patient.

The oligosaccharides may also find use as diagnostic reagents. For example, labeled compounds can be used to locate areas of inflammation or tumor metastasis in a patient suspected of having an inflammation. For this use, the compounds can be labeled with appropriate radioisotopes, for example, $^{125}I$, $^{14}C$, or tritium.

The oligosaccharide of the invention can be used as an immunogen for the production of monoclonal or polyclonal antibodies specifically reactive with the compounds of the invention. The multitude of techniques available to those skilled in the art for production and manipulation of various immunoglobulin molecules can be used in the present invention. Antibodies may be produced by a variety of means well known to those of skill in the art.

The production of non-human monoclonal antibodies, e.g., murine, lagomorpha, equine, etc., is well known and may be accomplished by, for example, immunizing the animal with a preparation containing the oligosaccharide of the invention. Antibody-producing cells obtained from the immunized animals are immortalized and screened, or screened first for the production of the desired antibody and then immortalized. For a discussion of general procedures of monoclonal antibody production, see, Harlow and Lane, *Antibodies, A Laboratory Manual* Cold Spring Harbor Publications, N.Y. (1988).

EXAMPLE

The following example is offered to illustrate, but not to limit the present invention.

This Example describes the use of two strategies for the cloning of four genes responsible for the biosynthesis of the GT1a ganglioside mimic in the LOS of a bacterial pathogen, *Campylobacter jejuni* OH4384, which has been associated with Guillain-Barré syndrome (Aspinall et al. (1994) *Infect. Immun.* 62: 2122–2125). Aspinal et al. ((1994) *Biochemistry* 33: 241–249) showed that this strain has an outer core LPS that mimics the tri-sialylated ganglioside GT1a. We first cloned a gene encoding an α-2,3-sialyltransferase (cst-I) using an activity screening strategy. We then used raw nucleotide sequence information from the recently completed sequence of *C. jejuni* NCTC 11168 to amplify a region involved in LOS biosynthesis from *C. jejuni* OH4384. Using primers that are located in the heptosyltransferases I and II, the 11.47 kb LOS biosynthesis locus from *C. jejuni* OH4384 was amplified. Sequencing revealed that the locus encodes 13 partial or complete open reading frames (ORFs), while the corresponding locus in *C. jejuni* NCTC 11168 spans 13.49 kb and contains 15 ORFs, indicating a different organization between these two strains.

Potential glycosyltransferase genes were cloned individually, expressed in *Escherichia coli* and assayed using synthetic fluorescent oligosaccharides as acceptors. We identified genes that encode a β-1,4-N-acetylgalactosaminyltransferase (cgtA), a β-1,3-galactosyltransferase (cgtB) and a bifunctional sialyltransferase (cst-II) which transfers sialic acid to O-3 of galactose and to O-8 of a sialic acid that is linked α-2,3- to a galactose. The linkage specificity of each identified glycosyltransferase was confirmed by NMR analysis at 600 MHz on nanomole amounts of model compounds synthesized in vitro. Using a gradient inverse broadband nano-NMR probe, sequence information could be obtained by detection of $^3J(C, H)$ correlations across the glycosidic bond. The role of cgtA and cst-II in the synthesis of the GT1a mimic in *C. jejuni* OH4384were confirmed by comparing their sequence and activity with corresponding homologues in two related *C. jejuni* strains that express shorter ganglioside mimics in their LOS. Thus, these three enzymes can be used to synthesize a GT1a mimic starting from lactose.

The abbreviations used are: CE, capillary electrophoresis; CMP-Neu5Ac, cytidine monophosphate-N-acetyl-neuraminic acid; COSY, correlated spectroscopy; FCHASE, 6-(5-fluorescein-carboxamido)-hexanoic acid succimidyl ester; GBS, Guillain-Barré syndrome; HMBC, heteronuclear multiple bond coherence; HSQC, heteronuclear single quantum coherence; LIF, laser induced fluorescence; LOS, lipooligosaccharide; LPS, lipopolysaccharide; NOE, nuclear Overhauser effect; NOESY, NOE spectroscopy; TOCSY, total correlation spectroscopy.

Experimental Procedures

Bacterial Strains

The following *C. jejuni* strains were used in this study: serostain O:19 (ATCC #43446); serotype O:19 (strains OH4382 and OH4384 were obtained from the Laboratory Centre for Disease Control (Health Canada, Winnipeg, Manitoba)); and serotype O:2 (NCTC #11168). *Escherichia coli* DH5α was used for the HindIII library while *E. coli* AD202 (CGSG #7297) was used to express the different cloned glycosyltransferases.

Basic Recombinant DNA Methods.

Genomic DNA isolation from the *C. jejuni* strains was performed using Qiagen Genomic-tip 500/G (Qiagen Inc., Valencia, Calif.) as described previously (Gilbert et al. (1996) *J. Biol. Chem.* 271: 28271–28276). Plasmid DNA isolation, restriction enzyme digestions, purification of DNA fragments for cloning, ligations and transformations were performed as recommended by the enzyme supplier, or the manufacturer of the kit used for the particular procedure. Long PCR reactions (>3 kb) were performed using the Expand™ long template PCR system as described by the manufacturer (Boehringer Mannheim, Montreal). PCR reactions to amplify specific ORFs were performed using the Pwo DNA polymerase as described by the manufacturer (Boehringer Mannheim, Montreal). Restriction and DNA modification enzymes were purchased from New England Biolabs Ltd. (Mississauga, ON). DNA sequencing was performed using an Applied Biosystems (Montreal) model 370A automated DNA sequencer and the manufacturer's cycle sequencing kit.

Activity Screening for Sialyltransferase from *C. jejuni*

The genomic library was prepared using a partial HindIII digest of the chromosomal DNA of *C. jejuni* OH4384. The partial digest was purified on a QIAquick column (QIAGEN Inc.) and ligated with HindIII digested pBluescript SK-. *E. coli* DH5α was electroporated with the ligation mixture and the cells were plated on LB medium with 150 µg/mL ampicillin, 0.05 mM IPTG and 100 µg/mL X-Gal (5-Bromo-4-chloro-indolyl-β-D-galactopyranoside). White colonies were picked in pools of 100 and were resuspended in 1 mL of medium with 15% glycerol. Twenty µL of each pool were used to inoculate 1.5 mL of LB medium supplemented with 150 µg/mL ampicillin. After 2 h of growth at 37° C., IPTG was added to 1 mM and the cultures were grown for another 4.5 h. The cells were recovered by centrifugation, resuspended in 0.5 mL of 50 mM Mops (pH 7, 10 mM $MgCl_2$) and sonicated for 1 min. The extracts were assayed for sialyltransferase activity as described below except that the incubation time and temperature were 18 h and 32° C., respectively. The positive pools were plated for single colonies, and 200 colonies were picked and tested for activity in pools of 10. Finally the colonies of the positive pools were tested individually which led to the isolation of a two positive clones, pCJH9 (5.3 kb insert) and pCJH101 (3.9 kb insert). Using several sub-cloned fragments and custom-made primers, the inserts of the two clones were, completely sequenced on both strands. The clones with individual HindIII fragments were also tested for sialyltransferase activity and the insert of the only positive one (a 1.1 kb HindIII fragment cloned in pBluescript SK-) was transferred to pUC118 using KpnI and PstI sites in order to obtain the insert in the opposite orientation with respect to the plac promoter.

Cloning and Sequencing of the LPS Biosynthesis Locus.

The primers used to amplify the LPS biosynthesis locus of *C. jejuni* OH4384 were based on preliminary sequences available from the website of the *C. jejuni* sequencing group (Sanger Centre, UK) who sequenced the complete genome of the strain NCTC11168. The primers CJ-42 and CJ-43 (all primers sequences are described in Table 2) were used to amplify an 11.47 kb locus using the Expand™ long template PCR system. The PCR product was purified on a S-300 spin column (Pharmacia Biotech) and completely sequence on both strands using a combination of primer walking and sub-cloning of HindIII fragments. Specific ORF's were amplified using the primers described in Table 2 and the Pwo DNA polymerase. The PCR products were digested using the appropriate restriction enzymes (see Table 2) and were cloned in pCWori+.

TABLE 2

Primers used for Amplification of Open Reading Frames

Primers used to amplify the LPS core biosynthesis locus

CJ42: Primer in heptosylTase-II (SEQ ID NO:40)

5' GC CAT TAC CGT ATC GCC TAA CCA GG 3' 25 mer

CJ43: Primer in heptosylTase-I (SEQ ID NO:41)

5' AAA GAA TAC GAA TTT GCT AAA GAG G 3' 25 mer

Primers used to amplify and clone ORF 5a:

CJ-106 (3' primer, 41 mer)(SEQ ID NO:42)

SalI
5' CCT AG*G TCG ACT* TAA AAC AAT GTT AAG AAT ATT TTT TTT AG 3'

CJ-157 (5' primer, 37 mer)(SEQ ID NO:43)

NdeI
5' CTT AGG AGG TCA *TAT G*CT ATT TCA ATC ATA CTT TGT G 3'

Primers used to amplify and clone ORF 6a:

CJ-105 (3' primer, 37 mer)(SEQ ID NO:44)

SalI
5' CCT AG*G TCG ACC* TCT AAA AAA AAT ATT CTT AAC ATT G 3'

CJ-133 (5' primer, 39 mer)(SEQ ID NO:45)

NdeI
5' CTTAGGAGGT*CATATG*TTTAAAATTTCAATCATCTTACC 3'

TABLE 2-continued

Primers used for Amplification of Open Reading Frames

Primers used to amplify and clone ORF 7a:

CJ-131 (5' primer, 41 mer)(SEQ ID NO:46)

```
        NdeI
5' CTTAGGAGGTCATATGAAAAAAGTTATTATTGCTGGAAATG 3'
```

CJ-132 (3' primer, 41 mer)(SEQ ID NO:47)

```
        SalI
5' CCTAGGTCGACTTATTTTCCTTTGAAATAATGCTTTATATC 3'
```

Expression in *E. coli* and Glycosyltransferase Assays.

The various constructs were transferred to *E. coli* AD202 and were tested for the expression of glycosyltransferase activities following a 4 h induction with 1 mM IPTG. Extracts were made by sonication and the enzymatic reactions were performed overnight at 32° C. FCHASE-labeled oligosaccharides were prepared as described previously (Wakarchuk et al. (1996) *J. Biol. Chem.* 271: 19166–19173). Protein concentration was determined using the bicinchoninic acid protein assay kit (Pierce, Rockford, Ill). For all of the enzymatic assays one unit of activity was defined as the amount of enzyme that generated one μmol of product per minute.

The screening assay for α-2,3-sialyltransferase activity in pools of clones contained 1 mM Lac-FCHASE, 0.2 mM CNT-Neu5Ac, 50 mM Mops pH 7, 10 MM $MnCl_2$ and 10 mM $MgCl_2$ in a final volume of 10 μL. The various subcloned ORFs were tested for the expression of glycosyltransferase activities following a 4 h induction of the cultures with 1 mM IPTG. Extracts were made by sonication and the enzymatic reactions were performed overnight at 32° C.

The β-1,3-galactosyltransferase was assayed using 0.2 mM GM2-FCHASE, 1 mM UDP-Gal, 50 mM Mes pH 6, 10 mM $MnCl_2$ and 1 mM DTT. The β-1,4-GalNAc transferase was assayed using 0.5 mM GM3-FCHASE, 1 mM UDP-GalNAc, 50 mM Hepes pH 7 and 10 mM $MnCl_2$. The α-2,3-sialyltransferase was assayed using 0.5 mM Lac-FCHASE, 0.2 mM CMP-Neu5Ac, 50 mM Hepes pH 7 and 10 mM $MgCl_2$. The α-2,8-sialyltransferase was assayed using 0.5 mM GM3-FCHASE, 0.2 mM CMP-Neu5Ac, 50 mM Hepes pH 7 and 10 mM $MnCl_2$.

The reaction mixes were diluted appropriately with 10 mM NaOH and analyzed by capillary electrophoresis performed using the separation and detection conditions as described previously (Gilbert et al. (1996) *J. Biol. Chem.* 271, 28271–28276). The peaks from the electropherograms were analyzed using manual peak integration with the P/ACE Station software. For rapid detection of enzyme activity, samples from the transferase reaction mixtures were examined by thin layer chromatography on silica-60 TLC plates (E. Merck) as described previously (Id.).

NMR Spectroscopy

NMR experiments were performed on a Varian INOVA 600 NMR spectrometer. Most experiments were done using a 5 mm Z gradient triple resonance probe. NMR samples were prepared from 0.3–0.5 mg (200–500 nanomole) of FCHASE-glycoside. The compounds were dissolved in $H_2O$ and the pH was adjusted to 7.0 with dilute NaOH. After freeze drying the samples were dissolved in 600 μL $D_2O$. All NMR experiments were performed as previously described (Pavliak et al. (1993) *J. Biol. Chem.* 268: 14146–14152; Brisson et al. (1997) *Biochemistry* 36: 3278–3292) using standard techniques such as COSY, TOCSY, NOESY, 1D-NOESY, 1D-TOCSY and HSQC. For the proton chemical shift reference, the methyl resonance of internal acetone was set at 2.225 ppm ($^1H$). For the $^{13}C$ chemical shift reference, the methyl resonance of internal acetone was set at 31.07 ppm relative to external dioxane at 67.40 ppm. Homonuclear experiments were on the order of 5–8 hours each. The 1D NOESY experiments for GD3-FCHASE,[0.3 mM], with 8000 scans and a mixing time of 800 ms was done for a duration of 8.5 h each and processed with a line broadening factor of 2–5 Hz. For the 1D NOESY of the resonances at 4.16 ppm, 3000 scans were used. The following parameters were used to acquire the HSQC spectrum: relaxation delay of 1.0 s, spectral widths in $F_2$ and $F_1$ of 6000 and 24147 Hz, respectively, acquisition times in $t_2$ of 171 ms. For the $t_1$ dimension, 128 complex points were acquired using 256 scans per increment. The sign discrimination in $F_1$ was achieved by the States method. The total acquisition time was 20 hours. For GM2-FCHASE, due to broad lines, the number of scans per increment was increased so that the HSQC was performed for 64 hours. The phase-sensitive spectrum was obtained after zero filling to 2048×2048 points. Unshifted gaussian window functions were applied in both dimensions. The HSQC spectra were plotted at a resolution of 23 Hz/point in the $^{13}C$ dimension and 8 Hz/point in the proton dimension. For the observation of the multiplet splittings, the $^1H$ dimension was reprocessed at a resolution of 2 Hz/point using forward linear prediction and a π/4-shifted squared sinebell function. All the NMR data was acquired using Varian's standard sequences provided with the VNMR 5.1 or VNMR 6.1 software. The same program was used for processing.

A gradient inverse broadband nano-NMR probe (Varian) was used to perform the gradient HMBC (Bax and Summers (1986) *J. Am. Chem. Soc.* 108, 2093–2094; Parella et al. (1995) *J. Mag. Reson. A* 112, 241–245) experiment for the GD3-FCHASE sample. The nano-NMR probe which is a high-resolution magic angle spinning probe produces high resolution spectra of liquid samples dissolved in only 40 μL (Manzi et al. (1995) *J. Biol. Chem.* 270, 9154–9163). The GD3-FCHASE sample (mass=1486.33 Da) was prepared by lyophilizing the original 0.6 mL sample (200 nanomoles) and dissolving it in 40 μL of $D_2O$ for a final concentration of 5 mM. The final pH of the sample could not be measured.

The gradient HMBC experiment was done at a spin rate of 2990 Hz, 400 increments of 1024 complex points, 128 scans per increment, acquisition time of 0.21 s, $^1J(C, H)=140$ Hz and $^nJ(C, H)=8$ Hz, for a duration of 18.5 h.

Mass Spectrometry

All mass measurements were obtained using a Perkin-Elmer Biosystems (Fragmingham, Mass.) Elite-STR MALDI-TOF instrument. Approximately two μg of each oligosaccharide was mixed with a matrix containing a saturated solution of dihydroxybenzoic acid. Positive and negative mass spectra were acquired using the reflector mode.

Results

Defection of Glycosyltransferase Activities in C. jejuni Strains

Before the cloning of the glycosyltransferase genes, we examined C. jejuni OH4384 and NCTC 11168 cells for various enzymatic activities. When an enzyme activity was detected, the assay conditions were optimized (described in the Experimental Procedures) to ensure maximal activity. The capillary electrophoresis assay we employed was extremely sensitive and allowed detection of enzyme activity in the μU/ml range (Gilbert et al. (1996) J. Biol. Chem. 271: 28271–28276). We examined both the sequenced strain NCTC 11168 and the GBS-associated strain OH4384 for the enzymes required for the GT1a ganglioridemimic synthesis. As predicted, strain OH4384 possessed the enzyme activities required for the synthesis of this structure: β-1,4-N-acetylgalactosaminyltransferase, β-1,3-galactosyltransferase, α-2,3-sialyltransferase and α-2,8-sialyltransferase. The genome of the strain, NCTC 11168 lacked the β-1,3-galactosyltransferase and the α-2,8-sialyltransferase activities.

Cloning of an α-2,3-Sialyltransferase (cst-I) Using an Activity Screening Strategy A plasmid library made from an unfractionated partial HindIII digestion of chromosomal DNA from C. jejuni OH4384 yielded 2,600 white colonies which were picked to form pools of 100. We used a "divide and conquer" screening protocol from which two positive clones were obtained and designated pCJH9 (5.3 kb insert, 3 HindIII sites) and pCJH101 (3.9 kb insert, 4 HindIII sites). Open reading frame (ORF) analysis and PCR reactions with C. jejuni OH4384 chromosomal DNA indicated that pCJH9 contained inserts that were not contiguous in the chromosomal DNA. The sequence downstream of nucleotide #1440 in pCJH9 was not further studied while the first 1439 nucleotides were found to be completely contained within the sequence of pCJH101. The ORF analysis and PCR reactions with chromosomal DNA indicated that all of the pCJH101 HindIII fragments were contiguous in C. jejuni OH4384 chromosomal DNA.

Four ORFs, two partial and two complete, were found in the sequence of pCJH101 (FIG. 2). The first 812 nucleotides encode a polypeptide that is 69% identical with the last 265 a.a. residues of the peptide chain release factor RF-2 (prfB gene, GenBank #AE000537) from Helicobacter pylori. The last base of the TAA stop codon of the chain release factor is also the first base of the ATG start codon of an open reading frame that spans nucleotides #812 to #2104 in pCJH101. This ORF was designated cst-I (Campylobacter sialyltransferase I) and encodes a 430 amino acid polypeptide that is homologous with a putative ORF from Haemophilus influenzae (GenBank #U32720). The putative H. influenzae ORF encodes a 231 amino acid polypeptide that is 39% identical to the middle region of the Cst I polypeptide (amino acid residues #80 to #330). The sequence downstream of cst-I includes an ORF and a partial ORF that encode polypeptides that are homologous (>60% identical) with the two subunits, CysD and CysN, of the E. coli sulfate adenylyltransferase (GenBank #AE000358).

In order to confirm that the cst-I ORF encodes sialyltransferase activity, we sub-cloned it and over-expressed it in E. coli. The expressed enzyme was used to add sialic acid to Gal-β-1,4-Glc-β-FCHASE (Lac-FCHASE). This product (GM3-FCHASE) was analyzed by NMR to confirm the Neu5Ac-α-2,3-Gal linkage specificity of Cst-I.

Sequencing of the LOS Biosynthesis Locus of C. jejuni OH4384

Analysis of the preliminary sequence data available at the website of the C. jejuni NCTC 11168 sequencing group (Sanger Centre, UK revealed that the two heptosyltransferases involved in the synthesis of the inner core of the LPS were readily identifiable by sequence homology with other bacterial heptosyltransferases. The region between the two heptosyltransferases spans 13.49 kb in NCTC 11168 and includes at least seven potential glycosyltransferases based on BLAST searches in GenBank. Since no structure is available for the LOS outer core of NCTC 11168, it was impossible to suggest functions for the putative glycosyltransferase genes in that strain.

Based on conserved regions in the heptosyltransferases sequences, we designed primers (CJ-42 and CJ-43) to amplify the region between them. We obtained a PCR product of 13.49 kb using chromosomal DNA from C. jejuni NCTC 11168 and a PCR product of 11.47 kb using chromosomal DNA from C. jejuni OH4384. The size of the PCR product from strain NCTC 11168 was consistent with the Sanger Centre data. The smaller size of the PCR product from strain OH4384 indicated heterogeneity between the strains in the region between the two heptosyltransferase genes and suggested that the genes for some of the glycosyltransferases specific to strain OH4384 could be present in that location. We sequenced the 11.47 kb PCR product using a combination of primer walking and sub-cloning of HindIII fragments (GenBank #AF130984). The G/C content of the DNA was 27%, typical of DNA from Campylobacter. Analysis of the sequence revealed eleven complete ORFs in addition to the two partial ORFs encoding the two heptosyltransferases (FIG. 2, Table 3). When comparing the deduced amino acid sequences, we found that the two strains share six genes that are above 80% identical and four genes that are between 52 and 68% identical (Table 3). Four genes are unique to C. jejuni NCTC 11168 while one gene is unique to C. jejuni OH4384 (FIG. 2). Two genes that are present as separate ORFs (ORF #5a and #10a) in C. jejuni OH4384 are found in an in-frame fusion ORF (#5b/10b) in C. jejuni NCTC 1168.

TABLE 3

Location and description of the ORFs of the LOS biosynthesis locus from *C. jejuni* OH4384

| ORF # | Location | Homologue in Strain NCTC11168[a] (% identity in the a.a. sequence) | Homologues found in GenBank (% identity in the a.a sequence) | Function[b] |
|---|---|---|---|---|
| 1a | 1–357 | ORF #1b (98%) | rfaC (GB #AE000546) from *Helicobacter pylori* (35%) | Heptosyltransferase I |
| 2a | 350–1,234 | ORF #2b (96%) | waaM (GB #AE001463) from *Helicobacter pylori* (25%) | Lipid A biosynthesis acyltransferase |
| 3a | 1,234–2,487 | ORF #3b (90%) | lgtF (GB #U58765) from *Neisseria meningitidis* (31%) | Glycosyltransferase |
| 4a | 2,786–3,952 | ORF #4b (80%) | cps14J (GB #X85787) from *Streptococcus pneumoniae* (45% over first 100 a.a) | Glycosyltransferase |
| 5a | 4,025–5,065 | N-terminus of ORF #5b/10b (52%) | ORF #HP0217 (GB #AE000541) from *Helicobacter pylori* (50%) | β-1,4-N-acetylgalactosaminyltransferase (cgtA) |
| 6a | 5,057–5,959 (complement) | ORF #6b (60%) | cps23FU (GB #AF030373) from *Streptococcus pneumoniae* (23%) | β-1,3-Galactosyltransferase (cgtB) |
| 7a | 6,048–6,920 | ORF #7b (52%) | ORF #HI0352 (GB #U32720) from *Haemophilus influenzae* (40%) | Bi-functional α-2,3/α2,8 sialyltransferase (cst-II) |
| 8a | 6,924–7,961 | ORF #8b (80%) | siaC (GB #U40740) from *Neisseria meningitidis* (56%) | Sialic acid synthase |
| 9a | 8,021–9,076 | ORF #9b (80%) | siaA (GB #M95053) from *Neisseria meningitidis* (40%) | Sialic acid biosynthesis |
| 10a | 9,076–9,738 | C-terminus of ORF #5b/10b (68%) | neuA (GB #U54496) from *Haemophilus ducreyi* (39%) | CMP-sialic acid synthetase |
| 11a | 9,729–10,559 | No homologue | Putative ORF (GB #AF010496) from *Rhodobacter capsulatus* (22%) | Acetyltransferase |
| 12a | 10,557–11,366 (complement) | ORF #12b (90%) | ORF #HI0868 (GB #U32768) from *Haemophilus influenzae* (23%) | Glycosyltransferase |
| 13a | 11,347–11,474 | ORF #13b (100%) | rfaF (GB #AE000625) from *Helicobacter pylori* (60%) | Heptosyltransferase II |

[a]The sequence of the *C. jejuni* NCTC 11168 ORFs can be obtained from the Sanger Centre.
[b]The functions that were determined experimentally are in bold fonts. Other functions are based on higher score homologues from GenBank.

Identification of Outer Core Glycosyltransferases

Various constructs were made to express each of the potential glycosyltransferase genes located between the two heptosyltransferases from *C. jejuni* OH4384. The plasmid pCJL-09 contained the ORF #5a and a culture of this construct showed GalNAc transferase activity when assayed using GM3-FCHASE as acceptor. The GalNAc transferase was specific for a sialylated acceptor since Lac-FCHASE was a poor substrate (less than 2% of the activity observed with GM3-FCHASE). The reaction product obtained from GM3-FCHASE had the correct mass as determined by MALDI-TOF mass spectrometry, and the identical elution time in the CE assay as the GM2-FCHASE standard. Considering the structure of the outer core LPS of *C. jejuni* OH4384, this GalNAc transferase (cgtA for Camplyobacter glycosyltransferase A), has a β-1,4-specificity to the terminal Gal residue of GM3-FCHASE. The linkage specificity of CgtA was confirmed by the NMR analysis of GM2-FCHASE (see text below, Table 4). The in vivo role of cgtA in the synthesis of a GM2 mimic is confirmed by the natural knock-out mutant provided by C. jejuni OH4382 (FIG. 1). Upon sequencing of the cgtA homologue from C. jejuni OH4382 we found a frame-shift mutation (a stretch of seven A's instead of 8 A's after base #71) which would result in the expression of a truncated cgtA version (29 aa instead of 347 aa). The LOS outer core structure of C. jejuni OH4382 is consistent with the absence of β-1,4-GlaNAc transferase as the inner galactose residue is substituted with sialic acid only (Aspinall et al. (1994) *Biochemistry* 33, 241–249).

The plasmid pCJL-04 contained the ORF #6a and an IPTG-induced culture of this construct showed galactosyltansferase activity using GM2-FCHASE as an acceptor thereby producing GM1a-FCHASE. This product was sensitive to β-1,3-galactosidase and was found to have the correct mass by MALDI-TOF mass spectrometry. Considering the structure of the LOS outer core of C. jejuni OH4384, we suggest that this galactosyltransferase (cgtB for Campylobacter glycosyltransferase B) has β-1,3-specificity to the terminal GalNAc residue of GM2-FCHASE. The linkage specificity of CgtA was confirmed by the NMR analysis of GM1a-FCHASE (see text below, Table 4) which was synthesized by using sequentially Cst-I, CgtA and CgtB.

The plasmid pCJL-03 included the ORF #7a and an IPTG-induced culture showed sialyltransferase activity using both Lac-FCHASE and GM3-FCHASE as acceptors. This second sialyltransferase from OH4384 was designated cst-II. Cst-II was shown to be bi-functional as it could transfer sialic acid α-2,3 to the terminal Gal of Lac-FCHASE and also α-2,8- to the terminal sialic acid of GM3-FCHASE. NMR analysis of a reaction product formed with Lac-FCHASE confirmed the α-2,3-linkage of the first slalic acid on the Gal, and the α-2,8-linkage of the second sialic acid (see text below, Table 4).

TABLE 4

Proton NMR chemical shifts[a] for the fluorescent derivatives of the ganglioside mimics synthesized using the cloned glycosyltransferases.

| Residue | H | Lac- | GM3- | GM2- | GM1a- | GD3- |
|---|---|---|---|---|---|---|
| βGlc a | 1 | 4.57 | 4.70 | 4.73 | 4.76 | 4.76 |
| | 2 | 3.23 | 3.32 | 3.27 | 3.30 | 3.38 |
| | 3 | 3.47 | 3.54 | 3.56 | 3.58 | 3.57 |
| | 4 | 3.37 | 3.48 | 3.39 | 3.43 | 3.56 |
| | 5 | 3.30 | 3.44 | 3.44 | 3.46 | 3.50 |
| | 6 | 3.73 | 3.81 | 3.80 | 3.81 | 3.85 |
| | 6' | 3.22 | 3.38 | 3.26 | 3.35 | 3.50 |
| βGal(1-4) b | 1 | 4.32 | 4.43 | 4.42 | 4.44 | 4.46 |
| | 2 | 3.59 | 3.60 | 3.39 | –3.39 | 3.60 |
| | 3 | 3.69 | 4.13 | 4.18 | 4.18 | 4.10 |
| | 4 | 3.97 | 3.99 | 4.17 | 4.17 | 4.00 |
| | 5 | 3.81 | 3.77 | 3.84 | 3.83 | 3.78 |
| | 6 | 3.86 | 3.81 | 3.79 | 3.78 | 3.78 |
| | 6' | 3.81 | 3.78 | 3.79 | 3.78 | 3.78 |
| αNeu5Ac(2-3) c | 3$_{ax}$ | | 1.81 | 1.97 | 1.96 | 1.78 |
| | 3$_{eq}$ | | 2.76 | 2.67 | 2.68 | 2.67 |
| | 4 | | 3.69 | 3.78 | 3.79 | 3.60 |
| | 5 | | 3.86 | 3.84 | 3.83 | 3.82 |
| | 6 | | 3.65 | 3.49 | 3.51 | 3.68 |
| | 7 | | 3.59 | 3.61 | 3.60 | 3.87 |
| | 8 | | 3.91 | 3.77 | 3.77 | 4.15 |
| | 9 | | 3.88 | 3.90 | 3.89 | 4.18 |
| | 9' | | 3.65 | 3.63 | 3.64 | 3.74 |
| | NAc | | 2.03 | 2.04 | 2.03 | 2.07 |

TABLE 4-continued

Proton NMR chemical shifts[a] for the fluorescent derivatives of the ganglioside mimics synthesized using the cloned glycosyltransferases.

| Residue | H | Lac- | GM3- | GM2- | GM1a- | GD3- |
|---|---|---|---|---|---|---|
| βGalNAc(1-4) d | 1 | | | 4.77 | 4.81 | |
| | 2 | | | 3.94 | 4.07 | |
| | 3 | | | 3.70 | 3.82 | |
| | 4 | | | 3.93 | 4.18 | |
| | 5 | | | 3.74 | 3.75 | |
| | 6 | | | 3.86 | 3.84 | |
| | 6' | | | 3.86 | 3.84 | |
| | NAc | | | 2.04 | 2.04 | |
| βGal(1-3) e | 1 | | | | 4.55 | |
| | 2 | | | | 3.53 | |
| | 3 | | | | 3.64 | |
| | 4 | | | | 3.92 | |
| | 5 | | | | 3.69 | |
| | 6 | | | | 3.78 | |
| | 6' | | | | 3.74 | |
| αNeu5Ac(2-8) f | 3$_{ax}$ | | | | | 1.75 |
| | 3$_{eq}$ | | | | | 2.76 |
| | 4 | | | | | 3.66 |
| | 5 | | | | | 3.82 |
| | 6 | | | | | 3.61 |
| | 7 | | | | | 3.58 |
| | 8 | | | | | 3.91 |
| | 9 | | | | | 3.88 |
| | 9' | | | | | 3.64 |
| | NAc | | | | | 2.02 |

[a]in ppm from HSQC spectrum obtained at 600 MHz, D$_2$O, pH 7, 28° C. for Lac-, 25° C. for GM3-, 16° C. for GM2-, 24° C. for GM1a-, and 24° C. GD3-FCHASE. The methyl resonance of internal acetone is at 2.225 ppm ($^1$H). The error is ±0.02 ppm for $^1$H chemical shifts and ±5° C. for the sample temperature. The error is ±0.1 ppm for the H-6 resonances of residue a, b, d and e due to overlap.

Comparison of the Sialyltransferases

The in vivo role of cst-II from C. jejuni OH4384 in the synthesis of a tri-sialylated Gt1a ganglioside mimic is supported by comparison with the cst-II homologue from C. jejuni O:19 (serostrain) that expresses the di-sialylated GD1a ganglioside mimic. There are 24 nucleotide differences that translate into 8 amino acid differences between these two cst-II homologues (FIG. 3). When expressed in E. coli, the cst-II homologue from C. jejuni O:19 (serostrain) has α-2,3-sialyltransferase activity but very low α-2,8-sialyltransferase activity (Table 5) which is consistent with the absence of terminal α-2,8-linked sialic acid in the LOS outer core (Aspinall et al. (1994) *Biochemistry* 33, 241–249) of C. jejuni O:19 (serostrain). The cst-II homologue from C. jejuni NCTC 11168 expressed much lower α-2,3-sialyltransferase activity than the homologues from O:19 (serostrain) or OH4384 and no detectable α-2,8-sialyltransferase activity. We could detect an IPTG-inducible band on a SDS-PAGE gel when cst-II from NCTC 11168 was expressed in E. coli (data not shown). The Cst-II protein from NCTC 11168 shares only 52% identity with the homologues from O:19 (serostrain) or OH4384. We could not determine whether the sequence differences could be responsible for the lower activity expressed in E. coli.

Although cst-I mapped outside the LOS biosynthesis locus, it is obviously homologous to cst-II since its first 300 residues share 44% identity with Cst-II from either C. jejuni OH4384 or C. jejuni NCTC 11168 (FIG. 3). The two Cst-II homologues share 52% identical residues between themselves and are missing the C-terminal 130 amino acids of Cst-I. A truncated version of Cst-I which was missing 102 amino acids at the C-terminus was found to be active (data not shown) which indicates that the C-terminal domain of Cst-I is not necessary for sialyltransferase activity. Although the 102 residues at the C-terminus are dispensable for in vitro enzymatic activity, they may interact with other cell components in vivo either for regulatory purposes or for proper cell localization. The low level of conservation between the *C. jejuni* sialyltransferases is very different from what was previously observed for the α-2,3-sialyltransferases from *N. meningitidis* and *N. gonorrhoeae*, where the 1st transferases are more than 90% identical at the protein level between the two species and between different isolates of the same species (Gilbert et al., supra.).

TABLE 5

Comparison of the activity of the sialyltransferases from *C. jejuni*. The various sialyltransferases were expressed in *E. coli* as fusion proteins with the maltose-binding protein in the vector pCWori+ (Wakarchuk et al. (1994) Protein. Sci. 3, 467–475). Sonicated extracts were assayed using 500 μM of either Lac-FCHASE or GM3-FCHASE.

| Sialyltransferase gene | Activity (μU/mg)[a] | | |
|---|---|---|---|
| | Lac-FCHASE | GM3-FCHASE | Ratio (%)[b] |
| cst-I (OH4384) | 3,744 | 2.2 | 0.1 |
| cst-II (OH4384) | 209 | 350.0 | 167.0 |
| cst-II (O:19 serostrain) | 2,084 | 1.5 | 0.1 |
| cst-II (NCTC 11168) | 8 | 0 | 0.0 |

[a]The activity is expressed in μU (pmol of product per minute) per mg of total protein in the extract.
[b]Ratio (in percentage) of the activity on GM3-FCHASE divided by the activity on Lac-FCHASE.

NMR Analysis on Nanomole Amounts of the Synthesized Model Compounds.

In order to properly assess the linkage specificity of an identified glycosyltransferase, its product was analyzed by NMR spectroscopy. In order to reduce the time needed for the purification of the enzymatic products, NMR analysis was conducted on nanomole amounts. All compounds are soluble and give sharp resonances with linewidths of a few Hz since the H-1 anomeric doublets ($J_{1,2}$=8 Hz) are well resolved. The only exception is for GM2-FCHASE which has broad lines (~10 Hz), probably due to aggregation. For the proton spectrum of the 5 mM GD3-FCHASE solution in the nano-NMR probe, the linewidths of the anomeric signals were on the order of 4 Hz, due to the increased concentration. Also, additional peaks were observed, probably due to degradation of the sample with time. There were also some slight chemical shifts changes, probably due to a change in pH upon concentrating the sample from 0.3 mM to 5 mM. Proton spectra were acquired at various temperatures in order to avoid overlap of the HDO resonance with the anomeric resonances. As can be assessed from the proton spectra, all compounds were pure and impurities or degradation products that were present did not interfere with the NMR analysis which was performed as previously described (Pavliak et al. (1993) *J. Biol. Chem.* 268, 14146–14152; Brisson et al. (1997) *Biochemistry* 36, 3278–3292).

For all of FCHASE glycosides, the $^{13}$C assignments of similar glycosides (Sabesan and Paulson (1986) *J. Am. Chem. Soc.* 108, 2068–2080; Michon et al. (1987) *Biochemistry* 26, 8399–8405; Sabesan et al. (1984) *Can. J. Chem.* 62, 1034–1045) were available. For the FCHASE glycosides, the $^{13}$C assignments were verified by first assigning the proton spectrum from standard homonuclear 2D experiments, COSY, TOCSY and NOESY, and then verifying the $^{13}$C assignments from an HSQC experiment, which detects C—H correlations. The HSQC experiment does not detect quaternary carbons like C-1 and C-2 of sialic acid, but the HMBC experiment does. Mainly for the Glc resonances, the proton chemical shifts obtained from the HSQC spectra differed from those obtained from homonuclear experiments due to heating of the sample during $^{13}$C decoupling. From a series of proton spectrum acquired at different temperatures, the chemical shifts of the Glc residue were found to be the most sensitive to temperature. In all compounds, the H-1 and H-2 resonances of Glc changed by 0.004 ppm/° C., the Gal(1-4) H-1 by 0.002 ppm/° C., and less than 0.001 ppm/° C. for the Neu5Ac H-3 and other anomeric resonances. For LAC-FCHASE, the Glc H-6 resonance changed by 0.008 ppm/° C.

The large temperature coefficient for the Glc resonances is attributed to ring current shifts induced by the linkage to the aminophenyl group of FCHASE. The temperature of the sample during the HSQC experiment was measured from the chemical shift of the Glc H-1 and H-2 resonances. For GM1a-FCHASE, the temperature changed from 12° C. to 24° C. due to the presence of the Na+ counterion in the solution and NaOH used to adjust the pH. Other samples had less severe heating (<5° C.). In all cases, changes of proton chemical shifts with temperature did not cause any problems in the assignments of the resonances in the HSQC spectrum. In Table 4 and Table 6, all the chemical shifts are taken from the HSQC spectra.

The linkage site on the aglycon was determined mainly from a comparison of the $^{13}$C chemical shifts of the enzymatic product with those of the precursor to determine glycosidation shifts as done previously for ten sialyloligosaccharides (Salloway et al. (1996) *Infect. Immun.* 64, 2945–2949). Here, instead of comparing $^{13}$C spectra, HSQC spectra are compared, since one hundred times more material would be needed to obtain a $^{13}$C spectrum. When the $^{13}$C chemical shifts from HSQC spectra of the precursor compound are compared to those of the enzymatic product, the main downfield shift always occurs at the linkage site while other chemical shifts of the precursor do not change substantially. Proton chemical shift differences are much more susceptible to long-range conformational effects, sample preparation, and temperature. The identity of the new sugar added can quickly be identified from a comparison of its $^{13}$C chemical shifts with those of monosaccharides or any terminal residue, since only the anomeric chemical shift of the lycon changes substantially upon glycosidation (Sabesan and Paulson, supra.).

Vicinal proton spin-spin coupling ($J_{HH}$) obtained from 1D TOCSY or 1D NOESY experiments also are used to determine the identity of the sugar. NOE experiments are done to sequence the sugars by the observation of NOEs between the anomeric glycon protons (H-3s for sialic acid) and the aglycon proton resonances. The largest NOE is usually on the linkage proton but other NOEs can also occur on aglycon proton resonances that are next to the linkage site. Although at 600 MHz, the NOEs of many tetra- and pentasaccharides are positive or very small, all these compounds gave good negative NOEs with a mixing time of 800 ms, probably due to the presence of the large FCHASE moiety.

For the synthetic Lac-FCHASE, the $^{13}$C assignments for the lactose moiety of Lac-FCHASE were confirmed by the 2D methods outlined above. All the proton resonances of the Glc unit were assigned from a 1D-TOCSY experiment on the H-1 resonance of Glc with a mixing time of 180 ms. A 1D-TOCSY experiment for Gal H-1 was used to assign the H-1 to H-4 resonances of the Gal unit. The remaining H-5 and H-6s of the Gal unit were then assigned from the HSQC experiment. Vicinal spin-spin coupling values ($J_{HH}$) for the sugar units were in accord with previous data (Michon et al., supra.). The chemical shifts for the FCHASE moiety have been given previously (Gilbert et al. (1996) *J. Biol. Chem.* 271, 28271–28276).

Accurate mass determination of the enzymatic product of Cst-I from Lac-FCHASE was consistent with the addition of sialic acid to the Lac-FCHASE acceptor (FIG. 4). The product was identified as GM3-FCHASE since the proton spectrum and $^{13}C$ chemical shifts of the sugar moiety of the product (Table 6) were very similar to those for the GM3 oligosaccharide or sialyllactose, (αNeu5Ac(2-3)βGal(1-4)βGlc; Sabesan and Paulson, supra.). The proton resonances of GM3-FCHASE were assigned from the COSY spectrum, the HSQC spectrum, and comparison of the proton and $^{13}C$ chemical shifts with those of αNeu 5Ac(2-3)βGal(1-4)βGlcNAc-FCHASE (Gilbert et al., supra.). For these two compounds, the proton and $^{13}C$ chemical shifts for the Neu5Ac and Gal residues were within error bounds of each other (Id.). From a comparison of the HSQC spectra of Lac-FCHASE and GM3-FCHASE, it is obvious that the linkage site is at Gal C-3 due to the large downfield shift for Gal H-3 and Gal C-3 upon sialylation typical for (2-3) sialyloligosaccharides (Sabesan and Paulson, supra.). Also, as seen before for αNeu5Ac(2-3)βGal(1-4)βGlcNAc-FCHASE (Gilbert et al., supra.), the NOE from H-3$_{ax}$ of sialic acid to H-3 of Gal was observed typical of the αNeu5Ac(2-3)Gal linkage.

TABLE 6

Comparison of the $^{13}C$ chemical shifts for the FCHASE glycosides[a] with those observed for lactose[b] (Sabesan and Paulson, supra.), ganglioside oligosaccharides[b] (Id., Sabesan et al. (1984) Can. J. Chem. 62, 1034–1045) and (-8NeuAc2-)$_3$ (Michon et al. (1987) Biochemistry 26, 8399–8405). The chemical shifts at the glycosidation sites are underlined.

| Residue | C | Lac- | Lactose | GM3- | GM3OS | GM2- | GM2OS | GM1a- | GM1aOS | GD3- | 8NeuAc2 |
|---|---|---|---|---|---|---|---|---|---|---|---|
| βGlc | 1 | 100.3 | 96.7 | 100.3 | 96.8 | 100.1 | 96.6 | 100.4 | 96.6 | 100.6 | |
| a | 2 | 73.5 | 74.8 | 73.4 | 74.9 | 73.3 | 74.6 | 73.3 | 74.6 | 73.5 | |
| | 3 | 75.2 | 75.3 | 75.0 | 75.4 | 75.3 | 75.2 | 75.0 | 75.2 | 75.0 | |
| | 4 | <u>79.4</u> | <u>79.4</u> | <u>79.0</u> | <u>79.4</u> | <u>79.5</u> | <u>79.5</u> | <u>79.5</u> | <u>79.5</u> | <u>78.8</u> | |
| | 5 | 75.9 | 75.7 | 75.7 | 75.8 | 75.8 | 75.6 | 75.7 | 75.6 | 75.8 | |
| | 6 | 61.1 | 61.1 | 60.8 | 61.2 | 61.0 | 61.0 | 60.6 | 61.0 | 60.8 | |
| βGal(1-4) | 1 | 104.1 | 103.8 | 103.6 | 103.7 | 103.6 | 103.5 | 103.6 | 103.5 | 103.6 | |
| b | 2 | 72.0 | 71.9 | 70.3 | 70.4 | 71.0 | 70.9 | 70.9 | 70.9 | 70.3 | |
| | 3 | 73.5 | 73.5 | <u>76.4</u> | <u>76.6</u> | <u>75.3</u> | <u>75.6</u>[c] | <u>75.1</u> | <u>75.2</u>[c] | <u>76.3</u> | |
| | 4 | 69.7 | 69.5 | 68.4 | 68.5 | <u>78.3</u> | <u>78.0</u>[c] | <u>78.1</u> | <u>78.0</u>[c] | 68.5 | |
| | 5 | 76.4 | 76.3 | 76.0 | 76.2 | 75.0 | 74.9 | 74.9 | 75.0 | 76.1 | |
| | 6 | 62.1 | 62.0 | 62.1 | 62.0 | 62.2 | 61.4 | 62.0 | 61.5 | 62.0 | |
| αNeu5Ac | 3 | | | 40.4 | 40.7 | 37.7 | 37.9 | 37.8 | 37.9 | 40.4 | 41.7 |
| (2-3) | 4 | | | 69.2 | 69.3 | 69.8 | 69.5 | 69.5 | 69.5 | 69.0 | 68.8[d] |
| c | 5 | | | 52.6 | 52.7 | 52.7 | 52.5 | 52.6 | 52.5 | 53.0 | 53.2 |
| | 6 | | | 73.7 | 73.9 | 74.0 | 73.9 | 73.8 | 73.9 | 74.9 | 74.5[d] |
| | 7 | | | 69.0 | 69.2 | 69.0 | 68.8 | 69.0 | 68.9 | 70.3 | 70.0 |
| | 8 | | | 72.6 | 72.8 | 73.3 | 73.1 | 73.1 | 73.1 | <u>79.1</u> | <u>79.1</u> |
| | 9 | | | 63.4 | 63.7 | 63.9 | 63.7 | 63.7 | 63.7 | 62.5 | 62.1 |
| | NAc | | | 22.9 | 23.1 | 23.2 | 22.9 | 23.3 | 22.9 | 23.2 | 23.2 |
| βGalNAc | 1 | | | | | 103.8 | 103.6 | 103.4 | 103.4 | | |
| (1-4) | 2 | | | | | 53.2 | 53.2 | 52.0 | 52.0 | | |
| d | 3 | | | | | 72.3 | 72.2 | <u>81.4</u> | <u>81.2</u> | | |
| | 4 | | | | | 68.8 | 68.7 | 68.9 | 68.8 | | |
| | 5 | | | | | 75.6 | 75.2 | 75.1 | 75.2 | | |
| | 6 | | | | | 61.8 | 62.0 | 61.5 | 62.0 | | |
| | NAc | | | | | 23.2 | 23.5 | 23.4 | 23.5 | | |
| βGal(1-3) | 1 | | | | | | | 105.5 | 105.6 | | |
| e | 2 | | | | | | | 71.5 | 71.6 | | |
| | 3 | | | | | | | 73.1 | 73.4 | | |
| | 4 | | | | | | | 69.5 | 69.5 | | |
| | 5 | | | | | | | 75.7 | 75.8 | | |
| | 6 | | | | | | | 61.9 | 61.8 | | |
| αNeu5Ac | 3 | | | | | | | | | 41.2 | 41.2 |
| (2-8) | 4 | | | | | | | | | 69.5 | 69.3 |
| f | 5 | | | | | | | | | 53.0 | 52.6 |
| | 6 | | | | | | | | | 73.6 | 73.5 |
| | 7 | | | | | | | | | 69.0 | 69.0 |
| | 8 | | | | | | | | | 72.7 | 72.6 |
| | 9 | | | | | | | | | 63.5 | 63.4 |
| | NAc | | | | | | | | | 23.0 | 23.1 |

[a]in ppm from the HSQC spectrum obtained at 600 MHz, $D_2O$, pH 7, 28° C. for Lac-, 25° C. for GM3-, 16° C. for GM2-, 24° C. for GM1a-, and 24° C. GD3-FCHASE. The methyl resonance of internal acetone is at 31.07 ppm relative to external dioxane at 67.40 ppm. The error is ±0.2 ppm for $^{13}C$ chemical shifts and ±5° C. for the sample temperature. The error is ±0.8 ppm for 6a, 6b, 6d, 6e due to overlap.
[b]A correction of +0.52 ppm was added to the chemical shifts of the reference compounds (25, 27) to make them relative to dioxane set at 67.40 ppm. Differences of over 1 ppm between the chemical shifts of the FCHASE compound and the corresponding reference compound are indicated in bold.
[c]C-3 and C-4 assignments have been reversed.
[d]C-4 and C-6 assignments have been reversed.

Accurate mass determination of the enzymatic product of Cst-II from Lac-FCHASE indicated that two sialic acids had been added to the Lac-FCHASE acceptor (FIG. 4). The proton resonances were assigned from COSY, 1D TOCSY and 1D NOESY and comparison of chemical shifts with known structures. The Glc H-1 to H-6 and Gal H-1 to H-4 resonances were assigned from 1D TOCSY on the H-1 resonances. The Neu5Ac resonances were assigned from COSY and confirmed by 1D NOESY. The 1D NOESY of the H-8, H-9Neu5Ac resonances at 4.16 ppm was used to locate the H-9s and H-7 resonances (Michon et al, supra.). The singlet appearance of the H-7 resonance of Neu5Ac(2-3) arising from small vicinal coupling constants is typical of the 2-8 linkage (Id.). The other resonances were assigned from the HSQC spectrum and $^{13}$C assignments for terminal sialic acid (Id.). The proton and $^{13}$C carbon chemical shifts of the Gal unit were similar to those in GM3-FCHASE, indicating the presence of the αNeu5Ac(2-3)Gal linkage. The $J_{HH}$ values, proton and $^{13}$C chemical shifts of the two sialic acids were similar to those of αNeu5Ac(2-8)Neu5Ac in the α(2-8)-linked Neu5Ac trisaccharide (Salloway et al. (1996) Infect. Immun. 64, 2945–2949) indicating the presence of that linkage. Hence, the product was identified as GD3-FCHASE. Sialylation at C-8 of Neu5Ac caused a downfield shift of −6.5 ppm in its C-8 resonance from 72.6 ppm to 79.1 ppm.

The inter-residue NOEs for GD3-FCHASE were also typical of the αNeu5Ac(2-8)αNeu5Ac(2-3)βGal sequence. The largest inter-residue NOEs from the two H-3$_{ax}$ resonances at 1.7–1.8 ppm of Neu5Ac(2-3) and Neu5Ac(2-8) are to the Gal H-3 and -8)Neu5Ac H-8 resonances. Smaller inter-residue NOEs to Gal H-4 and -8)Neu5Ac H-7 are also observed. NOEs on FCHASE resonances are also observed due the overlap of an FCHASE resonance with the H-3$_{ax}$ resonances (Gilbert et al., supra.). The inter-residue NOE from H-3$_{eq}$ of Neu5Ac(2-3) to Gal H-3 is also observed. Also, the intra-residues confirmed the proton assignments. The NOEs for the 2–8 linkage are the same as those observed for the -8Neu5Acα2- polysaccharide (Michon et al., supra.).

The sialic acid glycosidic linkages could also be confirmed by the use of the HMBC experiment which detects $^3$J(C, H) correlations across the glycosidic bond. The results for both α-2,3 and α-2,8 linkages indicate the $^3$J(C, H) correlations between the two Neu5Ac anomeric C-2 resonances and Gal H-3 and -8)Neu5Ac H-8 resonances. The intra-residue correlations to the H-3$_{ax}$ and H-3$_{eq}$ resonances of the two Neu5Ac residues were also observed. The Glc (C-1, H-2) correlation is also observed since there was partial overlap of the crosspeaks at 101 ppm with the crosspeaks at 100.6 ppm in the HMBC spectrum.

Accurate mass determination of the enzymatic product of CgtA from GM3-FCHASE indicated that a N-acetylated hexose unit had been added to the GM3-FCHASE acceptor (FIG. 4). The product was identified as GM2-FCHASE since the glycoside proton and $^{13}$C chemical shifts were similar to those for GM2 oligosaccharide (GM2OS) (Sabesan et al. (1984) Can. J. Chem. 62, 1034–1045). From the HSQC spectrum for GM2-FCHASE and the integration of its proton spectrum, there are now two resonances at 4.17 ppm and 4.18 ppm along with a new anomeric "d1" and two NAc groups at 2.04 ppm. From TOCSY and NOESY experiments, the resonance at 4.18 ppm was unambiguously assigned to Gal H-3 because of the strong NOE between H-1 and H-3. For βgalactopyranose, strong intra-residue NOEs between H-1 and H-3 and H-1 and H-5 are observed due to the axial position of the protons and their short interproton distances (Pavliak et al. (1993) J. Biol. Chem. 268, 14146–14152; Brisson et al. (1997) Biochemistry 36, 3278–3292; Sabesan et al. (1984) Can. J. Chem. 62, 1034–1045). From the TOCSY spectrum and comparison of the H1 chemical shifts of GM2-FCHASE and GM2OS (Sabesan et al., supra.) the resonance at 4.17 ppm is assigned as Gal H-4. Similarly, from TOCSY and NOESY spectra, the H-1 to H-5 of GalNAc and Glc, and H-3 to H-6 of Neu5Ac were assigned. Due to broad lines, the multiplet pattern of the resonances could not be observed. The other resonances were assigned from comparison with the HSQC spectrum of the precursor and $^{13}$C assignments for GM2OS (Sabesan et al., supra.). By comparing the HSQC spectra for GM3- and GM2-FCHASE glycosides, a −9.9 ppm downfield shift between the precursor and the product occurred on the Gal C-4 resonance. Along with intra-residue NOEs to H-3 and H-5 of βGalNAc, the inter-residue NOE from GalNAc H-1 to Gal H-4 at 4.17 ppm was also observed confirming the βGalNAc(1-4)Gal sequence. The observed NOEs were those expected from the conformational properties of the GM2 ganglioside (Sabesan et al., supra.).

Accurate mass determination of the enzymatic product of CgtB from GM2-FCHASE indicated that a hexose unit had been added to the GM2-FCHASE acceptor (FIG. 4). The product was identified as GM1a-FCHASE since the glycoside $^{13}$C chemical shifts were similar to those for the GM1a oligosaccharide (Id.). The proton resonances were assigned from COSY, 1D TOCSY and 1D NOESY. From a 1D TOCSY on the additional "e1" resonance of the product, four resonances with a mutltiplet pattern typical of β-galactopyranose were observed. From a 1D TOCSY and 1D NOESY on the H-1 resonances of βGalNAc, the H-1 to H-5 resonances were assigned. The βGalNAc H-1 to H-4 multiplet pattern was typical of the β-galactopyranosyl configuration, confirming the identity of this sugar for GM2-FCHASE. It was clear that upon glylcosidation, the major perturbations occurred for the βGalNAc resonances, and there was −9.1 ppm downfield shift between the acceptor and the product on the GalNAc C-3 resonance. Also, along with intra-residue NOEs to H-3, H-5 of Gal, an inter-residue NOE from Gal H-1 to GalNAc H-3 and a smaller one to GalNAc H-4 were observed, confirming the βGal(1-3)GalNAc sequence. The observed NOEs were those expected from the conformational properties of the GM1a ganglioside (Sabesan et al., supra.).

There was some discrepancy with the assignment of the C-3 and C-4 βGal(1-4) resonances in GM2OS and GM1OS which are reversed from the published data (Sabesan et al., supra.). Previously, the assignments were based on comparison of $^{13}$C chemical shifts with known compounds. For GM1a-FCHASE, the assignment for H-3 of Gal(1-4) was confirmed by observing its large vicinal coupling, $J_{2,3}$=10 Hz, directly in the HSQC spectrum processed with 2 Hz/point in the proton dimension. The H-4 multiplet is much narrower (<5 Hz) due to the equatorial position of H-4 in galactose (Sabesan et al., supra.). In Table 6, the C-4 and C-6 assignments of one of the sialic acids in (-8Neu5Ac2-)$_3$ also had to be reversed (Michon et al., supra.) as confirmed from the assignments of H-4 and H-6.

The $^{13}$C chemical shifts of the FCHASE glycosides obtained from HSQC spectra were in excellent agreement with those of the reference oligosaccharides shown in Table 6. Differences of over 1 ppm were observed for some resonances and these are due to different aglycons at the reducing end. Excluding these resonances, the averages of the differences in chemical shifts between the FCHASE glycosides and their reference compound were less than ±0.2 ppm. Hence, comparison of proton chemical shifts, $J_{HH}$ values and $^{13}C$ chemical shifts with known structures, and use of NOEs or HMBC were all used to determine the linkage specificity for various glycosyltransferases. The advantage of using HSQC spectra is that the proton assignment can be verified independently to confirm the assignment of the $^{13}C$ resonances of the atoms at the linkage site. In terms of sensitivity, the proton NOEs are the most sensitive, followed by HSQC then HMBC. Using a nano-NMR probe instead of a 5 mm NMR probe on the same amount of material reduced considerably the total acquisition time, making possible the acquisition of an HBMC experiment overnight.

Discussion

In order to clone the LOS glycosyltransferases from C. jejuni, we employed an activity screening strategy similar to that which we previously used to clone the α-2,3-sialyltransferase from Neisseria meningitidis (Gilbert et al., supra.). The activity screening strategy yielded two clones which encoded two versions of the same α-2,3-sialyltransferase gene (cst-I). ORF analysis suggested that a 430 residue polypeptide is responsible for the α-2,3-sialyltransferase activity. To identify other genes involved in LOS biosynthesis, we compared a LOS biosynthesis locus in the complete genome sequence of C. jejuni NCTC 11168 to the corresponding locus from C. jejuni OH4384. Complete open reading frames were identified and analyzed. Several of the open reading frames were expressed individually in E. coli, including a β-1,4-N-acetylgalactosaminyl-transferase (cgtA), a β-1,3-galactosyltransferase (cgtB) and a bifunctional sialyltransferase (cst-II).

The in vitro synthesis of fluorescent derivatives of nanomole amounts of ganglioside mimics and their NMR analysis confirm unequivocally the linkage specificity of the four cloned glycosyltransferases. Based on these data, we suggest that the pathway described in FIG. 4 is used by C. jejuni OH4384 to synthesize a GT1a mimic. This role for cgtA is further supported by the fact that C. jejuni OH4342, which carries an inactive version of this gene, does not have β-1,4-GalNAc in its LOS outer core (FIG. 1). The cst-II gene from C. jejuni OH4384 exhibited both α-2,3- and α-2,8-sialyltransferase in an in vitro assay while cst-II from C. jejuni O:19 (serostrain) showed only α-2,3-sialyltransferase activity (Table 5). This is consistent with a role for cst-II in the addition of a terminal α-2,8-linked sialic acid in C. jejuni OH4382 and OH4384, both of which have identical cst-II genes, but not in C. jejuni O:19 (serostrain, see FIG. 1).

There are 8 amino acid differences between the Cst-II homologues from C. jejuni O:19 (serostrain) and OH4382/84.

The bifunctionality of cst-II might have an impact on the outcome of the C. jejuni infection since it has been suggested that the expression of the terminal di-sialylated epitope might be involved in the development of neuropathic complications such as the Guillain-Barré syndrome (Salloway et al. (1996) Infect. Immun. 64, 2945–2949). It is also worth noting that its bifunctional activity is novel among the sialyltransferases described so far. However, a bifunctional glycosyltransferase activity has been described for the 3-deoxy-D-manno-octulosonic acid transferase from E. coli (Belunis, C. J., and Raetz, C. R. (1992) J. Biol. Chem. 267, 9988–9997).

The mono/bi-functional activity of cst-II and the activation/inactivation of cgtA seem to be two forms of phase variation mechanisms that allow C. jejuni to make different surface carbohydrates that are presented to the host. In addition to those small gene alterations that are found among the three O:19 strains (serostrain, OH4382 and OH4384), there are major genetic rearrangements when the loci are compared between C. jejuni OH4384 and NCTC 11168 (an O:2 strain). Except for the prfB gene, the cst-I locus (including cysN and cysD) is found only in C. jejuni OH4384. There are significant differences in the organization of the LOS biosynthesis locus between strains OH4384 and NCTC 11168. Some of the genes are well conserved, some of them are poorly conserved while others are unique to one or the other strain. Two genes that are present as separate ORFs (#5a: cgtA and #10a: NeuA) in OH4384 are found as an in-frame fusion ORF in NCTC 11168 (ORF #5b/#10b). β-N-acetylgalactosaminyltransferase activity was detected in this strain, which suggests that at least the cgtA part of the fusion may be active.

In summary, this Example describes the identification of several open reading frames that encode enzymes involved in the synthesis of lipooligosaccharides in Campylobacter.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An isolated or recombinantly produced protein comprising a β1,3-galactosyltransferase polypeptide, wherein the β1,3-galactosyltransferase polypeptide has an amino acid sequence that is at least about 95% identical to SEQ ID NO:31.

2. The isolated or recombinantly produced protein of claim 1, wherein the β1,3-galactosyltransferase polypeptide is SEQ ID NO: 31.

3. The isolated or recombinantly produced protein of claim 1, further comprising a tag for purification.

4. The isolated or recombinantly produced protein of claim 1, wherein the protein is recombinantly produced and at least partially purified.

5. The isolated or recombinantly produced protein of claim 1, wherein the protein is expressed by a heterologous host cell.

6. The isolated or recombinantly produced protein of claim 5, wherein the host cell is *E. coli*.

* * * * *

SEQUENCE LISTING

```
<160> NUMBER OF SEQ ID NOS: 49

<210> SEQ ID NO 1
<211> LENGTH: 11474
<212> TYPE: DNA
<213> ORGANISM: Campylobacter jejuni
<220> FEATURE:
<223> OTHER INFORMATION: 11.5 kb PCR product from C. jejuni OH4384
      including LOS biosynthesis locus

<400> SEQUENCE: 1
aaagaatacg aatttgctaa agaggtttta aatcttagtg gtattgatga aacacatata       60
gaattagcgc caaaatttaa tcttgaagag ctaatggctt ttacaaaaat gatggatctt      120
```

-continued

```
atcataggaa atgatagcgg tccaacacat ttagcttttg ctttaaataa agcatctatt      180
acgattttg  gtgcaacacc aagctaccgc aatgcttttc aaactcatat caataaaatc      240
attgatacag gtaaaaaaat ccaaaatgcc aagcatatcg ataaaagtga tttttgtatc      300
acgcgtatag aagaagaaga tatcttcaaa cttgccaaag gcttacttaa tgaaaaatag      360
tgatagaata tatcttagtc tttattatat tttgaaattt tttgttactt ttatgcctga      420
ttgtatcttg catttttag  ctttgattgt agcaagaatc gcttttcatc ttaacaaaaa      480
acaccgcaaa atcatcaata caaatttgca aatctgtttt cctcaataca ctcaaaagga      540
acgcgataaa ttgtctttaa aaatttatga aaattttgct caatttggga ttgattgttt      600
gcaaaatcaa aacaccacca agaaaaaaat tctcaataaa gtaaatttca tcaatgaaaa      660
ttttcttata gatgccctgg ctttaaagcg tcctattatc ttcacaactg cacactatgg      720
aaactgggaa attttaagcc ttgcttatgc ggctaaatat ggtgcgattt ccatagtggg      780
aaaaaagtta aaaagtgaag ttatgtatga aattttaagc caaagtcgca cccaatttga      840
catagaactt attgacaaaa aaggcggtat aagacaaatg ctaagtgctc taaaaaagga      900
gagagctttg ggaattttaa ctgatcaaga ctgcgtagaa aacgaaagcg taagattaaa      960
attttttaac aaagaagtga attatcaaat gggagcaagc cttatcgcac aaagaagcaa     1020
tgctttgatc atccctgttt atgcctataa agaaggtggt aaattttgca tagagttttt     1080
taaagcaaaa gattctcaaa atgcaagttt agaagaactg acactttatc aagcacaaag     1140
ttgcgaagaa atgattaaaa aaagaccttg ggaatacttt ttttttcata gacgctttgc     1200
tagttataat gaggaaattt acaagggtgc aaaatgaatc taaaacaaat aagcgttatt     1260
atcatcgtaa aaaatgctga gcaaactttg cttgagtgtt taaattcttt aaaagatttt     1320
gatgaaatta ttttacttaa caatgaaagt agcgataata ccctaaaaat agctaatgaa     1380
tttaaaaaag attttgctaa tttatatatt tatcacaatg cttttatagg ttttggagct     1440
ttaaaaaatc ttgcttttaag ttatgcaaaa aatgattgga ttttaagcat tgatgctgat     1500
gaagtgcttg aaaatgagtg tattaaagag cttaaaaatt taaaacttca agaagataat     1560
atcatcgcac ttagccgtaa aaatctctat aaaggcgaat ggataaaggc atgtggttgg     1620
tggcctgatt atgttttgag aatttttaat aaaaatttca ctcgttttaa tgataattta     1680
gtacatgaaa gccttgtttt gccaagtaat gctaaaaaaa tttatcttaa aaatggattg     1740
aagcattatt cttataagga tatctctcac ttaattgaca aaatgcagta ctactcaagt     1800
cttgggcaa  acaaaatat  acacaaaaaa agtggtgttt taaaagcaaa tttaagagct     1860
ttttggactt ttttagaaa  ttatttttta aaaaatggct ttttatatgg ttataagggt     1920
tttataatta gcgtttgttc tgcattggga acatttttta aatatatgaa attatatgaa     1980
cttcaaagac aaaaaccaaa aacttgcgct ttaataataa taacttataa tcaaaaagaa     2040
cgccttaaac tagtgcttga tagtgttaaa aatctagcct ttttacccaa tgaagtttta     2100
atcgcagatg atggtagcaa agaagataca gcaaggctta ttgaagaata tcaaaaagat     2160
tttccttgtc ctttaaaaca catttggcaa gaagatgaag ggtttaaact tagtaaaagt     2220
cgcaacaaaa ctataaaaaa cgctgatagt gaatatataa tagttattga tggtgatatg     2280
attttgaaaa aagatttcat aaaagaacat ttagaatttg cacaagaaaa gcttttttta     2340
caaggttcaa gagtaatttt aaataaaaaa gaaagcgaag aaattttaaa caaagatgat     2400
tatcgcataa ttttaataa  aaaagatttt aaaagttcta aaaattcttt tttagctaaa     2460
atattttaca gtcttttcaaa aaaaagatga aaaaatcttt taaaaaacca ctcttattaa     2520
```

```
aggtattagg ggttgcaata tgagttttt taaaactgat tttgatgaac ttgatggttt    2580
taatgaaaat tttattggtt ggggtagaga agatagtgaa tttgttgcta gatttttatt    2640
taataaaggc attttagac gattaaaatt taaagctatt gcttatcata tttatcacaa    2700 agaaatagc aaaaaatgc ttgaaagcaa tcatcaaatt tatttagata ccatcaaaaa     2760
taaaaagatt tcttggagat aaaacatgaa gaaataggt gtagttatac caatctataa    2820
tgtagaaaaa tatttaagag aatgtttaga tagcgttatc aatcaaactt atactaactt   2880
agaaatcata cttgtcaatg atggtagcac agatgaacac tcactcaata ttgcaaaaga   2940 atataccta aaagataaaa gaataactct ttttgataag aaaaatgggg gtttaagttc    3000
agctagaaat ataggtatag aatactttag cggggaatat aaattaaaaa acaaaactca   3060
acatataaaa gaaaattctt taatagaatt tcaattggat ggtaataatc cttataatat   3120
atataaagca tataaaagct ctcaagcttt taataatgaa aaagatttaa ccaattttac   3180
ttaccctagt atagattata ttatattctt agatagtgat aattattgga aactaaactg   3240
catagaagaa tgcgttataa gaatgaaaaa tgtggatgta ttgtggtttg accatgattg   3300
cacctatgaa gacaatataa aaaataagca caaaaaaaca aggatggaaa tttttgattt   3360 taaaaagaa tgtataatca ctccaaaaga atatgcaaat cgagcattaa gtgtaggatc    3420
tagagatatt tcttttggat ggaatggaat gattgatttt aatttttaa agcaaattaa    3480 acttaaattt ataaatttta ttatcaatga agatatacac tttgggataa ttttgtttgc   3540
tagtgctaat aaaatttatg ttttatcaca aagttgtat ttgtgtcgtt taagagcaaa    3600
cagtatatca aatcatgata agaagattac aaaagcaaat gtgtcagagt attttaaaga   3660
tatatatgaa actttcgggg aaaacgctaa ggaagcaaaa aattatttaa aagcagcaag   3720
cagggttata actgctttaa aattgataga atttttttaaa gatcaaaaaa acgaaaatgc   3780
acttgctata aagaaaacat ttttaccttg ctatgccaaa aaagctttaa tgattaaaaa    3840
atttaaaaaa gatcctttaa atttaaagga acaattagtt ttaattaaac cttttattca    3900
aacaaaactt cctatgata tttggaaatt ttggcaaaaa ataaaaata tttaataata     3960 aaaatataaa aaattaatta atttttaggt ataatcacta taattatagg agaaaatatt   4020
ttatatgcta tttcaatcat actttgtgaa aataatttgc ttattcatcc cttttagaaa   4080
aattagacat aaaatataaaa aaacatttt actaaaaaac atacaacgag ataaaatcga   4140
ttcttattta ccaaaaaaaa ctcttgtgca aattaataaa tacaacaatg aagatttaat   4200
taaacttaat aaagctatta taggggaggg gcataaagga tattttaatt atgatgaaaa   4260
atctaaagat ccaaaatctc ctttgaatcc ttgggctttt atacgagtaa aaaatgaagc   4320
tattacctta aaagcttctc ttgaaagcat attgcctgct atccaaagag gtgttatagg   4380
atataatgat tgtaccgatg gaagtgaaga ataattcta gaattttgca acaatatcc    4440 ttcatttata ccaataaaat atccttatga aattcaaatt caaacccaa atcagaaga    4500 aaataaactc tatagctatt ataattatgt tgcaagtttt ataccaaaag atgagtggct   4560
tataaaaata gatgtggatc atatctatga tgctaaaaaa ctttataaaa gcttctatat   4620
accaaaaaac aaatatgatg tagttagtta ttcaagggtt gatattcact attttaatga   4680
taattttttt cttgtaaag ataataatgg caatatattg aaagaaccag gagattgctt    4740
gcttatcaat aattataact taaaatgaa agaagtatta attgacagaa tcaataacaa   4800 ttggaaaaaaa gcaacaaaac aaagttttc ttcaaatata cactctttag agcaattaaa   4860
```

```
gtataaacac aggatattat ttcacactga attaaataat tatcattttc cttttttaaa    4920
aaaacataga gctcaagata tttataaata taattggata agtattgaag aatttaaaaa    4980
attctattta caaaatatta atcataaaat agaaccttct atgatttcaa agaaactct     5040 aaaaaaaata ttcttaacat tgttttaaaa attttttata tttaaataaa atttttaaag    5100 ttaaatatt tattttagct aataatgtaa ccattaattt tgttcttttt attttatata     5160
tttgaatata tagcaaatat ttaattagca catagagaac gctacaatac ttgtttaaaa    5220
tataattttg ccttaaatag tttaaaacca actgcaactc ttgaatatta ttttaacaa     5280 gcacttcatt cttagtatta caaattgaat tattattagg cacgtaatga tataaattac    5340
agttcatata tgctattttt tgagcttgac ttaacattgg ataatataac aatacatctt    5400
cagccatatt gattttaaca tctttctcga gtcttaaact cgcaaaagct tctaaataca    5460
atttctttct tataagtttc ccccacatag tccaatataa attttctttt gcaataattt    5520
tttttacaaa ctcttttttg ctataaaaac cagaattaaa gtcaaacttt ttatatgaaa    5580
taacattact ttcaacaata gcattgaaaa acactaaatc aacttcatcc tgttcatcta    5640 aaattttat acactcttca caagcattta gttccaaata atcatcagga tctaaaaaca     5700
ttatataagg agagtttgct actttcacac cttcatatct tgctcttaaa agacctaagt    5760 tttttttcatt gtggattatt tttattcttt tgtcttttt agagtattct ttggctatat    5820
ttatactatt atcatttcca caatcatcaa ctacaattat ttctatatct ttaaaagtct    5880
gattgataca gctttctatt gcccttgcta tatattgttc cacattataa gttggtaaga    5940
tgattgaaat tttaaacata tttattcctt atttattat aatttaatta taacataaaa     6000
tctattttga taaaatcgtt aaaaataaat cttgatggaa aataatcatg aaaaaagtta    6060
ttattgctgg aaatggacca agtttaaaag aaattgatta ttcaagacta ccaaatgatt    6120
ttgatgtatt tagatgtaat caatttttatt ttgaagataa atactatctt ggtaaaaaat   6180
gcaaggcagt attttacaat cctattcttt tttttgaaca atactacact ttaaaacatt    6240
taatccaaaa tcaagaatat gagaccgaac taattatgtg ttctaattac aaccaagctc    6300
atctagaaaa tgaaaatttt gtaaaaactt tttacgatta ttttcctgat gctcatttgg    6360
gatatgattt tttcaaacaa cttaaagatt ttaatgctta ttttaaattt cacgaaattt    6420
atttcaatca aagaattacc tcagggtct atatgtgtgc agtagccata gccctaggat     6480
acaaagaaat ttatctttcg ggaattgatt tttatcaaaa tgggtcatct tatgcttttg    6540
atactaaaca aaaaatcttt ttaaaattgg ctcctaatt taaaaatgat aattcacact     6600
atatcggaca tagtaaaaat acagatataa aagctttaga atttctagaa aaaacttaca    6660
aaataaaact atattgctta tgtcctaaca gtctttttagc aaatttata gaactagcgc    6720 caaatttaaa ttcaaatttt atcatacaag aaaaaaataa ctacactaaa gatatactca    6780
taccttctag tgaggcttat ggaaaatttt caaaaaatat taattttaaa aaaataaaaa    6840
ttaaagaaaa tatttattac aagttgataa aagatctatt aagattacct agtgatataa    6900
agcattattt caaaggaaaa taatgaaag aaataaaaat acaaatata atcataagtg     6960 aagaaaaagc acccttagtc gtgcctgaaa taggcattaa tcataatggc agtttagaac    7020
tagctaaaat tatggtagat gcagccttta gcacaggtgc taagattata aagcatcaaa    7080
cccacatcgt tgaagatgag atgagtaagg ccgctaaaaa agtaattcct ggtaatgcaa    7140
aaataagcat ttatgagatt atgcaaaaat gtgctttaga ttataaagat gagctagcac    7200
ttaaagaata cacagaaaaa ttaggtcttg tttatcttag cacaccttt tctcgtgcag      7260
```

-continued

```
gtgcaaaccg cttagaagat atgggagtta gtgcttttaa gattggttca ggtgagtgta    7320
ataattatcc gcttattaaa cacatagcag cctttaaaaa gcctatgata gttagcacag    7380
ggatgaatag tattgaaagt ataaaaccaa ctgtaaaaat cttattagac aatgaaattc    7440
cctttgtttt aatgcacaca accaatcttt acccaacccc gcataatctt gtaagattaa    7500
acgctatgct tgaattaaaa aaagaatttt cttgtatggt aggcttaagc gaccacacaa    7560
cagataatct tgcgtgttta ggtgcggttg cacttggtgc ttgtgtgctt gaaagacatt    7620
ttactgatag tatgcataga agtggccctg atatagtttg ttctatggat acacaggctt    7680
taaaagagct tattatacaa agtgagcaaa tggctataat gagaggaaat aatgaaagta    7740
aaaaagcagc taagcaagag caagtcacaa ttgattttgc ctttgcaagc gtagtcagca    7800
ttaaagatat taaaaaggc gaagttttat ctatggataa tatttgggtt aaaagacctg    7860
gacttggtgg aattagtgca gctgaatttg aaaatatttt aggcaaaaaa gcattaagag    7920
atatagaaaa tgatactcag ttaagctatg aggattttgc gtgaaaaaaa tccttttat    7980
aacaggcact agggctgatt attctaagat taaatcttta atgtacaggg tgcaaaactc    8040
aagcgaattt gaactttaca tctttgcaac aggaatgcac ttaagcaaaa attttggcta    8100
tacagttaaa gaactttata aaaatggctt taaaaatatt tatgaattta taaattacga    8160
taaatatttt tcaaccgata aggctttagc cactacaatt gatggatttt caagatatgt    8220
aaatgagcta aaacctgatt taatcgtagt acatggagat agaatcgagc ctttagcagc    8280
agctattgtt ggagcattaa acaatatctt agtagcacat attgaaggtg gagagatttc    8340
aggaactatt gatgatagct tacgccacgc tatatcaaaa ctagcacata ttcatttagt    8400
aaatgatgag tttgcaaaaa ggcgtttaat gcagcttgga gaagatgaaa aatctatttt    8460
tatcataggt tcgcctgatt tagaactttt aaacgataat aaaaatttcac ttaatgaagc    8520
aaaaaaatat tatgatataa attatgaaaa ctacgctttg cttatgtttc atcctgttac    8580
aactgaaatt acaagcatta aaatcaagc agataattta gtaaaagcac tgatacaaag    8640
taacaaaaat tatattgtta tttatccaaa taatgattta ggttttgaat taatcttgca    8700
aagctatgaa gaacttaaaa ataaccctag atttaagctt tttccatcgc ttagatttga    8760
gtattttata acttttgttaa aaaatgctga ttttataata ggtaattcaa gttgtatttt    8820
aaaagaggcc ttatacttaa aaacagcagg aattttagtt ggctcaaggc aaaatggaag    8880
acttggcaat gaaaatacac taaaagttaa tgcaaatagt gatgaaatac taaaagctat    8940
taataccatt cataaaaaac aagatttatt tagcgccaag ttagagattt tagatagctc    9000
aaaattattt tttgaatatt tacaaagcgg agaatttttt aaacttaaca cacaaaaagt    9060
ttttaaggat ataaaatgag cttagcaata atccctgctc gtggtggctc aaagggtatt    9120
aaaaataaaa atttggtttt attaaacaat aaacctttaa tttattacac cattaaagct    9180
gcactaaata ctaaaagcat tagtaaagtt gttgtaagca gtgatagtga tgaaatttta    9240
aattatgcaa aaagtcaaaa tgttgatatt ttaaaacgcc caattagcct tgcacaagat    9300
aatactacaa gcgataaagt gcttttacat gctctaaaat tttacaaaga ttatgaagat    9360
gtagttttt tacaacccac ttcgccgcta agaacaaata ttcatattga tgaggctttt    9420
aatctttata aaaatagcaa tgcaaatgcc ctaattagcg taagcgaatg tgataataaa    9480
attctaaaag ccttttgtttg taatgaatat ggcgatttag cagggatttg taatgatgaa    9540
tatccttta tgccaaggca aaaattgcct aaaacatata tgagcaatgg tgcaatttat    9600
```

```
attttaaaga taaagaatt tttaaacaat cctagctttt tacaaagcaa aaccaagcat      9660
tttttaatgg atgaaagctc aagtttagat attgactgtt tggaggattt aaaaaaggct      9720
gaacagatat ggaaaaaata accttaaaat gcaataaaaa tatattaaat ttattaaagc      9780
aatataatat ttatacaaaa acttatatag aaaatcctag aagattttca agactaaaaa      9840
ccaaagattt tataacctttt ccattggaaa acaatcaact agagagtgta gcggggctgg      9900
ggatagaaga atattgtgct tttaaattta gcaatatctt acatgaaatg gattcatttt      9960
cttttagcgg atcttttcta cctcattata caaaagttgg aaggtattgt tcaatttctg     10020
atggggtttc tatgtttaac tttcaacatc ctatggatag aatcagcact gcaagtttta     10080
cctatgaaac aaatcatagt tttattaacg atgcttgcca aaatcacatc aacaaaacat     10140
ttcctatagt taaccataat ccaagctcat caataacgca tttaattata caagatgatg     10200
tttggatagg aaaagatgtt ttgcttaaac agggtatcac acttgggact ggatgtgtca     10260
taggacaaag agctgtagtt actaaagatg taccaccttta tgctatagtt gcaggaattc     10320
cagccaaaat tatcaaatat agatttgatg aaaaaacaat agaaagatta ttaaaaattc     10380
aatggtggaa atatcatttt gctgattttt atgatattga tcttaatttta aaaataaacc     10440 aatatcttga cctactagaa gaaaaaatca taaaaaaatc aatttcctac tataatccaa     10500
ataaacttta ttttagagat attttagaac taaaatcaaa aaaaatttttt aatctatttt     10560 aatctatttt tcacccctgc ttcctctctc tttaaaactt caaataattt ctgatgaaat     10620
tcatcatgtg caaactcttt ggatagtttt tttatgattt cattactttt cttttttatca     10680 tgataatttt gatttaaaat ttctttattt ttattctcat atcttccatt tggattaaat     10740
tcataatgat aaatgcaagt tttaaaaaca gctattttct cacaaaacat aaaataaata     10800
taacaaaaaa gcacatcttc gccataattc aaacgctcat ctattttaat tttttcaaaa     10860 cttttttaaga tgatatcttt tttaaagcac ttcgcccaaa ccgaccagca aaaatgcctt     10920
tgtttgctta aaaattctaa aaattccttt tgattaaaaa cttcatcttg tttaaaacga     10980
taaaattgtt tggttttttac cctatgcaca aaggcatcaa aacaaagcaa atcaaaaacct     11040 tttttcatct ctttaaacgc tatttcacaa gcatcaggtg ttaaaaaatc atcactatct     11100
aaaaacatta taaaatcaga actagaatgc aaaaccccca aatttctact tgcaaaagtg     11160
cctaaatttt cttcattttg aaagatttt attcttggat cttttttttgc aaattctaaa     11220 accatatttta aactattatc tttacttttta tcatcgataa tcaaaattttc aatatctttt     11280 aaagtctgat ttatacaact ttgcaaagct cttgagataa aatcgcaaga attaaaaagc     11340
gggattatga tagaaagttg tggcatattt ttcctaaatt ttgttaaaat aataaaaaca     11400
attctatcaa agtttaggaa attttatgaaa attttttatac accttccaac ctggttaggc     11460
gatacggtaa tggc                                                         11474
```

<210> SEQ ID NO 2
<211> LENGTH: 876
<212> TYPE: DNA
<213> ORGANISM: Campylobacter jejuni
<220> FEATURE:
<221> NAME/KEY: CDS
<222> LOCATION: (1)..(876)
<223> OTHER INFORMATION: bifunctional alpha-2,3/alpha
      2,8-sialyltransferase Campylobacter sialyltransferase II
      (cstII) from C. jejuni strain OH4384 (ORF 7a of
      lipooligosaccharide (LOS) biosynthesis locus)

<400> SEQUENCE: 2

```
atg aaa aaa gtt att att gct gga aat gga cca agt tta aaa gaa att    48
Met Lys Lys Val Ile Ile Ala Gly Asn Gly Pro Ser Leu Lys Glu Ile
 1               5                  10                  15 gat tat tca aga cta cca aat gat ttt gat gta ttt aga tgt aat caa    96
Asp Tyr Ser Arg Leu Pro Asn Asp Phe Asp Val Phe Arg Cys Asn Gln
             20                  25                  30 ttt tat ttt gaa gat aaa tac tat ctt ggt aaa aaa tgc aag gca gta   144
Phe Tyr Phe Glu Asp Lys Tyr Tyr Leu Gly Lys Lys Cys Lys Ala Val
         35                  40                  45 ttt tac aat cct att ctt ttt ttt gaa caa tac tac act tta aaa cat   192
Phe Tyr Asn Pro Ile Leu Phe Phe Glu Gln Tyr Tyr Thr Leu Lys His
     50                  55                  60 tta atc caa aat caa gaa tat gag acc gaa cta att atg tgt tct aat   240
Leu Ile Gln Asn Gln Glu Tyr Glu Thr Glu Leu Ile Met Cys Ser Asn
 65                  70                  75                  80 tac aac caa gct cat cta gaa aat gaa aat ttt gta aaa act ttt tac   288
Tyr Asn Gln Ala His Leu Glu Asn Glu Asn Phe Val Lys Thr Phe Tyr
                 85                  90                  95 gat tat ttt cct gat gct cat ttg gga tat gat ttt ttc aaa caa ctt   336
Asp Tyr Phe Pro Asp Ala His Leu Gly Tyr Asp Phe Phe Lys Gln Leu
            100                 105                 110 aaa gat ttt aat gct tat ttt aaa ttt cac gaa att tat ttc aat caa   384
Lys Asp Phe Asn Ala Tyr Phe Lys Phe His Glu Ile Tyr Phe Asn Gln
        115                 120                 125 aga att acc tca ggg gtt tat atg tgt gca gta gcc ata gcc cta gga   432
Arg Ile Thr Ser Gly Val Tyr Met Cys Ala Val Ala Ile Ala Leu Gly
    130                 135                 140 tac aaa gaa att tat ctt tcg gga att gat ttt tat caa aat ggg tca   480
Tyr Lys Glu Ile Tyr Leu Ser Gly Ile Asp Phe Tyr Gln Asn Gly Ser
145                 150                 155                 160 tct tat gct ttt gat act aaa caa aaa aat ctt tta aaa ttg gct cct   528
Ser Tyr Ala Phe Asp Thr Lys Gln Lys Asn Leu Leu Lys Leu Ala Pro
                165                 170                 175 aat ttt aaa aat gat aat tca cac tat atc gga cat agt aaa aat aca   576
Asn Phe Lys Asn Asp Asn Ser His Tyr Ile Gly His Ser Lys Asn Thr
            180                 185                 190 gat ata aaa gct tta gaa ttt cta gaa aaa act tac aaa ata aaa cta   624
Asp Ile Lys Ala Leu Glu Phe Leu Glu Lys Thr Tyr Lys Ile Lys Leu
        195                 200                 205 tat tgc tta tgt cct aac agt ctt tta gca aat ttt ata gaa cta gcg   672
Tyr Cys Leu Cys Pro Asn Ser Leu Leu Ala Asn Phe Ile Glu Leu Ala
    210                 215                 220 cca aat tta aat tca aat ttt atc ata caa gaa aaa aat aac tac act   720
Pro Asn Leu Asn Ser Asn Phe Ile Ile Gln Glu Lys Asn Asn Tyr Thr
225                 230                 235                 240 aaa gat ata ctc ata cct tct agt gag gct tat gga aaa ttt tca aaa   768
Lys Asp Ile Leu Ile Pro Ser Ser Glu Ala Tyr Gly Lys Phe Ser Lys
                245                 250                 255 aat att aat ttt aaa aaa ata aaa att aaa gaa aat att tat tac aag   816
Asn Ile Asn Phe Lys Lys Ile Lys Ile Lys Glu Asn Ile Tyr Tyr Lys
            260                 265                 270 ttg ata aaa gat cta tta aga tta cct agt gat ata aag cat tat ttc   864
Leu Ile Lys Asp Leu Leu Arg Leu Pro Ser Asp Ile Lys His Tyr Phe
        275                 280                 285 aaa gga aaa taa                                                   876
Lys Gly Lys
    290
```

<210> SEQ ID NO 3
<211> LENGTH: 291

```
<212> TYPE: PRT
<213> ORGANISM: Campylobacter jejuni
<220> FEATURE:
<223> OTHER INFORMATION: bifunctional alpha-2,3/alpha
      2,8-sialyltransferase Campylobacter sialyltransferase II
      (cstII) from C. jejuni strain OH4384 (ORF 7a of
      lipooligosaccharide (LOS) biosynthesis locus)

<400> SEQUENCE: 3
```

Met Lys Lys Val Ile Ile Ala Gly Asn Gly Pro Ser Leu Lys Glu Ile
 1               5                  10                  15

Asp Tyr Ser Arg Leu Pro Asn Asp Phe Asp Val Phe Arg Cys Asn Gln
            20                  25                  30

Phe Tyr Phe Glu Asp Lys Tyr Tyr Leu Gly Lys Lys Cys Lys Ala Val
        35                  40                  45

Phe Tyr Asn Pro Ile Leu Phe Phe Glu Gln Tyr Tyr Thr Leu Lys His
    50                  55                  60

Leu Ile Gln Asn Gln Glu Tyr Glu Thr Glu Leu Ile Met Cys Ser Asn
65                  70                  75                  80

Tyr Asn Gln Ala His Leu Glu Asn Glu Asn Phe Val Lys Thr Phe Tyr
                85                  90                  95

Asp Tyr Phe Pro Asp Ala His Leu Gly Tyr Asp Phe Lys Gln Leu
            100                 105                 110

Lys Asp Phe Asn Ala Tyr Phe Lys Phe His Glu Ile Tyr Phe Asn Gln
        115                 120                 125

Arg Ile Thr Ser Gly Val Tyr Met Cys Ala Val Ala Ile Ala Leu Gly
130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Lys Asn Leu Leu Lys Leu Ala Pro
                165                 170                 175

Asn Phe Lys Asn Asp Asn Ser His Tyr Ile Gly His Ser Lys Asn Thr
            180                 185                 190

Asp Ile Lys Ala Leu Glu Phe Leu Glu Lys Thr Tyr Lys Ile Lys Leu
        195                 200                 205

Tyr Cys Leu Cys Pro Asn Ser Leu Leu Ala Asn Phe Ile Glu Leu Ala
210                 215                 220

Pro Asn Leu Asn Ser Asn Phe Ile Ile Gln Lys Asn Asn Tyr Thr
225                 230                 235                 240

Lys Asp Ile Leu Ile Pro Ser Ser Glu Ala Tyr Gly Lys Phe Ser Lys
                245                 250                 255

Asn Ile Asn Phe Lys Lys Ile Lys Glu Asn Ile Tyr Tyr Lys
            260                 265                 270

Leu Ile Lys Asp Leu Leu Arg Leu Pro Ser Asp Ile Lys His Tyr Phe
        275                 280                 285

Lys Gly Lys
    290

```
<210> SEQ ID NO 4
<211> LENGTH: 876
<212> TYPE: DNA
<213> ORGANISM: Campylobacter jejuni
<220> FEATURE:
<221> NAME/KEY: CDS
<222> LOCATION: (1)..(876)
<223> OTHER INFORMATION: bifunctional alpha-2,3/alpha
      2,8-sialyltransferase Campylobacter sialyltransferase II
      (cstII) from C. jejuni serotype O:10 (ORF 7a of
      lipooligosaccharide (LOS) biosynthesis locus)
```

<400> SEQUENCE: 4

```
atg aaa aaa gtt att att gct gga aat gga cca agt tta aaa gaa att      48
Met Lys Lys Val Ile Ile Ala Gly Asn Gly Pro Ser Leu Lys Glu Ile
 1               5                  10                  15 gat tat tca agg cta cca aat gat ttt gat gta ttt aga tgc aat caa      96
Asp Tyr Ser Arg Leu Pro Asn Asp Phe Asp Val Phe Arg Cys Asn Gln
             20                  25                  30 ttt tat ttt gaa gat aaa tac tat ctt ggt aaa aaa ttc aaa gca gta     144
Phe Tyr Phe Glu Asp Lys Tyr Tyr Leu Gly Lys Lys Phe Lys Ala Val
         35                  40                  45 ttt tac aat cct ggt ctt ttt ttt gaa caa tac tac act tta aaa cat     192
Phe Tyr Asn Pro Gly Leu Phe Phe Glu Gln Tyr Tyr Thr Leu Lys His
     50                  55                  60 tta atc caa aat caa gaa tat gag acc gaa cta att atg tgt tct aat     240
Leu Ile Gln Asn Gln Glu Tyr Glu Thr Glu Leu Ile Met Cys Ser Asn
 65                  70                  75                  80 tac aac caa gct cat cta gaa aat gaa aat ttt gta aaa act ttt tac     288
Tyr Asn Gln Ala His Leu Glu Asn Glu Asn Phe Val Lys Thr Phe Tyr
                 85                  90                  95 gat tat ttt cct gat gct cat ttg gga tat gat ttt ttt aaa caa ctt     336
Asp Tyr Phe Pro Asp Ala His Leu Gly Tyr Asp Phe Phe Lys Gln Leu
            100                 105                 110 aaa gaa ttt aat gct tat ttt aaa ttt cac gaa att tat ctc aat caa     384
Lys Glu Phe Asn Ala Tyr Phe Lys Phe His Glu Ile Tyr Leu Asn Gln
        115                 120                 125 aga att acc tca gga gtc tat atg tgt gca gta gct ata gcc cta gga     432
Arg Ile Thr Ser Gly Val Tyr Met Cys Ala Val Ala Ile Ala Leu Gly
    130                 135                 140 tac aaa gaa att tat ctt tct gga att gat ttt tat caa aat ggg tca     480
Tyr Lys Glu Ile Tyr Leu Ser Gly Ile Asp Phe Tyr Gln Asn Gly Ser
145                 150                 155                 160 tct tat gct ttt gat acc aaa caa gaa aat ctt tta aaa ctg gct cct     528
Ser Tyr Ala Phe Asp Thr Lys Gln Glu Asn Leu Leu Lys Leu Ala Pro
                165                 170                 175 gat ttt aaa aat gat cgc tca cac tat atc gga cat agt aaa aat aca     576
Asp Phe Lys Asn Asp Arg Ser His Tyr Ile Gly His Ser Lys Asn Thr
            180                 185                 190 gat ata aaa gct tta gaa ttt cta gaa aaa act tac aaa ata aaa cta     624
Asp Ile Lys Ala Leu Glu Phe Leu Glu Lys Thr Tyr Lys Ile Lys Leu
        195                 200                 205 tat tgc tta tgt cct aac agt ctt tta gca aat ttt ata gaa cta gcg     672
Tyr Cys Leu Cys Pro Asn Ser Leu Leu Ala Asn Phe Ile Glu Leu Ala
    210                 215                 220 cca aat tta aat tca aat ttt atc ata caa gaa aaa aat aac tac act     720
Pro Asn Leu Asn Ser Asn Phe Ile Ile Gln Glu Lys Asn Asn Tyr Thr
225                 230                 235                 240 aaa gat ata ctc ata cct tct agt gag gct tat gga aaa ttt tca aaa     768
Lys Asp Ile Leu Ile Pro Ser Ser Glu Ala Tyr Gly Lys Phe Ser Lys
                245                 250                 255 aat att aat ttt aaa aaa ata aaa att aaa gaa aat att tat tac aag     816
Asn Ile Asn Phe Lys Lys Ile Lys Ile Lys Glu Asn Ile Tyr Tyr Lys
            260                 265                 270 ttg ata aaa gat cta tta aga tta cct agt gat ata aag cat tat ttc     864
Leu Ile Lys Asp Leu Leu Arg Leu Pro Ser Asp Ile Lys His Tyr Phe
        275                 280                 285 aaa gga aaa taa                                                     876
Lys Gly Lys
    290
```

<210> SEQ ID NO 5
<211> LENGTH: 291
<212> TYPE: PRT
<213> ORGANISM: Campylobacter jejuni
<220> FEATURE:
<223> OTHER INFORMATION: bifunctional alpha-2,3/alpha
2,8-sialyltransferase Campylobacter sialyltransferase II
(cstII) from C. jejuni serotype O:10 (ORF 7a of
lipooligosaccharide (LOS) biosynthesis locus)

<400> SEQUENCE: 5

Met Lys Lys Val Ile Ile Ala Gly Asn Gly Pro Ser Leu Lys Glu Ile
 1               5                  10                  15

Asp Tyr Ser Arg Leu Pro Asn Asp Phe Asp Val Phe Arg Cys Asn Gln
            20                  25                  30

Phe Tyr Phe Glu Asp Lys Tyr Tyr Leu Gly Lys Lys Phe Lys Ala Val
        35                  40                  45

Phe Tyr Asn Pro Gly Leu Phe Phe Glu Gln Tyr Tyr Thr Leu Lys His
    50                  55                  60

Leu Ile Gln Asn Gln Glu Tyr Glu Thr Glu Leu Ile Met Cys Ser Asn
65                  70                  75                  80

Tyr Asn Gln Ala His Leu Glu Asn Glu Asn Phe Val Lys Thr Phe Tyr
                85                  90                  95

Asp Tyr Phe Pro Asp Ala His Leu Gly Tyr Asp Phe Phe Lys Gln Leu
           100                 105                 110

Lys Glu Phe Asn Ala Tyr Phe Lys Phe His Glu Ile Tyr Leu Asn Gln
       115                 120                 125

Arg Ile Thr Ser Gly Val Tyr Met Cys Ala Val Ala Ile Ala Leu Gly
   130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Glu Asn Leu Leu Lys Leu Ala Pro
                165                 170                 175

Asp Phe Lys Asn Asp Arg Ser His Tyr Ile Gly His Ser Lys Asn Thr
            180                 185                 190

Asp Ile Lys Ala Leu Glu Phe Leu Glu Lys Thr Tyr Lys Ile Lys Leu
        195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Ser Lys
                245                 250                 255

Asn Ile Asn Phe Lys Lys Ile Lys Lys Glu Asn Ile Tyr Tyr Lys
            260                 265                 270

Leu Ile Lys Asp Leu Leu Arg Leu Pro Ser Asp Ile Lys His Tyr Phe
        275                 280                 285

Lys Gly Lys
    290

<210> SEQ ID NO 6
<211> LENGTH: 876
<212> TYPE: DNA
<213> ORGANISM: Campylobacter jejuni
<220> FEATURE:
<221> NAME/KEY: CDS
<222> LOCATION: (1)..(876)
<223> OTHER INFORMATION: Campylobacter alpha-2,3/alpha -continued 2,8-sialyltransferase II (cstII) from C. jejuni serotype O:41

<400> SEQUENCE: 6

| | | | | | | | | | | | | | | | | |
|---|---|---|---|---|---|---|---|---|---|---|---|---|---|---|---|---|
| atg | aaa | aaa | gtt | att | att | gct | gga | aat | gga | cca | agt | tta | aaa | gaa | att | 48 |
| Met | Lys | Lys | Val | Ile | Ile | Ala | Gly | Asn | Gly | Pro | Ser | Leu | Lys | Glu | Ile | |
| 1 | | | | 5 | | | | | 10 | | | | | 15 | | |

| gat | tat | tca | aga | cta | cca | aat | gat | ttt | gat | gta | ttt | aga | tgc | aat | caa | 96 |
|---|---|---|---|---|---|---|---|---|---|---|---|---|---|---|---|---|
| Asp | Tyr | Ser | Arg | Leu | Pro | Asn | Asp | Phe | Asp | Val | Phe | Arg | Cys | Asn | Gln | |
| | | | 20 | | | | | 25 | | | | | 30 | | | |

| ttt | tat | ttt | gaa | gat | aaa | tac | tat | ctt | ggt | aaa | aaa | tgc | aaa | gca | gta | 144 |
|---|---|---|---|---|---|---|---|---|---|---|---|---|---|---|---|---|
| Phe | Tyr | Phe | Glu | Asp | Lys | Tyr | Tyr | Leu | Gly | Lys | Lys | Cys | Lys | Ala | Val | |
| | 35 | | | | | 40 | | | | | 45 | | | | | |

| ttt | tac | aat | cct | agt | ctt | ttt | ttt | gaa | caa | tac | tac | act | tta | aaa | cat | 192 |
|---|---|---|---|---|---|---|---|---|---|---|---|---|---|---|---|---|
| Phe | Tyr | Asn | Pro | Ser | Leu | Phe | Phe | Glu | Gln | Tyr | Tyr | Thr | Leu | Lys | His | |
| | 50 | | | | | 55 | | | | | 60 | | | | | |

| tta | atc | caa | aat | caa | gaa | tat | gag | acc | gaa | cta | atc | atg | tgt | tct | aat | 240 |
|---|---|---|---|---|---|---|---|---|---|---|---|---|---|---|---|---|
| Leu | Ile | Gln | Asn | Gln | Glu | Tyr | Glu | Thr | Glu | Leu | Ile | Met | Cys | Ser | Asn | |
| 65 | | | | | 70 | | | | | 75 | | | | | 80 | |

| ttt | aac | caa | gct | cat | cta | gaa | aat | caa | aat | ttt | gta | aaa | act | ttt | tac | 288 |
|---|---|---|---|---|---|---|---|---|---|---|---|---|---|---|---|---|
| Phe | Asn | Gln | Ala | His | Leu | Glu | Asn | Gln | Asn | Phe | Val | Lys | Thr | Phe | Tyr | |
| | | | | 85 | | | | | 90 | | | | | 95 | | |

| gat | tat | ttc | cct | gat | gct | cat | ttg | gga | tat | gat | ttt | ttc | aaa | caa | ctt | 336 |
|---|---|---|---|---|---|---|---|---|---|---|---|---|---|---|---|---|
| Asp | Tyr | Phe | Pro | Asp | Ala | His | Leu | Gly | Tyr | Asp | Phe | Phe | Lys | Gln | Leu | |
| | | | 100 | | | | | 105 | | | | | 110 | | | |

| aaa | gaa | ttc | aat | gct | tat | ttt | aaa | ttt | cac | gaa | att | tat | ttc | aat | caa | 384 |
|---|---|---|---|---|---|---|---|---|---|---|---|---|---|---|---|---|
| Lys | Glu | Phe | Asn | Ala | Tyr | Phe | Lys | Phe | His | Glu | Ile | Tyr | Phe | Asn | Gln | |
| | | | 115 | | | | | 120 | | | | | 125 | | | |

| aga | att | acc | tca | ggg | gtc | tat | atg | tgc | aca | gta | gcc | ata | gcc | cta | gga | 432 |
|---|---|---|---|---|---|---|---|---|---|---|---|---|---|---|---|---|
| Arg | Ile | Thr | Ser | Gly | Val | Tyr | Met | Cys | Thr | Val | Ala |

<210> SEQ ID NO 7
<211> LENGTH: 291
<212> TYPE: PRT
<213> ORGANISM: Campylobacter jejuni
<220> FEATURE:
<223> OTHER INFORMATION: Campylobacter alpha-2,3/alpha
2,8-sialyltransferase II (cstII) from C. jejuni serotype O:41

<400> SEQUENCE: 7

Met Lys Lys Val Ile Ile Ala Gly Asn Gly Pro Ser Leu Lys Glu Ile
1               5                   10                  15

Asp Tyr Ser Arg Leu Pro Asn Asp Phe Asp Val Phe Arg Cys Asn Gln
            20                  25                  30

Phe Tyr Phe Glu Asp Lys Tyr Tyr Leu Gly Lys Lys Cys Lys Ala Val
        35                  40                  45

Phe Tyr Asn Pro Ser Leu Phe Phe Glu Gln Tyr Tyr Thr Leu Lys His
    50                  55                  60

Leu Ile Gln Asn Gln Glu Tyr Glu Thr Glu Leu Ile Met Cys Ser Asn
65                  70                  75                  80

Phe Asn Gln Ala His Leu Glu Asn Gln Asn Phe Val Lys Thr Phe Tyr
                85                  90                  95

Asp Tyr Phe Pro Asp Ala His Leu Gly Tyr Asp Phe Phe Lys Gln Leu
            100                 105                 110

Lys Glu Phe Asn Ala Tyr Phe Lys Phe His Glu Ile Tyr Phe Asn Gln
        115                 120                 125

Arg Ile Thr Ser Gly Val Tyr Met Cys Thr Val Ala Ile Ala Leu Gly
    130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Lys Asn Leu Leu Lys Leu Ala Pro
                165                 170                 175

Asn Phe Lys Asn Asp Asn Ser His Tyr Ile Gly His Ser Lys Asn Thr
            180                 185                 190

Asp Ile Lys Ala Leu Glu Phe Leu Glu Lys Thr Tyr Glu Ile Lys Leu
        195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Thr Lys
                245                 250                 255

Asn Ile Asn Phe Lys Lys Ile Lys Ile Lys Glu Asn Ile Tyr Tyr Lys
            260                 265                 270

Leu Ile Lys Asp Leu Leu Arg Leu Pro Ser Asp Ile Lys His Tyr Phe
        275                 280                 285

Lys Gly Lys
    290

<210> SEQ ID NO 8
<211> LENGTH: 876
<212> TYPE: DNA
<213> ORGANISM: Campylobacter jejuni
<220> FEATURE:
<221> NAME/KEY: CDS
<222> LOCATION: (1)..(876)
<223> OTHER INFORMATION: Campylobacter alpha-2,3/alpha
2,8-sialyltransferase II (CstII) from C. jejuni O:19

<400> SEQUENCE: 8

```
atg aaa aaa gtt att att gct gga aat gga cca agt tta aaa gaa att      48
Met Lys Lys Val Ile Ile Ala Gly Asn Gly Pro Ser Leu Lys Glu Ile
 1               5                  10                  15 gat tat tca agg cta cca aat gat ttt gat gta ttt aga tgt aat caa      96
Asp Tyr Ser Arg Leu Pro Asn Asp Phe Asp Val Phe Arg Cys Asn Gln
            20                  25                  30 ttt tat ttt gaa gat aaa tac tat ctt ggt aaa aaa tgc aaa gca gtg     144
Phe Tyr Phe Glu Asp Lys Tyr Tyr Leu Gly Lys Lys Cys Lys Ala Val
        35                  40                  45 ttt tac acc cct aat ttc ttc ttt gag caa tac tac act tta aaa cat     192
Phe Tyr Thr Pro Asn Phe Phe Phe Glu Gln Tyr Tyr Thr Leu Lys His
     50                  55                  60 tta atc caa aat caa gaa tat gag acc gaa cta att atg tgt tct aat     240
Leu Ile Gln Asn Gln Glu Tyr Glu Thr Glu Leu Ile Met Cys Ser Asn
 65                  70                  75                  80 tac aac caa gct cat cta gaa aat gaa aat ttt gta aaa act ttt tac     288
Tyr Asn Gln Ala His Leu Glu Asn Glu Asn Phe Val Lys Thr Phe Tyr
                 85                  90                  95 gat tat ttt cct gat gct cat ttg gga tat gat ttt ttt aaa caa ctt     336
Asp Tyr Phe Pro Asp Ala His Leu Gly Tyr Asp Phe Phe Lys Gln Leu
            100                 105                 110 aaa gaa ttt aat gct tat ttt aaa ttt cac gaa att tat ttc aat caa     384
Lys Glu Phe Asn Ala Tyr Phe Lys Phe His Glu Ile Tyr Phe Asn Gln
        115                 120                 125 aga att acc tca ggg gtc tat atg tgt gca gta gcc ata gcc cta gga     432
Arg Ile Thr Ser Gly Val Tyr Met Cys Ala Val Ala Ile Ala Leu Gly
    130                 135                 140 tac aaa gaa att tat ctt tcg gga att gat ttt tat caa aat ggg tca     480
Tyr Lys Glu Ile Tyr Leu Ser Gly Ile Asp Phe Tyr Gln Asn Gly Ser
145                 150                 155                 160 tct tat gct ttt gat acc aaa caa gaa aat ctt tta aaa cta gcc cct     528
Ser Tyr Ala Phe Asp Thr Lys Gln Glu Asn Leu Leu Lys Leu Ala Pro
                165                 170                 175 gat ttt aaa aat gat cgc tcg cac tat atc gga cat agt aaa aat aca     576
Asp Phe Lys Asn Asp Arg Ser His Tyr Ile Gly His Ser Lys Asn Thr
            180                 185                 190 gat ata aaa gct tta gaa ttt cta gaa aaa act tac aaa ata aaa cta     624
Asp Ile Lys Ala Leu Glu Phe Leu Glu Lys Thr Tyr Lys Ile Lys Leu
        195                 200                 205 tat tgc tta tgt cct aat agt ctt tta gca aat ttt ata gaa cta gcg     672
Tyr Cys Leu Cys Pro Asn Ser Leu Leu Ala Asn Phe Ile Glu Leu Ala
    210                 215                 220 cca aat tta aat tca aat ttt atc ata caa gaa aaa aat aac tac act     720
Pro Asn Leu Asn Ser Asn Phe Ile Ile Gln Glu Lys Asn Asn Tyr Thr
225                 230                 235                 240 aaa gat ata ctc ata cct tct agt gag gct tat gga aaa ttt tca aaa     768
Lys Asp Ile Leu Ile Pro Ser Ser Glu Ala Tyr Gly Lys Phe Ser Lys
                245                 250                 255 aat att aat ttt aaa aaa ata aaa att aaa gaa aat gtt tat tac aag     816
Asn Ile Asn Phe Lys Lys Ile Lys Ile Lys Glu Asn Val Tyr Tyr Lys
            260                 265                 270 ttg ata aaa gat cta tta aga tta cct agt gat ata aag cat tat ttc     864
Leu Ile Lys Asp Leu Leu Arg Leu Pro Ser Asp Ile Lys His Tyr Phe
        275                 280                 285 aaa gga aaa taa                                                     876
Lys Gly Lys
    290
```

<210> SEQ ID NO 9
<211> LENGTH: 291
<212> TYPE: PRT
<213> ORGANISM: Campylobacter jejuni
<220> FEATURE:
<223> OTHER INFORMATION: Campylobacter alpha-2,3/alpha
    2,8-sialyltransferase II (CstII) from C. jejuni O:19

<400> SEQUENCE: 9

```
Met Lys Lys Val Ile Ile Ala Gly Asn Gly Pro Ser Leu Lys Glu Ile
 1               5                  10                  15

Asp Tyr Ser Arg Leu Pro Asn Asp Phe Asp Val Phe Arg Cys Asn Gln
            20                  25                  30

Phe Tyr Phe Glu Asp Lys Tyr Tyr Leu Gly Lys Lys Cys Lys Ala Val
        35                  40                  45

Phe Tyr Thr Pro Asn Phe Phe Phe Glu Gln Tyr Tyr Thr Leu Lys His
    50                  55                  60

Leu Ile Gln Asn Gln Glu Tyr Glu Thr Glu Leu Ile Met Cys Ser Asn
65                  70                  75                  80

Tyr Asn Gln Ala His Leu Glu Asn Glu Asn Phe Val Lys Thr Phe Tyr
                85                  90                  95

Asp Tyr Phe Pro Asp Ala His Leu Gly Tyr Asp Phe Lys Gln Leu
            100                 105                 110

Lys Glu Phe Asn Ala Tyr Phe Lys Phe His Glu Ile Tyr Phe Asn Gln
        115                 120                 125

Arg Ile Thr Ser Gly Val Tyr Met Cys Ala Val Ala Ile Ala Leu Gly
    130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Glu Asn Leu Leu Lys Leu Ala Pro
                165                 170                 175

Asp Phe Lys Asn Asp Arg Ser His Tyr Ile Gly His Ser Lys Asn Thr
            180                 185                 190

Asp Ile Lys Ala Leu Glu Phe Leu Glu Lys Thr Tyr Lys Ile Lys Leu
        195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Ser Lys
                245                 250                 255

Asn Ile Asn Phe Lys Lys Ile Lys Ile Lys Glu Asn Val Tyr Tyr Lys
            260                 265                 270

Leu Ile Lys Asp Leu Leu Arg Leu Pro Ser Asp Ile Lys His Tyr Phe
        275                 280                 285

Lys Gly Lys
    290
```

<210> SEQ ID NO 10
<211> LENGTH: 294
<212> TYPE: PRT
<213> ORGANISM: Campylobacter jejuni
<220> FEATURE:
<223> OTHER INFORMATION: Campylobacter alpha-2,3/alpha
    2,8-sialyltransferase II (CstII) from C. jejuni strain NCTC 11168

<400> SEQUENCE: 10

```
Met Ser Met Asn Ile Asn Ala Leu Val Cys Gly Asn Gly Pro Ser Leu
 1               5                  10                  15

Lys Asn Ile Asp Tyr Lys Arg Leu Pro Lys Gln Phe Asp Val Phe Arg
             20                  25                  30

Cys Asn Gln Phe Tyr Phe Glu Asp Arg Tyr Phe Val Gly Lys Asp Val
         35                  40                  45

Lys Tyr Val Phe Phe Asn Pro Phe Val Phe Glu Gln Tyr Tyr Thr
 50                  55                  60

Ser Lys Lys Leu Ile Gln Asn Glu Glu Tyr Asn Ile Glu Asn Ile Val
 65              70                  75                  80

Cys Ser Thr Ile Asn Leu Glu Tyr Ile Asp Gly Phe Gln Phe Val Asp
                 85                  90                  95

Asn Phe Glu Leu Tyr Phe Ser Asp Ala Phe Leu Gly His Glu Ile Ile
             100                 105                 110

Lys Lys Leu Lys Asp Phe Phe Ala Tyr Ile Lys Tyr Asn Glu Ile Tyr
         115                 120                 125

Asn Arg Gln Arg Ile Thr Ser Gly Val Tyr Met Cys Ala Thr Ala Val
    130                 135                 140

Ala Leu Gly Tyr Lys Ser Ile Tyr Ile Ser Gly Ile Asp Phe Tyr Gln
145                 150                 155                 160

Asp Thr Asn Asn Leu Tyr Ala Phe Asp Asn Asn Lys Lys Asn Leu Leu
                 165                 170                 175

Asn Lys Cys Thr Gly Phe Lys Asn Gln Lys Phe Lys Phe Ile Asn His
            180                 185                 190

Ser Met Ala Cys Asp Leu Gln Ala Leu Asp Tyr Leu Met Lys Arg Tyr
        195                 200                 205

Asp Val Asn Ile Tyr Ser Leu Asn Ser Asp Glu Tyr Phe Lys Leu Ala
    210                 215                 220

Pro Asp Ile Gly Ser Asp Phe Val Leu Ser Lys Pro Lys Tyr
225                 230                 235                 240

Ile Asn Asp Ile Leu Ile Pro Asp Lys Tyr Ala Gln Glu Arg Tyr Tyr
                245                 250                 255

Gly Lys Lys Ser Arg Leu Lys Glu Asn Leu His Tyr Lys Leu Ile Lys
            260                 265                 270

Asp Leu Ile Arg Leu Pro Ser Asp Ile Lys His Tyr Leu Lys Glu Lys
        275                 280                 285

Tyr Ala Asn Lys Asn Arg
290

<210> SEQ ID NO 11
<211> LENGTH: 873
<212> TYPE: DNA
<213> ORGANISM: Campylobacter jejuni
<220> FEATURE:
<221> NAME/KEY: CDS
<222> LOCATION: (1)..(873)
<223> OTHER INFORMATION: Campylobacter alpha-2,3/alpha
      2,8-sialyltransferase II (CstII) from C. jejuni O:4

<400> SEQUENCE: 11 atg aaa aaa gtt att att gct gga aat gga cca agt tta aaa gaa att      48
Met Lys Lys Val Ile Ile Ala Gly Asn Gly Pro Ser Leu Lys Glu Ile
 1               5                  10                  15 gat tat tca agg cta cca aat gat ttt gat gta ttt aga tgt aat caa      96
Asp Tyr Ser Arg Leu Pro Asn Asp Phe Asp Val Phe Arg Cys Asn Gln
             20                  25                  30 ttt tat ttt gaa gat aaa tac tat ctt ggt aaa aaa tgc aaa gca gtg     144
```

|  |  |  |  |  |  |  |  |  |  |  |  |  |  |
|---|---|---|---|---|---|---|---|---|---|---|---|---|---|
| Phe | Tyr | Phe | Glu | Asp | Lys | Tyr | Tyr | Leu | Gly | Lys | Lys | Cys | Lys | Ala | Val |
|  |  |  | 35 |  |  |  | 40 |  |  |  | 45 |  |  |

| ttt | tac | acc | cct | ggt | ttc | ttc | ttt | gag | caa | tac | tac | act | tta | aaa | cat | 192 |
|---|---|---|---|---|---|---|---|---|---|---|---|---|---|---|---|---|
| Phe | Tyr | Thr | Pro | Gly | Phe | Phe | Phe | Glu | Gln | Tyr | Tyr | Thr | Leu | Lys | His |  |
|  | 50 |  |  |  | 55 |  |  |  |  | 60 |  |  |  |  |  |  |

| tta | atc | caa | aat | caa | gaa | tat | gag | acc | gaa | cta | att | atg | tgt | tct | aat | 240 |
|---|---|---|---|---|---|---|---|---|---|---|---|---|---|---|---|---|
| Leu | Ile | Gln | Asn | Gln | Glu | Tyr | Glu | Thr | Glu | Leu | Ile | Met | Cys | Ser | Asn |  |
| 65 |  |  |  |  | 70 |  |  |  |  | 75 |  |  |  |  | 80 |  |

| tac | aac | caa | gct | cat | cta | gaa | aat | gaa | aat | ttt | gta | aaa | act | ttt | tac | 288 |
|---|---|---|---|---|---|---|---|---|---|---|---|---|---|---|---|---|
| Tyr | Asn | Gln | Ala | His | Leu | Glu | Asn | Glu | Asn | Phe | Val | Lys | Thr | Phe | Tyr |  |
|  |  |  |  | 85 |  |  |  |  | 90 |  |  |  |  | 95 |  |  |

| gat | tat | ttt | cct | gat | gct | cat | ttg | gga | tat | gat | ttt | ttt | aaa | caa | ctt | 336 |
|---|---|---|---|---|---|---|---|---|---|---|---|---|---|---|---|---|
| Asp | Tyr | Phe | Pro | Asp | Ala | His | Leu | Gly | Tyr | Asp | Phe | Phe | Lys | Gln | Leu |  |
|  |  |  | 100 |  |  |  |  | 105 |  |  |  |  | 110 |  |  |  |

| aaa | gaa | ttt | aat | gct | tat | ttt | aaa | ttt | cac | gaa | att | tat | ttc | aat | caa | 384 |
|---|---|---|---|---|---|---|---|---|---|---|---|---|---|---|---|---|
| Lys | Glu | Phe | Asn | Ala | Tyr | Phe | Lys | Phe | His | Glu | Ile | Tyr | Phe | Asn | Gln |  |
|  |  | 115 |  |  |  |  | 120 |  |  |  |  | 125 |  |  |  |  |

| aga | att | acc | tca | ggg | gtc | tat | atg | tgt | gca | gta | gcc | ata | gcc | cta | gga | 432 |
|---|---|---|---|---|---|---|---|---|---|---|---|---|---|---|---|---|
| Arg | Ile | Thr | Ser | Gly | Val | Tyr | Met | Cys | Ala | Val | Ala | Ile | Ala | Leu | Gly |  |
|  | 130 |  |  |  |  | 135 |  |  |  |  | 140 |  |  |  |  |  |

| tac | aaa | gaa | att | tat | ctt | tcg | gga | att | gat | ttt | tat | caa | aat | ggg | tca | 480 |
|---|---|---|---|---|---|---|---|---|---|---|---|---|---|---|---|---|
| Tyr | Lys | Glu | Ile | Tyr | Leu | Ser | Gly | Ile | Asp | Phe | Tyr | Gln | Asn | Gly | Ser |  |
| 145 |  |  |  |  | 150 |  |  |  |  | 155 |  |  |  |  | 160 |  |

| tct | tat | gct | ttt | gat | acc | aaa | caa | gaa | aat | ctt | tta | aaa | cta | gcc | cct | 528 |
|---|---|---|---|---|---|---|---|---|---|---|---|---|---|---|---|---|
| Ser | Tyr | Ala | Phe | Asp | Thr | Lys | Gln | Glu | Asn | Leu | Leu | Lys | Leu | Ala | Pro |  |
|  |  |  |  | 165 |  |  |  |  | 170 |  |  |  |  | 175 |  |  |

| gat | ttt | aaa | aat | gat | cgc | tca | cac | tat | atc | gga | cat | agt | aaa | aat | aca | 576 |
|---|---|---|---|---|---|---|---|---|---|---|---|---|---|---|---|---|
| Asp | Phe | Lys | Asn | Asp | Arg | Ser | His | Tyr | Ile | Gly | His | Ser | Lys | Asn | Thr |  |
|  |  |  | 180 |  |  |  |  | 185 |  |  |  |  | 190 |  |  |  |

| gat | ata | aaa | gct | tta | gaa | ttt | cta | gaa | aaa | act | tac | aaa | ata | aaa | cta | 624 |
|---|---|---|---|---|---|---|---|---|---|---|---|---|---|---|---|---|
| Asp | Ile | Lys | Ala | Leu | Glu | Phe | Leu | Glu | Lys | Thr | Tyr | Lys | Ile | Lys | Leu |  |
|  |  | 195 |  |  |  |  | 200 |  |  |  |  | 205 |  |  |  |  |

| tat | tgc | tta | tgt | cct | aac | agt | ctt | tta | gca | aat | ttt | ata | gaa | cta | gcg | 672 |
|---|---|---|---|---|---|---|---|---|---|---|---|---|---|---|---|---|
| Tyr | Cys | Leu | Cys | Pro | Asn | Ser | Leu | Leu | Ala | Asn | Phe | Ile | Glu | Leu | Ala |  |
| 210 |  |  |  |  | 215 |  |  |  |  | 220 |  |  |  |  |  |  |

| cca | aat | tta | aat | tca | aat | ttt | atc | ata | caa | gaa | aaa | aat | aac | tac | act | 720 |
|---|---|---|---|---|---|---|---|---|---|---|---|---|---|---|---|---|
| Pro | Asn | Leu | Asn | Ser | Asn | Phe | Ile | Ile | Gln | Glu | Lys | Asn | Asn | Tyr | Thr |  |
| 225 |  |  |  |  | 230 |  |  |  |  | 235 |  |  |  |  | 240 |  |

| aaa | gat | ata | ctc | ata | cct | tct | agt | gag | gct | tat | gga | aaa | ttt | tca | aaa | 768 |
|---|---|---|---|---|---|---|---|---|---|---|---|---|---|---|---|---|
| Lys | Asp | Ile | Leu | Ile | Pro | Ser | Ser | Glu | Ala | Tyr | Gly | Lys | Phe | Ser | Lys |  |
|  |  |  |  | 245 |  |  |  |  | 250 |  |  |  |  | 255 |  |  |

| aat | att | aat | ttt | aaa | aaa | ata | aaa | att | aaa | gaa | aat | gtt | tat | tac | aag | 816 |
|---|---|---|---|---|---|---|---|---|---|---|---|---|---|---|---|---|
| Asn | Ile | Asn | Phe | Lys | Lys | Ile | Lys | Ile | Lys | Glu | Asn | Val | Tyr | Tyr | Lys |  |
|  |  |  | 260 |  |  |  |  | 265 |  |  |  |  | 270 |  |  |  |

| ttg | ata | aaa | gat | cta | tta | aga | tta | cct | agt | gat | ata | aag | cat | tat | ttc | 864 |
|---|---|---|---|---|---|---|---|---|---|---|---|---|---|---|---|---|
| Leu | Ile | Lys | Asp | Leu | Leu | Arg | Leu | Pro | Ser | Asp | Ile | Lys | His | Tyr | Phe |  |
|  |  | 275 |  |  |  |  | 280 |  |  |  |  | 285 |  |  |  |  |

| aaa | gga | aaa | 873 |
|---|---|---|---|
| Lys | Gly | Lys |  |
|  | 290 |  |  |

<210> SEQ ID NO 12
<211> LENGTH: 291
<212> TYPE: PRT
<213> ORGANISM: Campylobacter jejuni
<220> FEATURE:
<223> OTHER INFORMATION: Campylobacter alpha-2,3/alpha
    2,8-sialyltransferase II (CstII) from C. jejuni O:4

<400> SEQUENCE: 12

Met Lys Lys Val Ile Ile Ala Gly Asn Gly Pro Ser Leu Lys Glu Ile

```
              1               5              10              15
Asp Tyr Ser Arg Leu Pro Asn Asp Phe Asp Val Phe Arg Cys Asn Gln
                     20                  25                  30

Phe Tyr Phe Glu Asp Lys Tyr Tyr Leu Gly Lys Lys Cys Lys Ala Val
                 35                  40                  45

Phe Tyr Thr Pro Gly Phe Phe Glu Gln Tyr Tyr Thr Leu Lys His
             50                  55                  60

Leu Ile Gln Asn Gln Glu Tyr Glu Thr Glu Leu Ile Met Cys Ser Asn
 65                  70                  75                  80

Tyr Asn Gln Ala His Leu Glu Asn Glu Asn Phe Val Lys Thr Phe Tyr
                 85                  90                  95

Asp Tyr Phe Pro Asp Ala His Leu Gly Tyr Asp Phe Lys Gln Leu
                100                 105                 110

Lys Glu Phe Asn Ala Tyr Phe Lys Phe His Glu Ile Tyr Phe Asn Gln
                115                 120                 125

Arg Ile Thr Ser Gly Val Tyr Met Cys Ala Val Ala Ile Ala Leu Gly
    130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Glu Asn Leu Leu Lys Leu Ala Pro
                165                 170                 175

Asp Phe Lys Asn Asp Arg Ser His Tyr Ile Gly His Ser Lys Asn Thr
                180                 185                 190

Asp Ile Lys Ala Leu Glu Phe Leu Glu Lys Thr Tyr Lys Ile Lys Leu
    195                 200                 205

Tyr Cys Leu Cys Pro Asn Ser Leu Leu Ala Asn Phe Ile Glu Leu Ala
210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Ser Lys
                245                 250                 255

Asn Ile Asn Phe Lys Lys Ile Lys Ile Lys Glu Asn Val Tyr Tyr Lys
                260                 265                 270

Leu Ile Lys Asp Leu Leu Arg Leu Pro Ser Asp Ile Lys His Tyr Phe
                275                 280                 285

Lys Gly Lys
    290

<210> SEQ ID NO 13
<211> LENGTH: 873
<212> TYPE: DNA
<213> ORGANISM: Campylobacter jejuni
<220> FEATURE:
<221> NAME/KEY: CDS
<222> LOCATION: (1)..(873)
<223> OTHER INFORMATION: Campylobacter alpha-2,3/alpha
      2,8-sialyltransferase II (CstII) from C. jejuni O:36

<400> SEQUENCE: 13 atg aaa aaa gtt att att gct gga aat gga cca agt tta aaa gaa att      48
Met Lys Lys Val Ile Ile Ala Gly Asn Gly Pro Ser Leu Lys Glu Ile
  1               5                  10                  15 gat tat tca agg cta cca aat gat ttt gat gta ttt aga tgt aat caa      96
Asp Tyr Ser Arg Leu Pro Asn Asp Phe Asp Val Phe Arg Cys Asn Gln
                 20                  25                  30 ttt tat ttt gaa gat aaa tac tat ctt ggt aaa aaa tgc aaa aca gtg     144
Phe Tyr Phe Glu Asp Lys Tyr Tyr Leu Gly Lys Lys Cys Lys Thr Val
```

```
                35                  40                  45
ttt  tac  acc  cct  aat  ttc  ttc  ttt  gag  caa  tac  tac  act  tta  aaa  cat      192
Phe  Tyr  Thr  Pro  Asn  Phe  Phe  Phe  Glu  Gln  Tyr  Tyr  Thr  Leu  Lys  His
         50                       55                       60 tta  atc  caa  aat  caa  gaa  tat  gag  acc  gaa  cta  att  atg  tgt  tct  aat      240
Leu  Ile  Gln  Asn  Gln  Glu  Tyr  Glu  Thr  Glu  Leu  Ile  Met  Cys  Ser  Asn
 65                      70                       75                       80 tac  aac  caa  gct  cat  cta  gaa  aat  gaa  aat  ttt  gta  aaa  act  ttt  tac      288
Tyr  Asn  Gln  Ala  His  Leu  Glu  Asn  Glu  Asn  Phe  Val  Lys  Thr  Phe  Tyr
                    85                       90                       95 gat  tat  ttt  cct  gat  gct  cat  ttg  gga  tat  gat  ttt  ttt  aaa  caa  ctt      336
Asp  Tyr  Phe  Pro  Asp  Ala  His  Leu  Gly  Tyr  Asp  Phe  Phe  Lys  Gln  Leu
               100                      105                      110 aaa  gaa  ttt  aat  gct  tat  ttt  aaa  ttt  cac  gaa  att  tat  ttc  aat  caa      384
Lys  Glu  Phe  Asn  Ala  Tyr  Phe  Lys  Phe  His  Glu  Ile  Tyr  Phe  Asn  Gln
          115                      120                      125 aga  att  acc  tca  ggg  gtc  tat  atg  tgt  gca  gta  gcc  ata  gcc  cta  gga      432
Arg  Ile  Thr  Ser  Gly  Val  Tyr  Met  Cys  Ala  Val  Ala  Ile  Ala  Leu  Gly
     130                      135                      140 tac  aaa  gaa  att  tat  ctt  tcg  gga  att  gat  ttt  tat  caa  aat  ggg  tca      480
Tyr  Lys  Glu  Ile  Tyr  Leu  Ser  Gly  Ile  Asp  Phe  Tyr  Gln  Asn  Gly  Ser
145                      150                      155                      160 tct  tat  gct  ttt  gat  acc  aaa  caa  gaa  aat  ctt  tta  aaa  cta  gcc  cct      528
Ser  Tyr  Ala  Phe  Asp  Thr  Lys  Gln  Glu  Asn  Leu  Leu  Lys  Leu  Ala  Pro
               165                      170                      175 gat  ttt  aaa  aat  gat  cgc  tca  cac  tat  atc  gga  cat  agt  aaa  aat  aca      576
Asp  Phe  Lys  Asn  Asp  Arg  Ser  His  Tyr  Ile  Gly  His  Ser  Lys  Asn  Thr
          180                      185                      190 gat  ata  aaa  gct  tta  gaa  ttt  cta  gaa  aaa  act  tac  aaa  ata  aaa  cta      624
Asp  Ile  Lys  Ala  Leu  Glu  Phe  Leu  Glu  Lys  Thr  Tyr  Lys  Ile  Lys  Leu
     195                      200                      205 tat  tgc  tta  tgt  cct  aat  agt  ctt  tta  gca  aat  ttt  ata  gaa  cta  gcg      672
Tyr  Cys  Leu  Cys  Pro  Asn  Ser  Leu  Leu  Ala  Asn  Phe  Ile  Glu  Leu  Ala
210                      215                      220 cca  aat  tta  aat  tca  aat  ttt  atc  ata  caa  gaa  aaa  aat  aac  tac  act      720
Pro  Asn  Leu  Asn  Ser  Asn  Phe  Ile  Ile  Gln  Glu  Lys  Asn  Asn  Tyr  Thr
225                      230                      235                      240 aaa  gat  ata  ctc  ata  cct  tct  agt  gag  gct  tat  gga  aaa  ttt  tca  aaa      768
Lys  Asp  Ile  Leu  Ile  Pro  Ser  Ser  Glu  Ala  Tyr  Gly  Lys  Phe  Ser  Lys
               245                      250                      255 aat  att  aat  ttt  aaa  aaa  ata  aaa  att  aaa  gaa  aat  gtt  tat  tac  aag      816
Asn  Ile  Asn  Phe  Lys  Lys  Ile  Lys  Ile  Lys  Glu  Asn  Val  Tyr  Tyr  Lys
          260                      265                      270 ttg  ata  aaa  gat  cta  tta  aga  tta  cct  agt  gat  ata  aag  cat  tat  ttc      864
Leu  Ile  Lys  Asp  Leu  Leu  Arg  Leu  Pro  Ser  Asp  Ile  Lys  His  Tyr  Phe
     275                      280                      285 aaa  gga  aaa                                                                        873
Lys  Gly  Lys
     290

<210> SEQ ID NO 14
<211> LENGTH: 291
<212> TYPE: PRT
<213> ORGANISM: Campylobacter jejuni
<220> FEATURE:
<223> OTHER INFORMATION: Campylobacter alpha-2,3/alpha
      2,8-sialyltransferase II (CstII) from C. jejuni O:36

<400> SEQUENCE: 14

Met  Lys  Lys  Val  Ile  Ile  Ala  Gly  Asn  Gly  Pro  Ser  Leu  Lys  Glu  Ile
 1                   5                      10                      15
```

```
Asp Tyr Ser Arg Leu Pro Asn Asp Phe Asp Val Phe Arg Cys Asn Gln
            20                  25                  30

Phe Tyr Phe Glu Asp Lys Tyr Tyr Leu Gly Lys Lys Cys Lys Thr Val
        35                  40                  45

Phe Tyr Thr Pro Asn Phe Phe Phe Glu Gln Tyr Tyr Thr Leu Lys His
    50                  55                  60

Leu Ile Gln Asn Gln Glu Tyr Glu Thr Glu Leu Ile Met Cys Ser Asn
65                  70                  75                  80

Tyr Asn Gln Ala His Leu Glu Asn Glu Asn Phe Val Lys Thr Phe Tyr
                85                  90                  95

Asp Tyr Phe Pro Asp Ala His Leu Gly Tyr Asp Phe Lys Gln Leu
            100                 105                 110

Lys Glu Phe Asn Ala Tyr Phe Lys Phe His Glu Ile Tyr Phe Asn Gln
        115                 120                 125

Arg Ile Thr Ser Gly Val Tyr Met Cys Ala Val Ala Ile Ala Leu Gly
    130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Glu Asn Leu Leu Lys Leu Ala Pro
                165                 170                 175

Asp Phe Lys Asn Asp Arg Ser His Tyr Ile Gly His Ser Lys Asn Thr
            180                 185                 190

Asp Ile Lys Ala Leu Glu Phe Leu Glu Lys Thr Tyr Lys Ile Lys Leu
        195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Ser Lys
                245                 250                 255

Asn Ile Asn Phe Lys Lys Ile Lys Ile Lys Glu Asn Val Tyr Tyr Lys
            260                 265                 270

Leu Ile Lys Asp Leu Leu Arg Leu Pro Ser Asp Ile Lys His Tyr Phe
        275                 280                 285

Lys Gly Lys
    290

<210> SEQ ID NO 15
<211> LENGTH: 1170
<212> TYPE: DNA
<213> ORGANISM: Campylobacter jejuni
<220> FEATURE:
<223> OTHER INFORMATION: glycosyltransferase from C. jejuni strain
      OH4384 (ORF 4a of lipooligosaccharide (LOS) biosynthesis
      locus)

<400> SEQUENCE: 15
atgaagaaaa taggtgtagt tataccaatc tataatgtag aaaaatattt aagagaatgt      60
ttagatagcg ttatcaatca aacttatact aacttagaaa tcatacttgt caatgatggt     120
agcacagatg aacactcact caatattgca aagaatata ccttaaaaga taaagaata      180 actcttttg ataagaaaaa tgggggttta agttcagcta gaaatatagg tatagaatac      240
tttagcgggg aatataaatt aaaaaacaaa actcaacata taaagagaaaa ttctttaata     300 gaatttcaat tggatggtaa taatccttat aatatatata agcatataa aagctctcaa     360
```

```
gcttttaata atgaaaaaga tttaaccaat tttacttacc ctagtataga ttatattata      420
ttcttagata gtgataatta ttggaaacta aactgcatag aagaatgcgt tataagaatg      480
aaaaatgtgg atgtattgtg gtttgaccat gattgcacct atgaagacaa tataaaaaat      540
aagcacaaaa aaacaaggat ggaaattttt gattttaaaa agaatgtat  aatcactcca      600 aaagaatatg caaatcgagc attaagtgta ggatctagag atatttcttt tggatggaat      660
ggaatgattg attttaattt tttaaagcaa attaaactta aatttataaa tttattatc      720 aatgaagata tacactttgg gataattttg tttgctagtg ctaataaaat ttatgtttta      780
tcacaaaagt tgtatttgtg tcgtttaaga gcaaacagta tatcaaatca tgataagaag      840
attacaaaag caaatgtgtc agagtatttt aaagatatat atgaaacttt cggggaaaac      900
gctaaggaag caaaaaatta tttaaaagca gcaagcaggg ttataactgc tttaaaattg      960
atagaatttt ttaaagatca aaaaaacgaa aatgcacttg ctataaaaga aacatttta      1020 ccttgctatg ccaaaaaagc tttaatgatt aaaaaattta aaaagatcc  tttaaattta      1080 aaggaacaat tagttttaat taaaccttt  attcaaacaa aacttcctta tgatatttgg      1140
aaattttggc aaaaaataaa aaatattta                                        1170
```

<210> SEQ ID NO 16
<211> LENGTH: 1044
<212> TYPE: DNA
<213> ORGANISM: Campylobacter jejuni
<220> FEATURE:
<221> NAME/KEY: CDS
<222> LOCATION: (1)..(1044)
<223> OTHER INFORMATION: beta-1,4 N-acetylgalactosaminyl (GalNAc)
      transferase from C. jejuni strain OH4384 (ORF 5a
      of lipooligosaccharide (LOS) biosynthesis locus)

<400> SEQUENCE: 16

```
atg cta ttt caa tca tac ttt gtg aaa ata att tgc tta ttc atc cct       48
Met Leu Phe Gln Ser Tyr Phe Val Lys Ile Ile Cys Leu Phe Ile Pro
 1               5                  10                  15 ttt aga aaa att aga cat aaa ata aaa aaa aca ttt tta cta aaa aac       96
Phe Arg Lys Ile Arg His Lys Ile Lys Lys Thr Phe Leu Leu Lys Asn
                20                  25                  30 ata caa cga gat aaa atc gat tct tat tta cca aaa aaa act ctt gtg      144
Ile Gln Arg Asp Lys Ile Asp Ser Tyr Leu Pro Lys Lys Thr Leu Val
            35                  40                  45 caa att aat aaa tac aac aat gaa gat tta att aaa ctt aat aaa gct      192
Gln Ile Asn Lys Tyr Asn Asn Glu Asp Leu Ile Lys Leu Asn Lys Ala
        50                  55                  60 att ata ggg gag ggg cat aaa gga tat ttt aat tat gat gaa aaa tct      240
Ile Ile Gly Glu Gly His Lys Gly Tyr Phe Asn Tyr Asp Glu Lys Ser
65                  70                  75                  80 aaa gat cca aaa tct cct ttg aat cct tgg gct ttt ata cga gta aaa      288
Lys Asp Pro Lys Ser Pro Leu Asn Pro Trp Ala Phe Ile Arg Val Lys
                85                  90                  95 aat gaa gct att acc tta aaa gct tct ctt gaa agc ata ttg cct gct      336
Asn Glu Ala Ile Thr Leu Lys Ala Ser Leu Glu Ser Ile Leu Pro Ala
                100                 105                 110 atc caa aga ggt gtt ata gga tat aat gat tgt acc gat gga agt gaa      384
Ile Gln Arg Gly Val Ile Gly Tyr Asn Asp Cys Thr Asp Gly Ser Glu
            115                 120                 125 gaa ata att cta gaa ttt tgc aaa caa tat cct tca ttt ata cca ata      432
Glu Ile Ile Leu Glu Phe Cys Lys Gln Tyr Pro Ser Phe Ile Pro Ile
        130                 135                 140 aaa tat cct tat gaa att caa att caa aac cca aaa tca gaa gaa aat      480
```

```
Lys Tyr Pro Tyr Glu Ile Gln Ile Gln Asn Pro Lys Ser Glu Glu Asn
145                 150                 155                 160 aaa ctc tat agc tat tat aat tat gtt gca agt ttt ata cca aaa gat      528
Lys Leu Tyr Ser Tyr Tyr Asn Tyr Val Ala Ser Phe Ile Pro Lys Asp
                165                 170                 175 gag tgg ctt ata aaa ata gat gtg gat cat atc tat gat gct aaa aaa      576
Glu Trp Leu Ile Lys Ile Asp Val Asp His Ile Tyr Asp Ala Lys Lys
            180                 185                 190 ctt tat aaa agc ttc tat ata cca aaa aac aaa tat gat gta gtt agt      624
Leu Tyr Lys Ser Phe Tyr Ile Pro Lys Asn Lys Tyr Asp Val Val Ser
        195                 200                 205 tat tca agg gtt gat att cac tat ttt aat gat aat ttt ttt ctt tgt      672
Tyr Ser Arg Val Asp Ile His Tyr Phe Asn Asp Asn Phe Phe Leu Cys
    210                 215                 220 aaa gat aat aat ggc aat ata ttg aaa gaa cca gga gat tgc ttg ctt      720
Lys Asp Asn Asn Gly Asn Ile Leu Lys Glu Pro Gly Asp Cys Leu Leu
225                 230                 235                 240 atc aat aat tat aac tta aaa tgg aaa gaa gta tta att gac aga atc      768
Ile Asn Asn Tyr Asn Leu Lys Trp Lys Glu Val Leu Ile Asp Arg Ile
                245                 250                 255 aat aac aat tgg aaa aaa gca aca aaa caa agt ttt tct tca aat ata      816
Asn Asn Asn Trp Lys Lys Ala Thr Lys Gln Ser Phe Ser Ser Asn Ile
            260                 265                 270 cac tct tta gag caa tta aag tat aaa cac agg ata tta ttt cac act      864
His Ser Leu Glu Gln Leu Lys Tyr Lys His Arg Ile Leu Phe His Thr
        275                 280                 285 gaa tta aat aat tat cat ttt cct ttt tta aaa aaa cat aga gct caa      912
Glu Leu Asn Asn Tyr His Phe Pro Phe Leu Lys Lys His Arg Ala Gln
    290                 295                 300 gat att tat aaa tat aat tgg ata agt att gaa gaa ttt aaa aaa ttc      960
Asp Ile Tyr Lys Tyr Asn Trp Ile Ser Ile Glu Glu Phe Lys Lys Phe
305                 310                 315                 320 tat tta caa aat att aat cat aaa ata gaa cct tct atg att tca aaa     1008
Tyr Leu Gln Asn Ile Asn His Lys Ile Glu Pro Ser Met Ile Ser Lys
                325                 330                 335 gaa act cta aaa aaa ata ttc tta aca ttg ttt taa                     1044
Glu Thr Leu Lys Lys Ile Phe Leu Thr Leu Phe
            340                 345

<210> SEQ ID NO 17
<211> LENGTH: 347
<212> TYPE: PRT
<213> ORGANISM: Campylobacter jejuni
<220> FEATURE:
<223> OTHER INFORMATION: beta-1,4 N-acetylgalactosaminyl (GalNAc)
      transferase from C. jejuni strain OH4384 (ORF 5a
      of lipooligosaccharide (LOS) biosynthesis locus)

<400> SEQUENCE: 17

Met Leu Phe Gln Ser Tyr Phe Val Lys Ile Ile Cys Leu Phe Ile Pro
1               5                   10                  15

Phe Arg Lys Ile Arg His Lys Ile Lys Lys Thr Phe Leu Leu Lys Asn
            20                  25                  30

Ile Gln Arg Asp Lys Ile Asp Ser Tyr Leu Pro Lys Lys Thr Leu Val
        35                  40                  45

Gln Ile Asn Lys Tyr Asn Asn Glu Asp Leu Ile Lys Leu Asn Lys Ala
    50                  55                  60

Ile Ile Gly Glu Gly His Lys Gly Tyr Phe Asn Tyr Asp Glu Lys Ser
65                  70                  75                  80

Lys Asp Pro Lys Ser Pro Leu Asn Pro Trp Ala Phe Ile Arg Val Lys
```

```
                     85                  90                  95
Asn Glu Ala Ile Thr Leu Lys Ala Ser Leu Glu Ser Ile Leu Pro Ala
                100                 105                 110

Ile Gln Arg Gly Val Ile Gly Tyr Asn Asp Cys Thr Asp Gly Ser Glu
            115                 120                 125

Glu Ile Ile Leu Glu Phe Cys Lys Gln Tyr Pro Ser Phe Ile Pro Ile
        130                 135                 140

Lys Tyr Pro Tyr Glu Ile Gln Ile Gln Asn Pro Lys Ser Glu Glu Asn
145                 150                 155                 160

Lys Leu Tyr Ser Tyr Tyr Asn Tyr Val Ala Ser Phe Ile Pro Lys Asp
                165                 170                 175

Glu Trp Leu Ile Lys Ile Asp Val Asp His Ile Tyr Asp Ala Lys Lys
            180                 185                 190

Leu Tyr Lys Ser Phe Tyr Ile Pro Lys Asn Lys Tyr Asp Val Val Ser
        195                 200                 205

Tyr Ser Arg Val Asp Ile His Tyr Phe Asn Asp Asn Phe Phe Leu Cys
    210                 215                 220

Lys Asp Asn Asn Gly Asn Ile Leu Lys Glu Pro Gly Asp Cys Leu Leu
225                 230                 235                 240

Ile Asn Asn Tyr Asn Leu Lys Trp Lys Glu Val Leu Ile Asp Arg Ile
                245                 250                 255

Asn Asn Asn Trp Lys Lys Ala Thr Lys Gln Ser Phe Ser Ser Asn Ile
            260                 265                 270

His Ser Leu Glu Gln Leu Lys Tyr Lys His Arg Ile Leu Phe His Thr
        275                 280                 285

Glu Leu Asn Asn Tyr His Phe Pro Phe Leu Lys Lys His Arg Ala Gln
    290                 295                 300

Asp Ile Tyr Lys Tyr Asn Trp Ile Ser Ile Glu Glu Phe Lys Lys Phe
305                 310                 315                 320

Tyr Leu Gln Asn Ile Asn His Lys Ile Glu Pro Ser Met Ile Ser Lys
                325                 330                 335

Glu Thr Leu Lys Lys Ile Phe Leu Thr Leu Phe
            340                 345

<210> SEQ ID NO 18
<211> LENGTH: 1608
<212> TYPE: DNA
<213> ORGANISM: Campylobacter jejuni
<220> FEATURE:
<221> NAME/KEY: CDS
<222> LOCATION: (1)..(1608)
<223> OTHER INFORMATION: beta-1,4 N-acetylgalactosaminyl (GalNAc)
      transferase from C. jejuni O:1

<400> SEQUENCE: 18 atg act ttg ttt tat aaa att ata gct ttt tta aga ttg ctt aaa att      48
Met Thr Leu Phe Tyr Lys Ile Ile Ala Phe Leu Arg Leu Leu Lys Ile
  1               5                  10                  15 gat aaa aaa tta aaa ttt gat aat gaa tat ttt tta aac tta aat aaa      96
Asp Lys Lys Leu Lys Phe Asp Asn Glu Tyr Phe Leu Asn Leu Asn Lys
             20                  25                  30 aaa atc tac aat gaa aag cat aaa ggt ttt ttt gat ttt gat cca aac     144
Lys Ile Tyr Asn Glu Lys His Lys Gly Phe Phe Asp Phe Asp Pro Asn
         35                  40                  45 tca aaa gat aca aaa tct cct tta aat cca tgg gct ttt ata aga gta     192
Ser Lys Asp Thr Lys Ser Pro Leu Asn Pro Trp Ala Phe Ile Arg Val
     50                  55                  60
```

```
aaa aat gaa gcc act act tta aga gta tca ctt gaa agt atg tta cct      240
Lys Asn Glu Ala Thr Thr Leu Arg Val Ser Leu Glu Ser Met Leu Pro
 65              70                  75                  80 gcc ata caa aga ggt gtt ata gga tat aat gat tgt act gat gga agt      288
Ala Ile Gln Arg Gly Val Ile Gly Tyr Asn Asp Cys Thr Asp Gly Ser
                 85                  90                  95 gaa gaa att att ttg gaa ttt tgc aaa caa tac cct tcg ttt ata cca      336
Glu Glu Ile Ile Leu Glu Phe Cys Lys Gln Tyr Pro Ser Phe Ile Pro
                100                 105                 110 gta aaa tat ccc cat gag gtg caa att gaa aat ccg caa agc gaa gaa      384
Val Lys Tyr Pro His Glu Val Gln Ile Glu Asn Pro Gln Ser Glu Glu
            115                 120                 125 aat aaa ctt cat agt tat tat aac tat gta gct agt ttt ata ccg caa      432
Asn Lys Leu His Ser Tyr Tyr Asn Tyr Val Ala Ser Phe Ile Pro Gln
        130                 135                 140 gat gag tgg ctt ata aaa ata gat gtg gat cat tac tat gat gca aaa      480
Asp Glu Trp Leu Ile Lys Ile Asp Val Asp His Tyr Tyr Asp Ala Lys
145                 150                 155                 160 aaa tta tat aag agt ttt tat atg gca tca aaa aat act gct gtt aga      528
Lys Leu Tyr Lys Ser Phe Tyr Met Ala Ser Lys Asn Thr Ala Val Arg
                165                 170                 175 ttt cca aga att aat ttt tta ata cta gat aaa att gta att caa aat      576
Phe Pro Arg Ile Asn Phe Leu Ile Leu Asp Lys Ile Val Ile Gln Asn
                180                 185                 190 ata gga gaa tgt ggt ttt atc gat gga ggg gat caa ttg tta att caa      624
Ile Gly Glu Cys Gly Phe Ile Asp Gly Gly Asp Gln Leu Leu Ile Gln
            195                 200                 205 aag tgc aat agt gta ttt ata gaa aga atg gtt tca aag caa agt cag      672
Lys Cys Asn Ser Val Phe Ile Glu Arg Met Val Ser Lys Gln Ser Gln
210                 215                 220 tgg att gat cct gaa aaa act gtg aaa gaa ttg tat tct gaa cag caa      720
Trp Ile Asp Pro Glu Lys Thr Val Lys Glu Leu Tyr Ser Glu Gln Gln
225                 230                 235                 240 att ata ccc aaa cat ata aaa atc tta caa gca gaa tta ctt caa tgg      768
Ile Ile Pro Lys His Ile Lys Ile Leu Gln Ala Glu Leu Leu Gln Trp
                245                 250                 255 cat ttt cct gct tta aaa tat cat aga aat gat tat caa aaa cat ttg      816
His Phe Pro Ala Leu Lys Tyr His Arg Asn Asp Tyr Gln Lys His Leu
            260                 265                 270 gat gct tta act tta gaa gat ttt aaa aaa atc cat tat aga cat aga      864
Asp Ala Leu Thr Leu Glu Asp Phe Lys Lys Ile His Tyr Arg His Arg
        275                 280                 285 aaa ata aag aaa ata aat tat aca atg ctt gat gaa aaa gta att cgt      912
Lys Ile Lys Lys Ile Asn Tyr Thr Met Leu Asp Glu Lys Val Ile Arg
290                 295                 300 gaa ata tta gat aaa ttt aaa ttg agt ggt aaa aaa atg act tta gct      960
Glu Ile Leu Asp Lys Phe Lys Leu Ser Gly Lys Lys Met Thr Leu Ala
305                 310                 315                 320 ata ata cct gct cga gct ggt tca aaa ggt ata aaa aat aaa aat tta     1008
Ile Ile Pro Ala Arg Ala Gly Ser Lys Gly Ile Lys Asn Lys Asn Leu
                325                 330                 335 gct ctt ttg cat gat agg cct ttg ttg tat tat act atc aat gca gca     1056
Ala Leu Leu His Asp Arg Pro Leu Leu Tyr Tyr Thr Ile Asn Ala Ala
            340                 345                 350 aaa aat tca aag tat gta gat aaa att gtt tta agt agt gat ggc gat     1104
Lys Asn Ser Lys Tyr Val Asp Lys Ile Val Leu Ser Ser Asp Gly Asp
        355                 360                 365 gat ata tta gaa tat gga caa act caa ggt gta gat gtg tta aaa aga     1152
Asp Ile Leu Glu Tyr Gly Gln Thr Gln Gly Val Asp Val Leu Lys Arg
370                 375                 380
```

```
cct aaa gaa tta gcg cta gat gat aca act agt gat aag gtt gta ttg      1200
Pro Lys Glu Leu Ala Leu Asp Asp Thr Thr Ser Asp Lys Val Val Leu
385                 390                 395                 400 cat acc ttg agt ttt tat aaa gat tat gaa aat att gtt tta tta caa      1248
His Thr Leu Ser Phe Tyr Lys Asp Tyr Glu Asn Ile Val Leu Leu Gln
                405                 410                 415 ccc act tct cct tta agg aca aat gta cat ata gat gaa gct ttt tta      1296
Pro Thr Ser Pro Leu Arg Thr Asn Val His Ile Asp Glu Ala Phe Leu
            420                 425                 430 aaa ttt aaa aat gaa aac tca aat gca tta ata agt gtt gta gaa tgt      1344
Lys Phe Lys Asn Glu Asn Ser Asn Ala Leu Ile Ser Val Val Glu Cys
        435                 440                 445 gat aat aaa att tta aaa gct ttt ata gat gat aat ggt aac tta aaa      1392
Asp Asn Lys Ile Leu Lys Ala Phe Ile Asp Asp Asn Gly Asn Leu Lys
    450                 455                 460 gga att tgt gat aac aaa tat cca ttt atg cct aga caa aaa tta cca      1440
Gly Ile Cys Asp Asn Lys Tyr Pro Phe Met Pro Arg Gln Lys Leu Pro
465                 470                 475                 480 aaa act tat atg agt aat ggt gca att tat ata gta aag tca aat tta      1488
Lys Thr Tyr Met Ser Asn Gly Ala Ile Tyr Ile Val Lys Ser Asn Leu
                485                 490                 495 ttt tta aat aac cca act ttt cta caa gaa aaa aca agt tgc tat ata      1536
Phe Leu Asn Asn Pro Thr Phe Leu Gln Glu Lys Thr Ser Cys Tyr Ile
            500                 505                 510 atg gac gaa aaa gct agt ttg gat ata gat aca aca gag gat tta aaa      1584
Met Asp Glu Lys Ala Ser Leu Asp Ile Asp Thr Thr Glu Asp Leu Lys
        515                 520                 525 aga gtt aat aat ata agc ttc tta                                      1608
Arg Val Asn Asn Ile Ser Phe Leu
    530                 535

<210> SEQ ID NO 19
<211> LENGTH: 536
<212> TYPE: PRT
<213> ORGANISM: Campylobacter jejuni
<223> OTHER INFORMATION: beta-1,4 N-acetylgalactosaminyl (GalNAc)

<400> SEQUENCE: 19

Met Thr Leu Phe Tyr Lys Ile Ile Ala Phe Leu Arg Leu Leu Lys Ile
1               5                   10                  15

Asp Lys Lys Leu Lys Phe Asp Asn Glu Tyr Phe Leu Asn Leu Asn Lys
            20                  25                  30

Lys Ile Tyr Asn Glu Lys His Lys Gly Phe Phe Asp Phe Asp Pro Asn
        35                  40                  45

Ser Lys Asp Thr Lys Ser Pro Leu Asn Pro Trp Ala Phe Ile Arg Val
    50                  55                  60

Lys Asn Glu Ala Thr Thr Leu Arg Val Ser Leu Glu Ser Met Leu Pro
65                  70                  75                  80

Ala Ile Gln Arg Gly Val Ile Gly Tyr Asn Asp Cys Thr Asp Gly Ser
                85                  90                  95

Glu Glu Ile Ile Leu Glu Phe Cys Lys Gln Tyr Pro Ser Phe Ile Pro
            100                 105                 110

Val Lys Tyr Pro His Glu Val Gln Ile Glu Asn Pro Gln Ser Glu Glu
        115                 120                 125

Asn Lys Leu His Ser Tyr Tyr Asn Tyr Val Ala Ser Phe Ile Pro Gln
    130                 135                 140

Asp Glu Trp Leu Ile Lys Ile Asp Val Asp His Tyr Tyr Asp Ala Lys
145                 150                 155                 160
```

```
Lys Leu Tyr Lys Ser Phe Tyr Met Ala Ser Lys Asn Thr Ala Val Arg
            165                 170                 175

Phe Pro Arg Ile Asn Phe Leu Ile Leu Asp Lys Ile Val Ile Gln Asn
        180                 185                 190

Ile Gly Glu Cys Gly Phe Ile Asp Gly Gly Asp Gln Leu Leu Ile Gln
    195                 200                 205

Lys Cys Asn Ser Val Phe Ile Glu Arg Met Val Ser Lys Gln Ser Gln
210                 215                 220

Trp Ile Asp Pro Glu Lys Thr Val Lys Glu Leu Tyr Ser Glu Gln Gln
225                 230                 235                 240

Ile Ile Pro Lys His Ile Lys Ile Leu Gln Ala Glu Leu Leu Gln Trp
                245                 250                 255

His Phe Pro Ala Leu Lys Tyr His Arg Asn Asp Tyr Gln Lys His Leu
            260                 265                 270

Asp Ala Leu Thr Leu Glu Asp Phe Lys Lys Ile His Tyr Arg His Arg
        275                 280                 285

Lys Ile Lys Lys Ile Asn Tyr Thr Met Leu Asp Glu Lys Val Ile Arg
    290                 295                 300

Glu Ile Leu Asp Lys Phe Lys Leu Ser Gly Lys Lys Met Thr Leu Ala
305                 310                 315                 320

Ile Ile Pro Ala Arg Ala Gly Ser Lys Gly Ile Lys Asn Lys Asn Leu
                325                 330                 335

Ala Leu Leu His Asp Arg Pro Leu Leu Tyr Tyr Thr Ile Asn Ala Ala
            340                 345                 350

Lys Asn Ser Lys Tyr Val Asp Lys Ile Val Leu Ser Ser Asp Gly Asp
        355                 360                 365

Asp Ile Leu Glu Tyr Gly Gln Thr Gln Gly Val Asp Val Leu Lys Arg
    370                 375                 380

Pro Lys Glu Leu Ala Leu Asp Asp Thr Thr Ser Asp Lys Val Val Leu
385                 390                 395                 400

His Thr Leu Ser Phe Tyr Lys Asp Tyr Glu Asn Ile Val Leu Leu Gln
                405                 410                 415

Pro Thr Ser Pro Leu Arg Thr Asn Val His Ile Asp Glu Ala Phe Leu
            420                 425                 430

Lys Phe Lys Asn Glu Asn Ser Asn Ala Leu Ile Ser Val Val Glu Cys
        435                 440                 445

Asp Asn Lys Ile Leu Lys Ala Phe Ile Asp Asn Gly Asn Leu Lys
450                 455                 460

Gly Ile Cys Asp Asn Lys Tyr Pro Phe Met Pro Arg Gln Lys Leu Pro
465                 470                 475                 480

Lys Thr Tyr Met Ser Asn Gly Ala Ile Tyr Ile Val Lys Ser Asn Leu
                485                 490                 495

Phe Leu Asn Asn Pro Thr Phe Leu Gln Glu Lys Thr Ser Cys Tyr Ile
            500                 505                 510

Met Asp Glu Lys Ala Ser Leu Asp Ile Asp Thr Thr Glu Asp Leu Lys
        515                 520                 525

Arg Val Asn Asn Ile Ser Phe Leu
530                 535

<210> SEQ ID NO 20
<211> LENGTH: 1056
<212> TYPE: DNA
<213> ORGANISM: Campylobacter jejuni
<220> FEATURE:
```

```
<221> NAME/KEY: CDS
<222> LOCATION: (1)..(1056)
<223> OTHER INFORMATION: beta-1,4 N-acetylgalactosaminyl (GalNAc)
      transferase from C. jejuni O:10

<400> SEQUENCE: 20 atg cta ttt caa tca tac ttt gtg aaa ata att tgc tta ttc atc cct      48
Met Leu Phe Gln Ser Tyr Phe Val Lys Ile Ile Cys Leu Phe Ile Pro
  1               5                  10                  15 ttt aga aaa att aga cat aaa ata aaa aaa aca ttt tta cta aaa aac      96
Phe Arg Lys Ile Arg His Lys Ile Lys Lys Thr Phe Leu Leu Lys Asn
             20                  25                  30 ata caa cga gat aaa atc gat tct tat cta cca aaa aaa act ctt ata    144
Ile Gln Arg Asp Lys Ile Asp Ser Tyr Leu Pro Lys Lys Thr Leu Ile
         35                  40                  45 caa att aat aaa tac aac aat gaa gat tta att aaa ctt aat aaa gct    192
Gln Ile Asn Lys Tyr Asn Asn Glu Asp Leu Ile Lys Leu Asn Lys Ala
     50                  55                  60 att ata ggg ggg ggg cat aaa gga tat ttt aat tat gat gaa aaa tct    240
Ile Ile Gly Gly Gly His Lys Gly Tyr Phe Asn Tyr Asp Glu Lys Ser
 65                  70                  75                  80 aaa gat cca aaa tct cct ttg aat cct tgg gct ttt ata cga gta aaa    288
Lys Asp Pro Lys Ser Pro Leu Asn Pro Trp Ala Phe Ile Arg Val Lys
                 85                  90                  95 aat gaa gct att acc tta aaa gct tct ctt gaa agc ata ttg cct gct    336
Asn Glu Ala Ile Thr Leu Lys Ala Ser Leu Glu Ser Ile Leu Pro Ala
            100                 105                 110 att caa aga ggt gtt ata gga tat aat gat tgc acc gat gga agt gaa    384
Ile Gln Arg Gly Val Ile Gly Tyr Asn Asp Cys Thr Asp Gly Ser Glu
        115                 120                 125 gaa ata att cta gaa ttt tgc aaa caa tat cct tca ttt ata cca ata    432
Glu Ile Ile Leu Glu Phe Cys Lys Gln Tyr Pro Ser Phe Ile Pro Ile
    130                 135                 140 aaa tat cct tat gaa att caa att caa aac cca aaa tca gaa gaa aat    480
Lys Tyr Pro Tyr Glu Ile Gln Ile Gln Asn Pro Lys Ser Glu Glu Asn
145                 150                 155                 160 aaa ctc tat agc tat tat aat tat gtt gca agt ttt ata cca aaa gat    528
Lys Leu Tyr Ser Tyr Tyr Asn Tyr Val Ala Ser Phe Ile Pro Lys Asp
                165                 170                 175 gag tgg ctc ata aaa ata gat gtg gat cat tat tat gat gca aaa aaa    576
Glu Trp Leu Ile Lys Ile Asp Val Asp His Tyr Tyr Asp Ala Lys Lys
            180                 185                 190 tta tat aag agt ttt tat ata cct aga aaa aat tat cat gta att agt    624
Leu Tyr Lys Ser Phe Tyr Ile Pro Arg Lys Asn Tyr His Val Ile Ser
        195                 200                 205 tac tct agg ata gat ttt ata ttt aat gaa gaa aaa ttt tat gtt tat    672
Tyr Ser Arg Ile Asp Phe Ile Phe Asn Glu Glu Lys Phe Tyr Val Tyr
    210                 215                 220 cgg aat aag gag ggg gag att tta aaa gct cct gga gat tgt tta gca    720
Arg Asn Lys Glu Gly Glu Ile Leu Lys Ala Pro Gly Asp Cys Leu Ala
225                 230                 235                 240 ata caa aac act aac tta ttt tgg aaa gaa ata ctt att gaa gat gat    768
Ile Gln Asn Thr Asn Leu Phe Trp Lys Glu Ile Leu Ile Glu Asp Asp
                245                 250                 255 aca ttt aag tgg aat act gca aaa aat aat ata gag aat gca aaa tca    816
Thr Phe Lys Trp Asn Thr Ala Lys Asn Asn Ile Glu Asn Ala Lys Ser
            260                 265                 270 tat gaa att tta aaa gtt aga aat aga att tat ttt act aca gaa ctt    864
Tyr Glu Ile Leu Lys Val Arg Asn Arg Ile Tyr Phe Thr Thr Glu Leu
        275                 280                 285
```

-continued

```
aat aat tat cat ttt cca ttt ata aaa aat tat aga aaa aat gat tat      912
Asn Asn Tyr His Phe Pro Phe Ile Lys Asn Tyr Arg Lys Asn Asp Tyr
290                 295                 300 aag cag tta aat tgg gtt agc tta gat gat ttt att aaa aat tat aaa      960
Lys Gln Leu Asn Trp Val Ser Leu Asp Asp Phe Ile Lys Asn Tyr Lys
305                 310                 315                 320 gaa aaa tta aaa aat caa ata gat ttt aaa atg cta gaa tac aaa aca     1008
Glu Lys Leu Lys Asn Gln Ile Asp Phe Lys Met Leu Glu Tyr Lys Thr
                325                 330                 335 tta aaa aaa gtg tac aaa aag ctt aca tct tca gca agc gat aaa att     1056
Leu Lys Lys Val Tyr Lys Lys Leu Thr Ser Ser Ala Ser Asp Lys Ile
            340                 345                 350
```

<210> SEQ ID NO 21
<211> LENGTH: 352
<212> TYPE: PRT
<213> ORGANISM: Campylobacter jejuni
<220> FEATURE:
<223> OTHER INFORMATION: beta-1,4 N-acetylgalactosaminyl (GalNAc)
      transferase from C. jejuni O:10

<400> SEQUENCE: 21

```
Met Leu Phe Gln Ser Tyr Phe Val Lys Ile Ile Cys Leu Phe Ile Pro
1               5                   10                  15

Phe Arg Lys Ile Arg His Lys Ile Lys Lys Thr Phe Leu Leu Lys Asn
            20                  25                  30

Ile Gln Arg Asp Lys Ile Asp Ser Tyr Leu Pro Lys Lys Thr Leu Ile
        35                  40                  45

Gln Ile Asn Lys Tyr Asn Asn Glu Asp Leu Ile Lys Leu Asn Lys Ala
    50                  55                  60

Ile Ile Gly Gly His Lys Gly Tyr Phe Asn Tyr Asp Glu Lys Ser
65                  70                  75                  80

Lys Asp Pro Lys Ser Pro Leu Asn Pro Trp Ala Phe Ile Arg Val Lys
                85                  90                  95

Asn Glu Ala Ile Thr Leu Lys Ala Ser Leu Glu Ser Ile Leu Pro Ala
            100                 105                 110

Ile Gln Arg Gly Val Ile Gly Tyr Asn Asp Cys Thr Asp Gly Ser Glu
        115                 120                 125

Glu Ile Ile Leu Glu Phe Cys Lys Gln Tyr Pro Ser Phe Ile Pro Ile
    130                 135                 140

Lys Tyr Pro Tyr Glu Ile Gln Ile Gln Asn Pro Lys Ser Glu Glu Asn
145                 150                 155                 160

Lys Leu Tyr Ser Tyr Tyr Asn Tyr Val Ala Ser Phe Ile Pro Lys Asp
                165                 170                 175

Glu Trp Leu Ile Lys Ile Asp Val Asp His Tyr Tyr Asp Ala Lys Lys
            180                 185                 190

Leu Tyr Lys Ser Phe Tyr Ile Pro Arg Lys Asn Tyr His Val Ile Ser
        195                 200                 205

Tyr Ser Arg Ile Asp Phe Ile Phe Asn Glu Glu Lys Phe Tyr Val Tyr
    210                 215                 220

Arg Asn Lys Glu Gly Glu Ile Leu Lys Ala Pro Gly Asp Cys Leu Ala
225                 230                 235                 240

Ile Gln Asn Thr Asn Leu Phe Trp Lys Glu Ile Leu Ile Glu Asp Asp
                245                 250                 255

Thr Phe Lys Trp Asn Thr Ala Lys Asn Asn Ile Glu Asn Ala Lys Ser
            260                 265                 270

Tyr Glu Ile Leu Lys Val Arg Asn Arg Ile Tyr Phe Thr Thr Glu Leu
```

```
                    275                 280                 285
Asn Asn Tyr His Phe Pro Phe Ile Lys Asn Tyr Arg Lys Asn Asp Tyr
            290                 295                 300

Lys Gln Leu Asn Trp Val Ser Leu Asp Asp Phe Ile Lys Asn Tyr Lys
305                 310                 315                 320

Glu Lys Leu Lys Asn Gln Ile Asp Phe Lys Met Leu Glu Tyr Lys Thr
                325                 330                 335

Leu Lys Lys Val Tyr Lys Lys Leu Thr Ser Ser Ala Ser Asp Lys Ile
            340                 345                 350

<210> SEQ ID NO 22
<211> LENGTH: 945
<212> TYPE: DNA
<213> ORGANISM: Campylobacter jejuni
<220> FEATURE:
<221> NAME/KEY: CDS
<222> LOCATION: (1)..(945)
<223> OTHER INFORMATION: beta-1,4 N-acetylgalactosaminyl (GalNAc)
      transferase from C. jejuni O:36

<400> SEQUENCE: 22 atg ctt aaa aaa atc att tct tta tat aaa aga tac tcg att tct aaa      48
Met Leu Lys Lys Ile Ile Ser Leu Tyr Lys Arg Tyr Ser Ile Ser Lys
  1               5                  10                  15 aaa ttg gtt tta gat aat gag cat ttc att aag gaa aat aaa aac atc     96
Lys Leu Val Leu Asp Asn Glu His Phe Ile Lys Glu Asn Lys Asn Ile
                 20                  25                  30 tat gga aaa aaa cat aag ggc ttt ttt gac ttt gat gaa aag gct aag    144
Tyr Gly Lys Lys His Lys Gly Phe Phe Asp Phe Asp Glu Lys Ala Lys
             35                  40                  45 gat gtg aaa tca ccc ctt aat cct tgg gga ttt atc agg gtt aaa aat    192
Asp Val Lys Ser Pro Leu Asn Pro Trp Gly Phe Ile Arg Val Lys Asn
         50                  55                  60 gaa gct tta acc cta aga gtt tct tta gaa agt ata cta cct gct tta    240
Glu Ala Leu Thr Leu Arg Val Ser Leu Glu Ser Ile Leu Pro Ala Leu
 65                  70                  75                  80 caa aga gga att ata gct tac aac gac tgt gat gat ggg agt gaa gag    288
Gln Arg Gly Ile Ile Ala Tyr Asn Asp Cys Asp Asp Gly Ser Glu Glu
                     85                  90                  95 ctt att tta gaa ttt tgc aag caa tat ccc aac ttc att gct aaa aaa    336
Leu Ile Leu Glu Phe Cys Lys Gln Tyr Pro Asn Phe Ile Ala Lys Lys
                100                 105                 110 tat cct tat aaa gta gat cta gaa aat cct aaa aat gaa gaa aat aaa    384
Tyr Pro Tyr Lys Val Asp Leu Glu Asn Pro Lys Asn Glu Glu Asn Lys
            115                 120                 125 ctt tac tct tat tac aat tgg gca gca tct ttt ata ccc tta gat gag    432
Leu Tyr Ser Tyr Tyr Asn Trp Ala Ala Ser Phe Ile Pro Leu Asp Glu
        130                 135                 140 tgg ttt ata aaa atc gat gtg gat cat tac tac gat gcc aag aag ctt    480
Trp Phe Ile Lys Ile Asp Val Asp His Tyr Tyr Asp Ala Lys Lys Leu
145                 150                 155                 160 tat aag agt ttt tat agg att gat caa gaa aat aaa gcc tta tgc tac    528
Tyr Lys Ser Phe Tyr Arg Ile Asp Gln Glu Asn Lys Ala Leu Cys Tyr
                165                 170                 175 cca aga att aat ttt ata atc tta aat gga aat att tat gtg caa aat    576
Pro Arg Ile Asn Phe Ile Ile Leu Asn Gly Asn Ile Tyr Val Gln Asn
                180                 185                 190 agt gga aat tat gga ttc ata ggg ggg ggg gat caa ctc ttg att aaa    624
Ser Gly Asn Tyr Gly Phe Ile Gly Gly Gly Asp Gln Leu Leu Ile Lys
            195                 200                 205
```

```
aga aga aat agt agc ttt ata gaa aga agg gtt tca aaa aaa agc caa       672
Arg Arg Asn Ser Ser Phe Ile Glu Arg Arg Val Ser Lys Lys Ser Gln
    210                 215                 220 tgg ata gat cct aag gga ctt ata gaa gaa ctc tac tcc gag caa caa       720
Trp Ile Asp Pro Lys Gly Leu Ile Glu Glu Leu Tyr Ser Glu Gln Gln
225                 230                 235                 240 gtc tta tct caa gga gtg aaa ata cta caa gct ccc cta ctt cag tgg       768
Val Leu Ser Gln Gly Val Lys Ile Leu Gln Ala Pro Leu Leu Gln Trp
                245                 250                 255 cat ttt cct gcc tta aaa tac cgc cga aac gat tac caa caa tat tta       816
His Phe Pro Ala Leu Lys Tyr Arg Arg Asn Asp Tyr Gln Gln Tyr Leu
            260                 265                 270 gat atc ttg agt tta gaa gaa ttt cag gcc ttt cat cgt aag agc aaa       864
Asp Ile Leu Ser Leu Glu Glu Phe Gln Ala Phe His Arg Lys Ser Lys
        275                 280                 285 gag gct aaa aaa ata gac ttt gcc atg cta aaa cgc cct gta atc gag       912
Glu Ala Lys Lys Ile Asp Phe Ala Met Leu Lys Arg Pro Val Ile Glu
290                 295                 300 caa ata tta aag aaa ttt caa gga gag ata aaa                           945
Gln Ile Leu Lys Lys Phe Gln Gly Glu Ile Lys
305                 310                 315

<210> SEQ ID NO 23
<211> LENGTH: 315
<212> TYPE: PRT
<213> ORGANISM: Campylobacter jejuni
<220> FEATURE:
<223> OTHER INFORMATION: beta-1,4 N-acetylgalactosaminyl (GalNAc)
      transferase from C. jejuni O:36

<400> SEQUENCE: 23

Met Leu Lys Lys Ile Ile Ser Leu Tyr Lys Arg Tyr Ser Ile Ser Lys
1               5                   10                  15

Lys Leu Val Leu Asp Asn Glu His Phe Ile Lys Glu Asn Lys Asn Ile
            20                  25                  30

Tyr Gly Lys Lys His Lys Gly Phe Phe Asp Phe Asp Glu Lys Ala Lys
        35                  40                  45

Asp Val Lys Ser Pro Leu Asn Pro Trp Gly Phe Ile Arg Val Lys Asn
    50                  55                  60

Glu Ala Leu Thr Leu Arg Val Ser Leu Glu Ser Ile Leu Pro Ala Leu
65                  70                  75                  80

Gln Arg Gly Ile Ile Ala Tyr Asn Asp Cys Asp Asp Gly Ser Glu Glu
                85                  90                  95

Leu Ile Leu Glu Phe Cys Lys Gln Tyr Pro Asn Phe Ile Ala Lys Lys
            100                 105                 110

Tyr Pro Tyr Lys Val Asp Leu Glu Asn Pro Lys Asn Glu Glu Asn Lys
        115                 120                 125

Leu Tyr Ser Tyr Asn Trp Ala Ala Ser Phe Ile Pro Leu Asp Glu
    130                 135                 140

Trp Phe Ile Lys Ile Asp Val Asp His Tyr Tyr Asp Ala Lys Lys Leu
145                 150                 155                 160

Tyr Lys Ser Phe Tyr Arg Ile Asp Gln Glu Asn Lys Ala Leu Cys Tyr
                165                 170                 175

Pro Arg Ile Asn Phe Ile Ile Leu Asn Gly Asn Ile Tyr Val Gln Asn
            180                 185                 190

Ser Gly Asn Tyr Gly Phe Ile Gly Gly Gly Asp Gln Leu Leu Ile Lys
        195                 200                 205

Arg Arg Asn Ser Ser Phe Ile Glu Arg Arg Val Ser Lys Lys Ser Gln
```

```
                210                 215                 220
Trp Ile Asp Pro Lys Gly Leu Ile Glu Glu Leu Tyr Ser Glu Gln Gln
225                 230                 235                 240

Val Leu Ser Gln Gly Val Lys Ile Leu Gln Ala Pro Leu Leu Gln Trp
                245                 250                 255

His Phe Pro Ala Leu Lys Tyr Arg Arg Asn Asp Tyr Gln Gln Tyr Leu
            260                 265                 270

Asp Ile Leu Ser Leu Glu Glu Phe Gln Ala Phe His Arg Lys Ser Lys
            275                 280                 285

Glu Ala Lys Lys Ile Asp Phe Ala Met Leu Lys Arg Pro Val Ile Glu
        290                 295                 300

Gln Ile Leu Lys Lys Phe Gln Gly Glu Ile Lys
305                 310                 315

<210> SEQ ID NO 24
<211> LENGTH: 1608
<212> TYPE: DNA
<213> ORGANISM: Campylobacter jejuni
<220> FEATURE:
<221> NAME/KEY: CDS
<222> LOCATION: (1)..(1608)
<223> OTHER INFORMATION: beta-1,4 N-acetylgalactosaminyl (GalNAc)
      transferase from C. jejuni NCTC 11168

<400> SEQUENCE: 24 atg act ttg ttt tat aaa att ata gct ttt tta aga ttg ctt aaa att      48
Met Thr Leu Phe Tyr Lys Ile Ile Ala Phe Leu Arg Leu Leu Lys Ile
 1               5                  10                  15 gat aaa aaa tta aaa ttt gat aat gaa tat ttt tta aac tta aat aaa      96
Asp Lys Lys Leu Lys Phe Asp Asn Glu Tyr Phe Leu Asn Leu Asn Lys
             20                  25                  30 aaa atc tac gat gaa aag cat aaa ggt ttt ttt gat ttt gat cca aac     144
Lys Ile Tyr Asp Glu Lys His Lys Gly Phe Phe Asp Phe Asp Pro Asn
         35                  40                  45 tca aaa gat aca aaa tct cct tta aat cca tgg gct ttt ata aga gta     192
Ser Lys Asp Thr Lys Ser Pro Leu Asn Pro Trp Ala Phe Ile Arg Val
     50                  55                  60 aaa aat gaa gcc act act tta aga gta tca ctt gaa agt atg tta cct     240
Lys Asn Glu Ala Thr Thr Leu Arg Val Ser Leu Glu Ser Met Leu Pro
 65                  70                  75                  80 gcc ata caa aga ggt gtt ata gga tat aat gat tgt act gat gga agt     288
Ala Ile Gln Arg Gly Val Ile Gly Tyr Asn Asp Cys Thr Asp Gly Ser
                 85                  90                  95 gaa gaa att att ttg gaa ttt tgc aaa caa tac cct tcg ttt ata cca     336
Glu Glu Ile Ile Leu Glu Phe Cys Lys Gln Tyr Pro Ser Phe Ile Pro
            100                 105                 110 gta aaa tat ccc cat gag gtg caa att gaa aat ccg caa agc gaa gaa     384
Val Lys Tyr Pro His Glu Val Gln Ile Glu Asn Pro Gln Ser Glu Glu
        115                 120                 125 aat aaa ctt cat agt tat tat aac tat gta gct agt ttt ata ccg caa     432
Asn Lys Leu His Ser Tyr Tyr Asn Tyr Val Ala Ser Phe Ile Pro Gln
    130                 135                 140 gat gag tgg ctt ata aaa ata gat gtg gat cat tac tat gat gca aaa     480
Asp Glu Trp Leu Ile Lys Ile Asp Val Asp His Tyr Tyr Asp Ala Lys
145                 150                 155                 160 aaa tta tat aag agt ttt tat atg gca tca aaa aat act gct gtt aga     528
Lys Leu Tyr Lys Ser Phe Tyr Met Ala Ser Lys Asn Thr Ala Val Arg
                165                 170                 175 ttt cca aga att aat ttt tta ata cta gat aaa att gta att caa aat     576
Phe Pro Arg Ile Asn Phe Leu Ile Leu Asp Lys Ile Val Ile Gln Asn
```

```
                    180                 185                 190
ata gga gaa tgt ggt ttt atc gat gga ggg gat caa ttg tta att caa    624
Ile Gly Glu Cys Gly Phe Ile Asp Gly Gly Asp Gln Leu Leu Ile Gln
            195                 200                 205 aag tgc aat agt gta ttt ata gaa aga atg gtt tca aag caa agt cag    672
Lys Cys Asn Ser Val Phe Ile Glu Arg Met Val Ser Lys Gln Ser Gln
210                 215                 220 tgg att gat cct gaa aaa act gtg aaa gaa ttg tat tct gaa cag caa    720
Trp Ile Asp Pro Glu Lys Thr Val Lys Glu Leu Tyr Ser Glu Gln Gln
225                 230                 235                 240 att ata ccc aaa cat ata aaa atc tta caa gca gaa tta ctt caa tgg    768
Ile Ile Pro Lys His Ile Lys Ile Leu Gln Ala Glu Leu Leu Gln Trp
            245                 250                 255 cat ttt cct gct tta aaa tat cat aga aat gat tat caa aaa cat ttg    816
His Phe Pro Ala Leu Lys Tyr His Arg Asn Asp Tyr Gln Lys His Leu
            260                 265                 270 gat gct tta act tta gaa gat ttt aaa aaa atc cat tat aga cat aga    864
Asp Ala Leu Thr Leu Glu Asp Phe Lys Lys Ile His Tyr Arg His Arg
            275                 280                 285 aaa ata aag aaa ata aat tat aca atg ctt gat gaa aaa gta att cgt    912
Lys Ile Lys Lys Ile Asn Tyr Thr Met Leu Asp Glu Lys Val Ile Arg
290                 295                 300 gaa ata tta gat aaa ttt aaa ttg agt ggt aaa aaa atg act tta gct    960
Glu Ile Leu Asp Lys Phe Lys Leu Ser Gly Lys Lys Met Thr Leu Ala
305                 310                 315                 320 ata ata cct gct cga gct ggt tca aaa ggt ata aaa aat aaa aat tta   1008
Ile Ile Pro Ala Arg Ala Gly Ser Lys Gly Ile Lys Asn Lys Asn Leu
            325                 330                 335 gct ctt ttg cat gat agg cct ttg ttg tat tat act atc aat gca gca   1056
Ala Leu Leu His Asp Arg Pro Leu Leu Tyr Tyr Thr Ile Asn Ala Ala
            340                 345                 350 aaa aat tca aag tat gta gat aaa att gtt tta agt agt gat ggc gat   1104
Lys Asn Ser Lys Tyr Val Asp Lys Ile Val Leu Ser Ser Asp Gly Asp
            355                 360                 365 gat ata tta gaa tat gga caa act caa ggt gta gat gtg tta aaa aga   1152
Asp Ile Leu Glu Tyr Gly Gln Thr Gln Gly Val Asp Val Leu Lys Arg
370                 375                 380 cct aaa gaa tta gcg cta gat gat aca act agt gat aag gtt gta ttg   1200
Pro Lys Glu Leu Ala Leu Asp Asp Thr Thr Ser Asp Lys Val Val Leu
385                 390                 395                 400 cat acc ttg agt ttt tat aaa gat tat gaa aat att gtt tta tta caa   1248
His Thr Leu Ser Phe Tyr Lys Asp Tyr Glu Asn Ile Val Leu Leu Gln
                405                 410                 415 ccc act tct cct tta agg aca aat gta cat ata gat gaa gct ttt tta   1296
Pro Thr Ser Pro Leu Arg Thr Asn Val His Ile Asp Glu Ala Phe Leu
            420                 425                 430 aaa ttt aaa aat gaa aac tca aat gca tta ata agt gtt gta gaa tgt   1344
Lys Phe Lys Asn Glu Asn Ser Asn Ala Leu Ile Ser Val Val Glu Cys
            435                 440                 445 gat aat aaa att tta aaa gct ttt ata gat gat aat ggt aac tta aaa   1392
Asp Asn Lys Ile Leu Lys Ala Phe Ile Asp Asp Asn Gly Asn Leu Lys
450                 455                 460 gga att tgt gat aac aaa tat cca ttt atg cct aga caa aaa tta cca   1440
Gly Ile Cys Asp Asn Lys Tyr Pro Phe Met Pro Arg Gln Lys Leu Pro
465                 470                 475                 480 aaa act tat atg agt aat ggt gca att tat ata gta aag tca aat tta   1488
Lys Thr Tyr Met Ser Asn Gly Ala Ile Tyr Ile Val Lys Ser Asn Leu
                485                 490                 495 ttt tta aat aac cca act ttt cta caa gaa aaa aca agt tgc tat ata   1536
```

```
Phe Leu Asn Asn Pro Thr Phe Leu Gln Glu Lys Thr Ser Cys Tyr Ile
            500                 505                 510 atg gac gaa aaa gct agt ttg gat ata gat aca aca gag gat tta aaa    1584
Met Asp Glu Lys Ala Ser Leu Asp Ile Asp Thr Thr Glu Asp Leu Lys
        515                 520                 525 aga gtt aat aat ata agc ttc tta                                    1608
Arg Val Asn Asn Ile Ser Phe Leu
        530                 535
```

<210> SEQ ID NO 25
<211> LENGTH: 536
<212> TYPE: PRT
<213> ORGANISM: Campylobacter jejuni
<220> FEATURE:
<223> OTHER INFORMATION: beta-1,4 N-acetylgalactosaminyl (GalNAc) transferase from C. jejuni NCTC 11168

<400> SEQUENCE: 25

```
Met Thr Leu Phe Tyr Lys Ile Ile Ala Phe Leu Arg Leu Leu Lys Ile
  1               5                  10                  15

Asp Lys Lys Leu Lys Phe Asp Asn Glu Tyr Phe Leu Asn Leu Asn Lys
             20                  25                  30

Lys Ile Tyr Asp Glu Lys His Lys Gly Phe Asp Phe Asp Pro Asn
         35                  40                  45

Ser Lys Asp Thr Lys Ser Pro Leu Asn Pro Trp Ala Phe Ile Arg Val
 50                  55                  60

Lys Asn Glu Ala Thr Thr Leu Arg Val Ser Leu Glu Ser Met Leu Pro
 65                  70                  75                  80

Ala Ile Gln Arg Gly Val Ile Gly Tyr Asn Asp Cys Thr Asp Gly Ser
             85                  90                  95

Glu Glu Ile Ile Leu Glu Phe Cys Lys Gln Tyr Pro Ser Phe Ile Pro
            100                 105                 110

Val Lys Tyr Pro His Glu Val Gln Ile Glu Asn Pro Gln Ser Glu Glu
            115                 120                 125

Asn Lys Leu His Ser Tyr Tyr Asn Tyr Val Ala Ser Phe Ile Pro Gln
        130                 135                 140

Asp Glu Trp Leu Ile Lys Ile Asp Val Asp His Tyr Tyr Asp Ala Lys
145                 150                 155                 160

Lys Leu Tyr Lys Ser Phe Tyr Met Ala Ser Lys Asn Thr Ala Val Arg
                165                 170                 175

Phe Pro Arg Ile Asn Phe Leu Ile Leu Asp Lys Ile Val Ile Gln Asn
            180                 185                 190

Ile Gly Glu Cys Gly Phe Ile Asp Gly Gly Asp Gln Leu Leu Ile Gln
        195                 200                 205

Lys Cys Asn Ser Val Phe Ile Glu Arg Met Val Ser Lys Gln Ser Gln
    210                 215                 220

Trp Ile Asp Pro Glu Lys Thr Val Lys Glu Leu Tyr Ser Glu Gln Gln
225                 230                 235                 240

Ile Ile Pro Lys His Ile Lys Ile Leu Gln Ala Glu Leu Leu Gln Trp
                245                 250                 255

His Phe Pro Ala Leu Lys Tyr His Arg Asn Asp Tyr Gln Lys His Leu
            260                 265                 270

Asp Ala Leu Thr Leu Glu Asp Phe Lys Lys Ile His Tyr Arg His Arg
        275                 280                 285

Lys Ile Lys Lys Ile Asn Tyr Thr Met Leu Asp Glu Lys Val Ile Arg
    290                 295                 300
```

```
Glu Ile Leu Asp Lys Phe Lys Leu Ser Gly Lys Lys Met Thr Leu Ala
305                 310                 315                 320

Ile Ile Pro Ala Arg Ala Gly Ser Lys Gly Ile Lys Asn Lys Asn Leu
            325                 330                 335

Ala Leu Leu His Asp Arg Pro Leu Leu Tyr Tyr Thr Ile Asn Ala Ala
        340                 345                 350

Lys Asn Ser Lys Tyr Val Asp Lys Ile Val Leu Ser Asp Gly Asp
    355                 360                 365

Asp Ile Leu Glu Tyr Gly Gln Thr Gln Gly Val Asp Val Leu Lys Arg
370                 375                 380

Pro Lys Glu Leu Ala Leu Asp Asp Thr Thr Ser Asp Lys Val Val Leu
385                 390                 395                 400

His Thr Leu Ser Phe Tyr Lys Asp Tyr Glu Asn Ile Val Leu Leu Gln
                405                 410                 415

Pro Thr Ser Pro Leu Arg Thr Asn Val His Ile Asp Glu Ala Phe Leu
            420                 425                 430

Lys Phe Lys Asn Glu Asn Ser Asn Ala Leu Ile Ser Val Val Glu Cys
        435                 440                 445

Asp Asn Lys Ile Leu Lys Ala Phe Ile Asp Asp Asn Gly Asn Leu Lys
450                 455                 460

Gly Ile Cys Asp Asn Lys Tyr Pro Phe Met Pro Arg Gln Lys Leu Pro
465                 470                 475                 480

Lys Thr Tyr Met Ser Asn Gly Ala Ile Tyr Ile Val Lys Ser Asn Leu
                485                 490                 495

Phe Leu Asn Asn Pro Thr Phe Leu Gln Glu Lys Thr Ser Cys Tyr Ile
            500                 505                 510

Met Asp Glu Lys Ala Ser Leu Asp Ile Asp Thr Thr Glu Asp Leu Lys
        515                 520                 525

Arg Val Asn Asn Ile Ser Phe Leu
    530                 535
```

<210> SEQ ID NO 26
<211> LENGTH: 906
<212> TYPE: DNA
<213> ORGANISM: Campylobacter jejuni
<220> FEATURE:
<221> NAME/KEY: CDS
<222> LOCATION: (1)..(906)
<223> OTHER INFORMATION: beta-1,3-galactosyltransferase from C. jejuni strain OH4384 (ORF 6a of lipooligosaccharide (LOS) biosynthesis locus)

<400> SEQUENCE: 26

```
atg ttt aaa att tca atc atc tta cca act tat aat gtg gaa caa tat      48
Met Phe Lys Ile Ser Ile Ile Leu Pro Thr Tyr Asn Val Glu Gln Tyr
 1               5                  10                  15 ata gca agg gca ata gaa agc tgt atc aat cag act ttt aaa gat ata      96
Ile Ala Arg Ala Ile Glu Ser Cys Ile Asn Gln Thr Phe Lys Asp Ile
            20                  25                  30 gaa ata att gta gtt gat gat tgt gga aat gat aat agt ata aat ata     144
Glu Ile Ile Val Val Asp Asp Cys Gly Asn Asp Asn Ser Ile Asn Ile
        35                  40                  45 gcc aaa gaa tac tct aaa aaa gac aaa aga ata aaa ata atc cac aat     192
Ala Lys Glu Tyr Ser Lys Lys Asp Lys Arg Ile Lys Ile Ile His Asn
    50                  55                  60 gaa aaa aac tta ggt ctt tta aga gca aga tat gaa ggt gtg aaa gta     240
Glu Lys Asn Leu Gly Leu Leu Arg Ala Arg Tyr Glu Gly Val Lys Val
65                  70                  75                  80
```

```
gca aac tct cct tat ata atg ttt tta gat cct gat gat tat ttg gaa      288
Ala Asn Ser Pro Tyr Ile Met Phe Leu Asp Pro Asp Asp Tyr Leu Glu
             85                  90                  95 cta aat gct tgt gaa gag tgt ata aaa att tta gat gaa cag gat gaa      336
Leu Asn Ala Cys Glu Glu Cys Ile Lys Ile Leu Asp Glu Gln Asp Glu
            100                 105                 110 gtt gat tta gtg ttt ttc aat gct att gtt gaa agt aat gtt att tca      384
Val Asp Leu Val Phe Phe Asn Ala Ile Val Glu Ser Asn Val Ile Ser
        115                 120                 125 tat aaa aag ttt gac ttt aat tct ggt ttt tat agc aaa aaa gag ttt      432
Tyr Lys Lys Phe Asp Phe Asn Ser Gly Phe Tyr Ser Lys Lys Glu Phe
    130                 135                 140 gta aaa aaa att att gca aag aaa aat tta tat tgg act atg tgg ggg      480
Val Lys Lys Ile Ile Ala Lys Lys Asn Leu Tyr Trp Thr Met Trp Gly
145                 150                 155                 160 aaa ctt ata aga aag aaa ttg tat tta gaa gct ttt gcg agt tta aga      528
Lys Leu Ile Arg Lys Lys Leu Tyr Leu Glu Ala Phe Ala Ser Leu Arg
                165                 170                 175 ctc gag aaa gat gtt aaa atc aat atg gct gaa gat gta ttg tta tat      576
Leu Glu Lys Asp Val Lys Ile Asn Met Ala Glu Asp Val Leu Leu Tyr
            180                 185                 190 tat cca atg tta agt caa gct caa aaa ata gca tat atg aac tgt aat      624
Tyr Pro Met Leu Ser Gln Ala Gln Lys Ile Ala Tyr Met Asn Cys Asn
        195                 200                 205 tta tat cat tac gtg cct aat aat aat tca att tgt aat act aag aat      672
Leu Tyr His Tyr Val Pro Asn Asn Asn Ser Ile Cys Asn Thr Lys Asn
    210                 215                 220 gaa gtg ctt gtt aaa aat aat att caa gag ttg cag ttg gtt tta aac      720
Glu Val Leu Val Lys Asn Asn Ile Gln Glu Leu Gln Leu Val Leu Asn
225                 230                 235                 240 tat tta agg caa aat tat att tta aac aag tat tgt agc gtt ctc tat      768
Tyr Leu Arg Gln Asn Tyr Ile Leu Asn Lys Tyr Cys Ser Val Leu Tyr
                245                 250                 255 gtg cta att aaa tat ttg cta tat att caa ata tat aaa ata aaa aga      816
Val Leu Ile Lys Tyr Leu Leu Tyr Ile Gln Ile Tyr Lys Ile Lys Arg
            260                 265                 270 aca aaa tta atg gtt aca tta tta gct aaa ata aat att tta act tta      864
Thr Lys Leu Met Val Thr Leu Leu Ala Lys Ile Asn Ile Leu Thr Leu
        275                 280                 285 aaa att tta ttt aaa tat aaa aaa ttt tta aaa caa tgt taa             906
Lys Ile Leu Phe Lys Tyr Lys Lys Phe Leu Lys Gln Cys
    290                 295                 300

<210> SEQ ID NO 27
<211> LENGTH: 301
<212> TYPE: PRT
<213> ORGANISM: Campylobacter jejuni
<220> FEATURE:
<223> OTHER INFORMATION: beta-1,3-galactosyltransferase from C. jejuni
      strain OH4384 (ORF 6a of lipooligosaccharide (LOS)
      biosynthesis locus)

<400> SEQUENCE: 27

Met Phe Lys Ile Ser Ile Ile Leu Pro Thr Tyr Asn Val Glu Gln Tyr
  1               5                  10                  15

Ile Ala Arg Ala Ile Glu Ser Cys Ile Asn Gln Thr Phe Lys Asp Ile
                 20                  25                  30

Glu Ile Ile Val Val Asp Asp Cys Gly Asn Asp Asn Ser Ile Asn Ile
             35                  40                  45

Ala Lys Glu Tyr Ser Lys Lys Asp Lys Arg Ile Lys Ile Ile His Asn
         50                  55                  60
```

```
Glu Lys Asn Leu Gly Leu Leu Arg Ala Arg Tyr Glu Gly Val Lys Val
 65                  70                  75                  80

Ala Asn Ser Pro Tyr Ile Met Phe Leu Asp Pro Asp Tyr Leu Glu
             85                  90                  95

Leu Asn Ala Cys Glu Cys Ile Lys Ile Leu Asp Glu Gln Asp Glu
            100                 105                 110

Val Asp Leu Val Phe Phe Asn Ala Ile Val Glu Ser Asn Val Ile Ser
            115                 120                 125

Tyr Lys Lys Phe Asp Phe Asn Ser Gly Phe Tyr Ser Lys Lys Glu Phe
        130                 135                 140

Val Lys Lys Ile Ile Ala Lys Lys Asn Leu Tyr Trp Thr Met Trp Gly
145                 150                 155                 160

Lys Leu Ile Arg Lys Lys Leu Tyr Leu Glu Ala Phe Ala Ser Leu Arg
                165                 170                 175

Leu Glu Lys Asp Val Lys Ile Asn Met Ala Glu Asp Val Leu Leu Tyr
            180                 185                 190

Tyr Pro Met Leu Ser Gln Ala Gln Lys Ile Ala Tyr Met Asn Cys Asn
        195                 200                 205

Leu Tyr His Tyr Val Pro Asn Asn Ser Ile Cys Asn Thr Lys Asn
210                 215                 220

Glu Val Leu Val Lys Asn Asn Ile Gln Glu Leu Gln Leu Val Leu Asn
225                 230                 235                 240

Tyr Leu Arg Gln Asn Tyr Ile Leu Asn Lys Tyr Cys Ser Val Leu Tyr
                245                 250                 255

Val Leu Ile Lys Tyr Leu Leu Tyr Ile Gln Ile Tyr Lys Ile Lys Arg
            260                 265                 270

Thr Lys Leu Met Val Thr Leu Leu Ala Lys Ile Asn Ile Leu Thr Leu
        275                 280                 285

Lys Ile Leu Phe Lys Tyr Lys Lys Phe Leu Lys Gln Cys
        290                 295                 300

<210> SEQ ID NO 28
<211> LENGTH: 912
<212> TYPE: DNA
<213> ORGANISM: Campylobacter jejuni
<220> FEATURE:
<221> NAME/KEY: CDS
<222> LOCATION: (1)..(912)
<223> OTHER INFORMATION: Campylobacter glycosyltransferase B (CgtB)
      beta-1,3 galactosyltransferase from C. jejuni serotype O:2
      (strain NCTC 11168)

<400> SEQUENCE: 28 atg agt caa att tcc atc ata cta cca act tat aat gtg gaa aaa tat    48
Met Ser Gln Ile Ser Ile Ile Leu Pro Thr Tyr Asn Val Glu Lys Tyr
  1               5                  10                  15 att gct aga gca tta gaa agt tgc att aac caa act ttt aaa gat ata    96
Ile Ala Arg Ala Leu Glu Ser Cys Ile Asn Gln Thr Phe Lys Asp Ile
             20                  25                  30 gaa atc att gta gta gat gat tgt ggt aat gat aaa agt ata gat ata   144
Glu Ile Ile Val Val Asp Asp Cys Gly Asn Asp Lys Ser Ile Asp Ile
         35                  40                  45 gct aaa gag tat gct agt aaa gat gat aga ata aaa atc ata cat aat   192
Ala Lys Glu Tyr Ala Ser Lys Asp Asp Arg Ile Lys Ile Ile His Asn
     50                  55                  60 gaa gag aat tta aag ctt tta aga gca aga tat gaa ggt gct aaa gta   240
Glu Glu Asn Leu Lys Leu Leu Arg Ala Arg Tyr Glu Gly Ala Lys Val
 65                  70                  75                  80
```

-continued

| | | |
|---|---|---|
| gca act tca cct tat atc atg ttt tta gat tct gat gat tat tta gaa<br>Ala Thr Ser Pro Tyr Ile Met Phe Leu Asp Ser Asp Asp Tyr Leu Glu<br>85 90 95 | | 288 |
| ctt aat gct tgc gaa gaa tgt att aaa att ttg gat atg ggt ggg ggg<br>Leu Asn Ala Cys Glu Glu Cys Ile Lys Ile Leu Asp Met Gly Gly Gly<br>100 105 110 | | 336 |
| ggt aaa att gat ttg ttg tgt ttt gaa gct ttt att acc aat gca aaa<br>Gly Lys Ile Asp Leu Leu Cys Phe Glu Ala Phe Ile Thr Asn Ala Lys<br>115 120 125 | | 384 |
| aaa tca ata aaa aaa tta aat ata aaa caa gga aaa tac aac aac aaa<br>Lys Ser Ile Lys Lys Leu Asn Ile Lys Gln Gly Lys Tyr Asn Asn Lys<br>130 135 140 | | 432 |
| gaa ttt aca atg caa ata ctt aaa act aaa aat cca ttt tgg aca atg<br>Glu Phe Thr Met Gln Ile Leu Lys Thr Lys Asn Pro Phe Trp Thr Met<br>145 150 155 160 | | 480 |
| tgg gct aaa ata atc aaa aaa gat att tat tta aaa gcc ttc aac atg<br>Trp Ala Lys Ile Ile Lys Lys Asp Ile Tyr Leu Lys Ala Phe Asn Met<br>165 170 175 | | 528 |
| tta aat ctc aaa aaa gaa atc aaa ata aat atg gca gaa gat gcc tta<br>Leu Asn Leu Lys Lys Glu Ile Lys Ile Asn Met Ala Glu Asp Ala Leu<br>180 185 190 | | 576 |
| tta tat tat cct ttg aca ata tta tct aat gaa ata ttt tac tta aca<br>Leu Tyr Tyr Pro Leu Thr Ile Leu Ser Asn Glu Ile Phe Tyr Leu Thr<br>195 200 205 | | 624 |
| caa cct ttg tat acc cag cat gta aat agc aat tct ata aca aat aat<br>Gln Pro Leu Tyr Thr Gln His Val Asn Ser Asn Ser Ile Thr Asn Asn<br>210 215 220 | | 672 |
| att aat tct tta gaa gct aat att caa gaa cat aaa att gtt tta aat<br>Ile Asn Ser Leu Glu Ala Asn Ile Gln Glu His Lys Ile Val Leu Asn<br>225 230 235 240 | | 720 |
| gtt tta aaa tca att aaa aat aaa aaa aca cct cta tat ttt cta att<br>Val Leu Lys Ser Ile Lys Asn Lys Lys Thr Pro Leu Tyr Phe Leu Ile<br>245 250 255 | | 768 |
| ata tat tta tta aaa att caa tta ttg aaa tat gaa caa aat ttt aat<br>Ile Tyr Leu Leu Lys Ile Gln Leu Leu Lys Tyr Glu Gln Asn Phe Asn<br>260 265 270 | | 816 |
| aaa aga aat ata aat ctt att tat tat aaa ata aat att tta tat caa<br>Lys Arg Asn Ile Asn Leu Ile Tyr Tyr Lys Ile Asn Ile Leu Tyr Gln<br>275 280 285 | | 864 |
| aaa tat caa ttc aaa tgg aaa aaa ttt tta tat aat tta att ccg taa<br>Lys Tyr Gln Phe Lys Trp Lys Lys Phe Leu Tyr Asn Leu Ile Pro<br>290 295 300 | | 912 |

<210> SEQ ID NO 29
<211> LENGTH: 303
<212> TYPE: PRT
<213> ORGANISM: Campylobacter jejuni
<220> FEATURE:
<223> OTHER INFORMATION: Campylobacter glycosyltransferase B (CgtB)
    beta-1,3 galactosyltransferase from C. jejuni serotype O:2
    (strain NCTC 11168)

<400> SEQUENCE: 29

Met Ser Gln Ile Ser Ile Ile Leu Pro Thr Tyr Asn Val Glu Lys Tyr
1               5                   10                  15

Ile Ala Arg Ala Leu Glu Ser Cys Ile Asn Gln Thr Phe Lys Asp Ile
            20                  25                  30

Glu Ile Ile Val Val Asp Asp Cys Gly Asn Asp Lys Ser Ile Asp Ile
        35                  40                  45

Ala Lys Glu Tyr Ala Ser Lys Asp Asp Arg Ile Lys Ile Ile His Asn

-continued

```
            50                  55                  60
Glu Glu Asn Leu Lys Leu Leu Arg Ala Arg Tyr Glu Gly Ala Lys Val
 65                  70                  75                  80

Ala Thr Ser Pro Tyr Ile Met Phe Leu Asp Ser Asp Tyr Leu Glu
                85                  90                  95

Leu Asn Ala Cys Glu Glu Cys Ile Lys Ile Leu Asp Met Gly Gly Gly
                100                 105                 110

Gly Lys Ile Asp Leu Leu Cys Phe Glu Ala Phe Ile Thr Asn Ala Lys
                115                 120                 125

Lys Ser Ile Lys Lys Leu Asn Ile Lys Gln Gly Lys Tyr Asn Asn Lys
130                 135                 140

Glu Phe Thr Met Gln Ile Leu Lys Thr Lys Asn Pro Phe Trp Thr Met
145                 150                 155                 160

Trp Ala Lys Ile Ile Lys Lys Asp Ile Tyr Leu Lys Ala Phe Asn Met
                165                 170                 175

Leu Asn Leu Lys Lys Glu Ile Lys Ile Asn Met Ala Glu Asp Ala Leu
                180                 185                 190

Leu Tyr Tyr Pro Leu Thr Ile Leu Ser Asn Glu Ile Phe Tyr Leu Thr
                195                 200                 205

Gln Pro Leu Tyr Thr Gln His Val Asn Ser Asn Ser Ile Thr Asn Asn
                210                 215                 220

Ile Asn Ser Leu Glu Ala Asn Ile Gln Glu His Lys Ile Val Leu Asn
225                 230                 235                 240

Val Leu Lys Ser Ile Lys Asn Lys Lys Thr Pro Leu Tyr Phe Leu Ile
                245                 250                 255

Ile Tyr Leu Leu Lys Ile Gln Leu Leu Lys Tyr Glu Gln Asn Phe Asn
                260                 265                 270

Lys Arg Asn Ile Asn Leu Ile Tyr Tyr Lys Ile Asn Ile Leu Tyr Gln
                275                 280                 285

Lys Tyr Gln Phe Lys Trp Lys Lys Phe Leu Tyr Asn Leu Ile Pro
                290                 295                 300

<210> SEQ ID NO 30
<211> LENGTH: 891
<212> TYPE: DNA
<213> ORGANISM: Campylobacter jejuni
<220> FEATURE:
<221> NAME/KEY: CDS
<222> LOCATION: (1)..(891)
<223> OTHER INFORMATION: beta-1,3 galactosyl transferase from C. jejuni
      O:10

<400> SEQUENCE: 30 atg ttt aaa att tca atc atc ttg cca act tat aat gtg gaa caa tat    48
Met Phe Lys Ile Ser Ile Ile Leu Pro Thr Tyr Asn Val Glu Gln Tyr
 1               5                  10                  15 ata gca agg gca ata gaa agt tgt atc aat cag act ttt aaa aat ata    96
Ile Ala Arg Ala Ile Glu Ser Cys Ile Asn Gln Thr Phe Lys Asn Ile
            20                  25                  30 gaa ata att gta gtt gat gat tgt gga agt gac aaa agt ata gat ata    144
Glu Ile Ile Val Val Asp Asp Cys Gly Ser Asp Lys Ser Ile Asp Ile
        35                  40                  45 gtt aaa gaa tat gcc aaa aaa gat gat aga ata aaa atc ata cat aat    192
Val Lys Glu Tyr Ala Lys Lys Asp Asp Arg Ile Lys Ile Ile His Asn
    50                  55                  60 gaa gaa aat tta aaa ctt tta aga gct aga tat gaa ggt gta aaa gta    240
Glu Glu Asn Leu Lys Leu Leu Arg Ala Arg Tyr Glu Gly Val Lys Val
 65                  70                  75                  80
```

```
gca aac tct cct tat ata atg ttt tta gat cct gat gat tat tta gaa    288
Ala Asn Ser Pro Tyr Ile Met Phe Leu Asp Pro Asp Asp Tyr Leu Glu
                85                  90                  95 ctt aat gct tgt gaa gaa tgt atg aaa att tta aaa aac aat gaa ata    336
Leu Asn Ala Cys Glu Glu Cys Met Lys Ile Leu Lys Asn Asn Glu Ile
            100                 105                 110 gat tta tta ttt ttt aat gca ttt gta ttg gaa aat aac aat aaa ata    384
Asp Leu Leu Phe Phe Asn Ala Phe Val Leu Glu Asn Asn Asn Lys Ile
        115                 120                 125 gaa aga aag ttg aat ttt caa gaa aaa tgt tat gta aaa aaa gat ttt    432
Glu Arg Lys Leu Asn Phe Gln Glu Lys Cys Tyr Val Lys Lys Asp Phe
    130                 135                 140 tta aaa gaa cta tta aaa act aaa aat tta ttt tgg aca gtg tgg gca    480
Leu Lys Glu Leu Leu Lys Thr Lys Asn Leu Phe Trp Thr Val Trp Ala
145                 150                 155                 160 aaa gtc ata aaa aaa gaa tta tat ctc aag gct gtt ggt tta ata tcg    528
Lys Val Ile Lys Lys Glu Leu Tyr Leu Lys Ala Val Gly Leu Ile Ser
                165                 170                 175 cta gaa aat gct aaa ata aat atg gct gaa gat gtt tta tta tat tac    576
Leu Glu Asn Ala Lys Ile Asn Met Ala Glu Asp Val Leu Leu Tyr Tyr
            180                 185                 190 cct ttg ata aat att tca aat act ata ttt cac ttg agt aaa aat tta    624
Pro Leu Ile Asn Ile Ser Asn Thr Ile Phe His Leu Ser Lys Asn Leu
        195                 200                 205 tac aat tat caa ata aat aat ttc tct ata acc aaa aca tta aca ttg    672
Tyr Asn Tyr Gln Ile Asn Asn Phe Ser Ile Thr Lys Thr Leu Thr Leu
    210                 215                 220 caa aat ata aaa aca aat ata caa gaa caa gat aat gtt cta tat ctt    720
Gln Asn Ile Lys Thr Asn Ile Gln Glu Gln Asp Asn Val Leu Tyr Leu
225                 230                 235                 240 cta aag aag atg caa tat aat tac aat ttt aac tta act ttg ctt aaa    768
Leu Lys Lys Met Gln Tyr Asn Tyr Asn Phe Asn Leu Thr Leu Leu Lys
                245                 250                 255 tta att gag tat ttt tta tta att gaa aaa tac tca tta tca agc aag    816
Leu Ile Glu Tyr Phe Leu Leu Ile Glu Lys Tyr Ser Leu Ser Ser Lys
            260                 265                 270 cga aat gtt ctt tgt ttt aaa atc aat att ttt ttt aaa aaa atc caa    864
Arg Asn Val Leu Cys Phe Lys Ile Asn Ile Phe Phe Lys Lys Ile Gln
        275                 280                 285 ttt aaa ttt tat cgc ttg ctg aag atg                                891
Phe Lys Phe Tyr Arg Leu Leu Lys Met
    290                 295
```

<210> SEQ ID NO 31
<211> LENGTH: 297
<212> TYPE: PRT
<213> ORGANISM: Campylobacter jejuni
<220> FEATURE:
<223> OTHER INFORMATION: beta-1,3 galactosyl transferase from C. jejuni
      O:10

<400> SEQUENCE: 31

```
Met Phe Lys Ile Ser Ile Ile Leu Pro Thr Tyr Asn Val Glu Gln Tyr
1               5                   10                  15

Ile Ala Arg Ala Ile Glu Ser Cys Ile Asn Gln Thr Phe Lys Asn Ile
            20                  25                  30

Glu Ile Ile Val Val Asp Asp Cys Gly Ser Asp Lys Ser Ile Asp Ile
        35                  40                  45

Val Lys Glu Tyr Ala Lys Lys Asp Asp Arg Ile Lys Ile Ile His Asn
    50                  55                  60
```

```
Glu Glu Asn Leu Lys Leu Leu Arg Ala Arg Tyr Glu Gly Val Lys Val
 65                  70                  75                  80

Ala Asn Ser Pro Tyr Ile Met Phe Leu Asp Pro Asp Tyr Leu Glu
                 85                  90                  95

Leu Asn Ala Cys Glu Cys Met Lys Ile Leu Lys Asn Asn Glu Ile
            100                 105                 110

Asp Leu Leu Phe Phe Asn Ala Phe Val Leu Glu Asn Asn Lys Ile
        115                 120                 125

Glu Arg Lys Leu Asn Phe Gln Glu Lys Cys Tyr Val Lys Lys Asp Phe
    130                 135                 140

Leu Lys Glu Leu Leu Lys Thr Lys Asn Leu Phe Trp Thr Val Trp Ala
145                 150                 155                 160

Lys Val Ile Lys Lys Glu Leu Tyr Leu Lys Ala Val Gly Leu Ile Ser
                165                 170                 175

Leu Glu Asn Ala Lys Ile Asn Met Ala Glu Asp Val Leu Leu Tyr Tyr
            180                 185                 190

Pro Leu Ile Asn Ile Ser Asn Thr Ile Phe His Leu Ser Lys Asn Leu
        195                 200                 205

Tyr Asn Tyr Gln Ile Asn Asn Phe Ser Ile Thr Lys Thr Leu Thr Leu
    210                 215                 220

Gln Asn Ile Lys Thr Asn Ile Gln Glu Gln Asp Asn Val Leu Tyr Leu
225                 230                 235                 240

Leu Lys Lys Met Gln Tyr Asn Tyr Asn Phe Asn Leu Thr Leu Leu Lys
                245                 250                 255

Leu Ile Glu Tyr Phe Leu Leu Ile Glu Lys Tyr Ser Leu Ser Ser Lys
            260                 265                 270

Arg Asn Val Leu Cys Phe Lys Ile Asn Ile Phe Phe Lys Lys Ile Gln
        275                 280                 285

Phe Lys Phe Tyr Arg Leu Leu Lys Met
    290                 295

<210> SEQ ID NO 32
<211> LENGTH: 295
<212> TYPE: PRT
<213> ORGANISM: Campylobacter jejuni
<220> FEATURE:
<223> OTHER INFORMATION: lipid A biosynthesis acyltransferase from C.
      jejuni OH4384

<400> SEQUENCE: 32

Met Lys Asn Ser Asp Arg Ile Tyr Leu Ser Leu Tyr Tyr Ile Leu Lys
  1               5                  10                  15

Phe Phe Val Thr Phe Met Pro Asp Cys Ile Leu His Phe Leu Ala Leu
                 20                  25                  30

Ile Val Ala Arg Ile Ala Phe His Leu Asn Lys Lys His Arg Lys Ile
             35                  40                  45

Ile Asn Thr Asn Leu Gln Ile Cys Phe Pro Gln Tyr Thr Gln Lys Glu
         50                  55                  60

Arg Asp Lys Leu Ser Leu Lys Ile Tyr Glu Asn Phe Ala Gln Phe Gly
 65                  70                  75                  80

Ile Asp Cys Leu Gln Asn Gln Asn Thr Thr Lys Glu Lys Ile Leu Asn
                 85                  90                  95

Lys Val Asn Phe Ile Asn Glu Asn Phe Leu Ile Asp Ala Leu Ala Leu
            100                 105                 110

Lys Arg Pro Ile Ile Phe Thr Thr Ala His Tyr Gly Asn Trp Glu Ile
```

```
                115                 120                 125
Leu Ser Leu Ala Tyr Ala Ala Lys Tyr Gly Ala Ile Ser Ile Val Gly
        130                 135                 140

Lys Lys Leu Lys Ser Glu Val Met Tyr Glu Ile Leu Ser Gln Ser Arg
145                 150                 155                 160

Thr Gln Phe Asp Ile Glu Leu Ile Asp Lys Lys Gly Gly Ile Arg Gln
                165                 170                 175

Met Leu Ser Ala Leu Lys Lys Glu Arg Ala Leu Gly Ile Leu Thr Asp
                180                 185                 190

Gln Asp Cys Val Glu Asn Glu Ser Val Arg Leu Lys Phe Phe Asn Lys
                195                 200                 205

Glu Val Asn Tyr Gln Met Gly Ala Ser Leu Ile Ala Gln Arg Ser Asn
        210                 215                 220

Ala Leu Ile Ile Pro Val Tyr Ala Tyr Lys Glu Gly Gly Lys Phe Cys
225                 230                 235                 240

Ile Glu Phe Phe Lys Ala Lys Asp Ser Gln Asn Ala Ser Leu Glu Glu
                245                 250                 255

Leu Thr Leu Tyr Gln Ala Gln Ser Cys Glu Glu Met Ile Lys Lys Arg
        260                 265                 270

Pro Trp Glu Tyr Phe Phe His Arg Arg Phe Ala Ser Tyr Asn Glu
            275                 280                 285

Glu Ile Tyr Lys Gly Ala Lys
        290                 295

<210> SEQ ID NO 33
<211> LENGTH: 418
<212> TYPE: PRT
<213> ORGANISM: Campylobacter jejuni
<220> FEATURE:
<223> OTHER INFORMATION: glycosyltransferase from C. jejuni OH4384
      (ORF 3a of lipooligosaccharide (LOS) biosynthesis locus)

<400> SEQUENCE: 33

Met Asn Leu Lys Gln Ile Ser Val Ile Ile Val Lys Asn Ala Glu
1               5                   10                  15

Gln Thr Leu Leu Glu Cys Leu Asn Ser Leu Lys Asp Phe Asp Glu Ile
                20                  25                  30

Ile Leu Leu Asn Asn Glu Ser Ser Asp Asn Thr Leu Lys Ile Ala Asn
            35                  40                  45

Glu Phe Lys Lys Asp Phe Ala Asn Leu Tyr Ile Tyr His Asn Ala Phe
    50                  55                  60

Ile Gly Phe Gly Ala Leu Lys Asn Leu Ala Leu Ser Tyr Ala Lys Asn
65                  70                  75                  80

Asp Trp Ile Leu Ser Ile Asp Ala Asp Glu Val Leu Glu Asn Glu Cys
                85                  90                  95

Ile Lys Glu Leu Lys Asn Leu Lys Leu Gln Glu Asp Asn Ile Ile Ala
            100                 105                 110

Leu Ser Arg Lys Asn Leu Tyr Lys Gly Glu Trp Ile Lys Ala Cys Gly
        115                 120                 125

Trp Trp Pro Asp Tyr Val Leu Arg Ile Phe Asn Lys Asn Phe Thr Arg
    130                 135                 140

Phe Asn Asp Asn Leu Val His Glu Ser Leu Val Leu Pro Ser Asn Ala
145                 150                 155                 160

Lys Lys Ile Tyr Leu Lys Asn Gly Leu Lys His Tyr Ser Tyr Lys Asp
                165                 170                 175
```

```
Ile Ser His Leu Ile Asp Lys Met Gln Tyr Tyr Ser Ser Leu Trp Ala
            180                 185                 190

Lys Gln Asn Ile His Lys Lys Ser Gly Val Leu Lys Ala Asn Leu Arg
        195                 200                 205

Ala Phe Trp Thr Phe Phe Arg Asn Tyr Phe Leu Lys Asn Gly Phe Leu
    210                 215                 220

Tyr Gly Tyr Lys Gly Phe Ile Ile Ser Val Cys Ser Ala Leu Gly Thr
225                 230                 235                 240

Phe Phe Lys Tyr Met Lys Leu Tyr Glu Leu Gln Arg Gln Lys Pro Lys
                245                 250                 255

Thr Cys Ala Leu Ile Ile Ile Thr Tyr Asn Gln Lys Glu Arg Leu Lys
            260                 265                 270

Leu Val Leu Asp Ser Val Lys Asn Leu Ala Phe Leu Pro Asn Glu Val
            275                 280                 285

Leu Ile Ala Asp Asp Gly Ser Lys Glu Asp Thr Ala Arg Leu Ile Glu
        290                 295                 300

Glu Tyr Gln Lys Asp Phe Pro Cys Pro Leu Lys His Ile Trp Gln Glu
305                 310                 315                 320

Asp Glu Gly Phe Lys Leu Ser Lys Ser Arg Asn Lys Thr Ile Lys Asn
                325                 330                 335

Ala Asp Ser Glu Tyr Ile Ile Val Ile Asp Gly Asp Met Ile Leu Glu
            340                 345                 350

Lys Asp Phe Ile Lys Glu His Leu Glu Phe Ala Gln Arg Lys Leu Phe
        355                 360                 365

Leu Gln Gly Ser Arg Val Ile Leu Asn Lys Lys Glu Ser Glu Ile
    370                 375                 380

Leu Asn Lys Asp Asp Tyr Arg Ile Ile Phe Asn Lys Lys Asp Phe Lys
385                 390                 395                 400

Ser Ser Lys Asn Ser Phe Leu Ala Lys Ile Phe Tyr Ser Leu Ser Lys
                405                 410                 415

Lys Arg

<210> SEQ ID NO 34
<211> LENGTH: 389
<212> TYPE: PRT
<213> ORGANISM: Campylobacter jejuni
<220> FEATURE:
<223> OTHER INFORMATION: glycosyltransferase of C. jejuni OH4384 (ORF
      4a of lipooligosaccharide (LOS) biosynthesis locus)

<400> SEQUENCE: 34

Met Lys Lys Ile Gly Val Val Ile Pro Ile Tyr Asn Val Glu Lys Tyr
1               5                   10                  15

Leu Arg Glu Cys Leu Asp Ser Val Ile Asn Gln Thr Tyr Thr Asn Leu
            20                  25                  30

Glu Ile Ile Leu Val Asn Asp Gly Ser Thr Asp Glu His Ser Leu Asn
        35                  40                  45

Ile Ala Lys Glu Tyr Thr Leu Lys Asp Lys Arg Ile Thr Leu Phe Asp
    50                  55                  60

Lys Lys Asn Gly Gly Leu Ser Ser Ala Arg Asn Ile Gly Ile Glu Tyr
65                  70                  75                  80

Phe Ser Gly Glu Tyr Lys Leu Lys Asn Lys Thr Gln His Ile Lys Glu
                85                  90                  95

Asn Ser Leu Ile Glu Phe Gln Leu Asp Gly Asn Asn Pro Tyr Asn Ile
            100                 105                 110
```

-continued

```
Tyr Lys Ala Tyr Lys Ser Ser Gln Ala Phe Asn Asn Glu Lys Asp Leu
            115                 120                 125

Thr Asn Phe Thr Tyr Pro Ser Ile Asp Tyr Ile Ile Phe Leu Asp Ser
    130                 135                 140

Asp Asn Tyr Trp Lys Leu Asn Cys Ile Glu Cys Val Ile Arg Met
145                 150                 155                 160

Lys Asn Val Asp Val Leu Trp Phe Asp His Asp Cys Thr Tyr Glu Asp
            165                 170                 175

Asn Ile Lys Asn Lys His Lys Lys Thr Arg Met Glu Ile Phe Asp Phe
            180                 185                 190

Lys Lys Glu Cys Ile Ile Thr Pro Lys Glu Tyr Ala Asn Arg Ala Leu
            195                 200                 205

Ser Val Gly Ser Arg Asp Ile Ser Phe Gly Trp Asn Gly Met Ile Asp
    210                 215                 220

Phe Asn Phe Leu Lys Gln Ile Lys Leu Lys Phe Ile Asn Phe Ile Ile
225                 230                 235                 240

Asn Glu Asp Ile His Phe Gly Ile Ile Leu Phe Ala Ser Ala Asn Lys
                245                 250                 255

Ile Tyr Val Leu Ser Gln Lys Leu Tyr Leu Cys Arg Leu Arg Ala Asn
            260                 265                 270

Ser Ile Ser Asn His Asp Lys Lys Ile Thr Lys Ala Asn Val Ser Glu
    275                 280                 285

Tyr Phe Lys Asp Ile Tyr Glu Thr Phe Gly Glu Asn Ala Lys Glu Ala
            290                 295                 300

Lys Asn Tyr Leu Lys Ala Ala Ser Arg Val Ile Thr Ala Leu Lys Leu
305                 310                 315                 320

Ile Glu Phe Phe Lys Asp Gln Lys Asn Glu Asn Ala Leu Ala Ile Lys
                325                 330                 335

Glu Thr Phe Leu Pro Cys Tyr Ala Lys Lys Ala Leu Met Ile Lys Lys
            340                 345                 350

Phe Lys Lys Asp Pro Leu Asn Leu Lys Glu Gln Leu Val Leu Ile Lys
            355                 360                 365

Pro Phe Ile Gln Thr Lys Leu Pro Tyr Asp Ile Trp Lys Phe Trp Gln
    370                 375                 380

Lys Ile Lys Asn Ile
385

<210> SEQ ID NO 35
<211> LENGTH: 346
<212> TYPE: PRT
<213> ORGANISM: Campylobacter jejuni
<220> FEATURE:
<223> OTHER INFORMATION: sialic acid synthase from C. jejuni OH4384
      (ORF 8a of lipooligosaccharide (LOS) biosynthesis locus)

<400> SEQUENCE: 35

Met Lys Glu Ile Lys Ile Gln Asn Ile Ile Ser Glu Glu Lys Ala
 1               5                  10                  15

Pro Leu Val Val Pro Glu Ile Gly Ile Asn His Asn Gly Ser Leu Glu
            20                  25                  30

Leu Ala Lys Ile Met Val Asp Ala Ala Phe Ser Thr Gly Ala Lys Ile
        35                  40                  45

Ile Lys His Gln Thr His Ile Val Glu Asp Glu Met Ser Lys Ala Ala
    50                  55                  60

Lys Lys Val Ile Pro Gly Asn Ala Lys Ile Ser Ile Tyr Glu Ile Met
65                  70                  75                  80
```

```
Gln Lys Cys Ala Leu Asp Tyr Lys Asp Glu Leu Ala Leu Lys Glu Tyr
                85                  90                  95

Thr Glu Lys Leu Gly Leu Val Tyr Leu Ser Thr Pro Phe Ser Arg Ala
            100                 105                 110

Gly Ala Asn Arg Leu Glu Asp Met Gly Val Ser Ala Phe Lys Ile Gly
        115                 120                 125

Ser Gly Glu Cys Asn Asn Tyr Pro Leu Ile Lys His Ile Ala Ala Phe
    130                 135                 140

Lys Lys Pro Met Ile Val Ser Thr Gly Met Asn Ser Ile Glu Ser Ile
145                 150                 155                 160

Lys Pro Thr Val Lys Ile Leu Leu Asp Asn Glu Ile Pro Phe Val Leu
                165                 170                 175

Met His Thr Thr Asn Leu Tyr Pro Thr Pro His Asn Leu Val Arg Leu
            180                 185                 190

Asn Ala Met Leu Glu Leu Lys Lys Glu Phe Ser Cys Met Val Gly Leu
        195                 200                 205

Ser Asp His Thr Thr Asp Asn Leu Ala Cys Leu Gly Ala Val Ala Leu
    210                 215                 220

Gly Ala Cys Val Leu Glu Arg His Phe Thr Asp Ser Met His Arg Ser
225                 230                 235                 240

Gly Pro Asp Ile Val Cys Ser Met Asp Thr Gln Ala Leu Lys Glu Leu
                245                 250                 255

Ile Ile Gln Ser Glu Gln Met Ala Ile Met Arg Gly Asn Asn Glu Ser
            260                 265                 270

Lys Lys Ala Ala Lys Gln Glu Gln Val Thr Ile Asp Phe Ala Phe Ala
        275                 280                 285

Ser Val Val Ser Ile Lys Asp Ile Lys Lys Gly Glu Val Leu Ser Met
    290                 295                 300

Asp Asn Ile Trp Val Lys Arg Pro Gly Leu Gly Ile Ser Ala Ala
305                 310                 315                 320

Glu Phe Glu Asn Ile Leu Gly Lys Lys Ala Leu Arg Asp Ile Glu Asn
                325                 330                 335

Asp Thr Gln Leu Ser Tyr Glu Asp Phe Ala
            340                 345
```

<210> SEQ ID NO 36
<211> LENGTH: 352
<212> TYPE: PRT
<213> ORGANISM: Campylobacter jejuni
<220> FEATURE:
<223> OTHER INFORMATION: enzyme involved in sialic acid biosynthesis
      from C. jejuni OH4384 (ORF 9a of lipooligosaccharide (LOS)
      biosynthesis locus)

<400> SEQUENCE: 36

```
Met Tyr Arg Val Gln Asn Ser Ser Glu Phe Glu Leu Tyr Ile Phe Ala
  1               5                  10                  15

Thr Gly Met His Leu Ser Lys Asn Phe Gly Tyr Thr Val Lys Glu Leu
             20                  25                  30

Tyr Lys Asn Gly Phe Lys Asn Ile Tyr Glu Phe Ile Asn Tyr Asp Lys
         35                  40                  45

Tyr Phe Ser Thr Asp Lys Ala Leu Ala Thr Thr Ile Asp Gly Phe Ser
     50                  55                  60

Arg Tyr Val Asn Glu Leu Lys Pro Asp Leu Ile Val Val His Gly Asp
 65                  70                  75                  80
```

-continued

```
Arg Ile Glu Pro Leu Ala Ala Ile Val Gly Ala Leu Asn Asn Ile
                 85                  90                  95

Leu Val Ala His Ile Glu Gly Gly Glu Ile Ser Gly Thr Ile Asp Asp
            100                 105                 110

Ser Leu Arg His Ala Ile Ser Lys Leu Ala His Ile His Leu Val Asn
            115                 120                 125

Asp Glu Phe Ala Lys Arg Arg Leu Met Gln Leu Gly Glu Asp Glu Lys
        130                 135                 140

Ser Ile Phe Ile Ile Gly Ser Pro Asp Leu Glu Leu Leu Asn Asp Asn
145                 150                 155                 160

Lys Ile Ser Leu Asn Glu Ala Lys Lys Tyr Tyr Asp Ile Asn Tyr Glu
                165                 170                 175

Asn Tyr Ala Leu Leu Met Phe His Pro Val Thr Thr Glu Ile Thr Ser
            180                 185                 190

Ile Lys Asn Gln Ala Asp Asn Leu Val Lys Ala Leu Ile Gln Ser Asn
        195                 200                 205

Lys Asn Tyr Ile Val Ile Tyr Pro Asn Asn Asp Leu Gly Phe Glu Leu
210                 215                 220

Ile Leu Gln Ser Tyr Glu Glu Leu Lys Asn Asn Pro Arg Phe Lys Leu
225                 230                 235                 240

Phe Pro Ser Leu Arg Phe Glu Tyr Phe Ile Thr Leu Leu Lys Asn Ala
                245                 250                 255

Asp Phe Ile Ile Gly Asn Ser Ser Cys Ile Leu Lys Glu Ala Leu Tyr
            260                 265                 270

Leu Lys Thr Ala Gly Ile Leu Val Gly Ser Arg Gln Asn Gly Arg Leu
        275                 280                 285

Gly Asn Glu Asn Thr Leu Lys Val Asn Ala Asn Ser Asp Glu Ile Leu
290                 295                 300

Lys Ala Ile Asn Thr Ile His Lys Lys Gln Asp Leu Phe Ser Ala Lys
305                 310                 315                 320

Leu Glu Ile Leu Asp Ser Ser Lys Leu Phe Phe Glu Tyr Leu Gln Ser
                325                 330                 335

Gly Glu Phe Phe Lys Leu Asn Thr Gln Lys Val Phe Lys Asp Ile Lys
            340                 345                 350

<210> SEQ ID NO 37
<211> LENGTH: 221
<212> TYPE: PRT
<213> ORGANISM: Campylobacter jejuni
<220> FEATURE:
<223> OTHER INFORMATION: CMP-sialic acid synthetase from C. jejuni
      OH4384 (ORF 10a of lipooligosaccharide (LOS) biosynthesis
      locus)

<400> SEQUENCE: 37

Met Ser Leu Ala Ile Ile Pro Ala Arg Gly Gly Ser Lys Gly Ile Lys
1               5                   10                  15

Asn Lys Asn Leu Val Leu Leu Asn Asn Lys Pro Leu Ile Tyr Tyr Thr
            20                  25                  30

Ile Lys Ala Ala Leu Asn Thr Lys Ser Ile Ser Lys Val Val Val Ser
        35                  40                  45

Ser Asp Ser Asp Glu Ile Leu Asn Tyr Ala Lys Ser Gln Asn Val Asp
    50                  55                  60

Ile Leu Lys Arg Pro Ile Ser Leu Ala Gln Asp Asn Thr Thr Ser Asp
65                  70                  75                  80

Lys Val Leu Leu His Ala Leu Lys Phe Tyr Lys Asp Tyr Glu Asp Val
```

```
                        85                  90                  95
Val Phe Leu Gln Pro Thr Ser Pro Leu Arg Thr Asn Ile His Ile Asp
            100                 105                 110

Glu Ala Phe Asn Leu Tyr Lys Asn Ser Asn Ala Asn Ala Leu Ile Ser
            115                 120                 125

Val Ser Glu Cys Asp Asn Lys Ile Leu Lys Ala Phe Val Cys Asn Glu
        130                 135                 140

Tyr Gly Asp Leu Ala Gly Ile Cys Asn Asp Glu Tyr Pro Phe Met Pro
145                 150                 155                 160

Arg Gln Lys Leu Pro Lys Thr Tyr Met Ser Asn Gly Ala Ile Tyr Ile
                165                 170                 175

Leu Lys Ile Lys Glu Phe Leu Asn Asn Pro Ser Phe Leu Gln Ser Lys
            180                 185                 190

Thr Lys His Phe Leu Met Asp Glu Ser Ser Ser Leu Asp Ile Asp Cys
            195                 200                 205

Leu Glu Asp Leu Lys Lys Ala Glu Gln Ile Trp Lys Lys
        210                 215                 220

<210> SEQ ID NO 38
<211> LENGTH: 277
<212> TYPE: PRT
<213> ORGANISM: Campylobacter jejuni
<220> FEATURE:
<223> OTHER INFORMATION: acetyltransferase from C. jejuni OH4384 (ORF
      11a of lipooligosaccharide (LOS) biosynthesis locus)

<400> SEQUENCE: 38

Met Glu Lys Ile Thr Leu Lys Cys Asn Lys Asn Ile Leu Asn Leu Leu
1               5                   10                  15

Lys Gln Tyr Asn Ile Tyr Thr Lys Thr Tyr Ile Glu Asn Pro Arg Arg
            20                  25                  30

Phe Ser Arg Leu Lys Thr Lys Asp Phe Ile Thr Phe Pro Leu Glu Asn
        35                  40                  45

Asn Gln Leu Glu Ser Val Ala Gly Leu Gly Ile Glu Glu Tyr Cys Ala
    50                  55                  60

Phe Lys Phe Ser Asn Ile Leu His Glu Met Asp Ser Phe Ser Phe Ser
65                  70                  75                  80

Gly Ser Phe Leu Pro His Tyr Thr Lys Val Gly Arg Tyr Cys Ser Ile
                85                  90                  95

Ser Asp Gly Val Ser Met Phe Asn Phe Gln His Pro Met Asp Arg Ile
            100                 105                 110

Ser Thr Ala Ser Phe Thr Tyr Glu Thr Asn His Ser Phe Ile Asn Asp
        115                 120                 125

Ala Cys Gln Asn His Ile Asn Lys Thr Phe Pro Ile Val Asn His Asn
    130                 135                 140

Pro Ser Ser Ser Ile Thr His Leu Ile Ile Gln Asp Val Trp Ile
145                 150                 155                 160

Gly Lys Asp Val Leu Leu Lys Gln Gly Ile Thr Leu Gly Thr Gly Cys
                165                 170                 175

Val Ile Gly Gln Arg Ala Val Val Thr Lys Asp Val Pro Pro Tyr Ala
            180                 185                 190

Ile Val Ala Gly Ile Pro Ala Lys Ile Ile Lys Tyr Arg Phe Asp Glu
        195                 200                 205

Lys Thr Ile Glu Arg Leu Leu Lys Ile Gln Trp Trp Lys Tyr His Phe
    210                 215                 220
```

```
Ala Asp Phe Tyr Asp Ile Asp Leu Asn Leu Lys Ile Asn Gln Tyr Leu
225                 230                 235                 240

Asp Leu Leu Glu Glu Lys Ile Ile Lys Lys Ser Ile Ser Tyr Tyr Asn
                245                 250                 255

Pro Asn Lys Leu Tyr Phe Arg Asp Ile Leu Glu Leu Lys Ser Lys Lys
            260                 265                 270

Ile Phe Asn Leu Phe
        275

<210> SEQ ID NO 39
<211> LENGTH: 270
<212> TYPE: PRT
<213> ORGANISM: Campylobacter jejuni
<220> FEATURE:
<223> OTHER INFORMATION: glycosyltransferase from C. jejuni OH4384 (ORF
      12a of lipooligosaccharide (LOS) biosynthesis locus)

<400> SEQUENCE: 39

Met Pro Gln Leu Ser Ile Ile Pro Leu Phe Asn Ser Cys Asp Phe
 1               5                  10                  15

Ile Ser Arg Ala Leu Gln Ser Cys Ile Asn Gln Thr Leu Lys Asp Ile
                20                  25                  30

Glu Ile Leu Ile Ile Asp Asp Lys Ser Lys Asp Asn Ser Leu Asn Met
            35                  40                  45

Val Leu Glu Phe Ala Lys Lys Asp Pro Arg Ile Lys Ile Phe Gln Asn
    50                  55                  60

Glu Glu Asn Leu Gly Thr Phe Ala Ser Arg Asn Leu Gly Val Leu His
65                  70                  75                  80

Ser Ser Ser Asp Phe Ile Met Phe Leu Asp Ser Asp Asp Phe Leu Thr
                85                  90                  95

Pro Asp Ala Cys Glu Ile Ala Phe Lys Glu Met Lys Lys Gly Phe Asp
            100                 105                 110

Leu Leu Cys Phe Asp Ala Phe Val His Arg Val Lys Thr Lys Gln Phe
        115                 120                 125

Tyr Arg Phe Lys Gln Asp Glu Val Phe Asn Gln Lys Glu Phe Leu Glu
130                 135                 140

Phe Leu Ser Lys Gln Arg His Phe Cys Trp Ser Val Trp Ala Lys Cys
145                 150                 155                 160

Phe Lys Lys Asp Ile Ile Leu Lys Ser Phe Glu Lys Ile Lys Ile Asp
                165                 170                 175

Glu Arg Leu Asn Tyr Gly Glu Asp Val Leu Phe Cys Tyr Ile Tyr Phe
            180                 185                 190

Met Phe Cys Glu Lys Ile Ala Val Phe Lys Thr Cys Ile Tyr His Tyr
        195                 200                 205

Glu Phe Asn Pro Asn Gly Arg Tyr Glu Asn Lys Asn Lys Glu Ile Leu
    210                 215                 220

Asn Gln Asn Tyr His Asp Lys Lys Ser Asn Glu Ile Ile Lys Lys
225                 230                 235                 240

Leu Ser Lys Glu Phe Ala His Asp Glu Phe His Gln Lys Leu Phe Glu
                245                 250                 255

Val Leu Lys Arg Glu Glu Ala Gly Val Lys Asn Arg Leu Lys
            260                 265                 270

<210> SEQ ID NO 40
<211> LENGTH: 25
<212> TYPE: DNA
<213> ORGANISM: Artificial Sequence
```

```
<220> FEATURE:
<223> OTHER INFORMATION: Description of Artificial Sequence:CJ42 primer
      in heptosyltransferase-II used to amplify LPS core
      biosynthesis locus

<400> SEQUENCE: 40
gccattaccg tatcgcctaa ccagg                                              25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence:CJ43 primer
      in heptosyltransferase-I used to amplify LPS core
      biosynthesis locus

<400> SEQUENCE: 41
aaagaatacg aatttgctaa agagg                                              25

<210> SEQ ID NO 42
<211> LENGTH: 41
<212> TYPE: DNA
<213> ORGANISM: Artificial Sequence
<220> FEATURE:
<223> OTHER INFORMATION: Description of Artificial Sequence:CJ-106 3'
      primer used to amplify and clone ORF 5a

<400> SEQUENCE: 42
cctaggtcga cttaaaacaa tgttaagaat atttttttta g                            41

<210> SEQ ID NO 43
<211> LENGTH: 37
<212> TYPE: DNA
<213> ORGANISM: Artificial Sequence
<220> FEATURE:
<223> OTHER INFORMATION: Description of Artificial Sequence:CJ-157 5'
      primer used to amplify and clone ORF 5a

<400> SEQUENCE: 43
cttaggaggt catatgctat ttcaatcata ctttgtg                                 37

<210> SEQ ID NO 44
<211> LENGTH: 37
<212> TYPE: DNA
<213> ORGANISM: Artificial Sequence
<220> FEATURE:
<223> OTHER INFORMATION: Description of Artificial Sequence:CJ-105 3'
      primer used to amplify  and clone ORF 6a

<400> SEQUENCE: 44
cctaggtcga cctctaaaaa aaatattctt aacattg                                 37

<210> SEQ ID NO 45
<211> LENGTH: 39
<212> TYPE: DNA
<213> ORGANISM: Artificial Sequence
<220> FEATURE:
<223> OTHER INFORMATION: Description of Artificial Sequence:CJ-133 5'
      primer used to amplify and clone ORF 6a

<400> SEQUENCE: 45
cttaggaggt catatgttta aaatttcaat catcttacc                               39

<210> SEQ ID NO 46
<211> LENGTH: 41
<212> TYPE: DNA
```

-continued

<213> ORGANISM: Artificial Sequence
<220> FEATURE:
<223> OTHER INFORMATION: Description of Artificial Sequence:CJ-131 5'
    primer used to amplify and clone ORF 7a

<400> SEQUENCE: 46
cttaggaggt catatgaaaa aagttattat tgctggaaat g                          41

<210> SEQ ID NO 47
<211> LENGTH: 41
<212> TYPE: DNA
<213> ORGANISM: Artificial Sequence
<220> FEATURE:
<223> OTHER INFORMATION: Description of Artificial Sequence:CJ-132 3'
    primer used to amplify and clone ORF 7a

<400> SEQUENCE: 47
cctaggtcga cttattttcc tttgaaataa tgctttatat c                          41

<210> SEQ ID NO 48
<211> LENGTH: 322
<212> TYPE: PRT
<213> ORGANISM: Campylobacter jejuni
<220> FEATURE:
<223> OTHER INFORMATION: Campylobacter alpha-2,3-sialyltransferase I
    (Cst-I) from C. jejuni OH4384

<400> SEQUENCE: 48

Met Thr Arg Thr Arg Met Glu Asn Glu Leu Ile Val Ser Lys Asn Met
 1               5                  10                  15

Gln Asn Ile Ile Ile Ala Gly Asn Gly Pro Ser Leu Lys Asn Ile Asn
            20                  25                  30

Tyr Lys Arg Leu Pro Arg Glu Tyr Asp Val Phe Arg Cys Asn Gln Phe
        35                  40                  45

Tyr Phe Glu Asp Lys Tyr Tyr Leu Gly Lys Lys Ile Lys Ala Val Phe
    50                  55                  60

Phe Asn Pro Gly Val Phe Leu Gln Gln Tyr His Thr Ala Lys Gln Leu
65                  70                  75                  80

Ile Leu Lys Asn Glu Tyr Glu Ile Lys Asn Ile Phe Cys Ser Thr Phe
                85                  90                  95

Asn Leu Pro Phe Ile Glu Ser Asn Asp Phe Leu His Gln Phe Tyr Asn
            100                 105                 110

Phe Phe Pro Asp Ala Lys Leu Gly Tyr Glu Val Ile Glu Asn Leu Lys
        115                 120                 125

Glu Phe Tyr Ala Tyr Ile Lys Tyr Asn Glu Ile Tyr Phe Asn Lys Arg
    130                 135                 140

Ile Thr Ser Gly Val Tyr Met Cys Ala Ile Ala Ile Ala Leu Gly Tyr
145                 150                 155                 160

Lys Thr Ile Tyr Leu Cys Gly Ile Asp Phe Tyr Glu Gly Asp Val Ile
                165                 170                 175

Tyr Pro Phe Glu Ala Met Ser Thr Asn Ile Lys Thr Ile Phe Pro Gly
            180                 185                 190

Ile Lys Asp Phe Lys Pro Ser Asn Cys His Ser Lys Glu Tyr Asp Ile
        195                 200                 205

Glu Ala Leu Lys Leu Leu Lys Ser Ile Tyr Lys Val Asn Ile Tyr Ala
    210                 215                 220

Leu Cys Asp Asp Ser Ile Leu Ala Asn His Phe Pro Leu Ser Ile Asn
225                 230                 235                 240

Ile Asn Asn Asn Phe Thr Leu Glu Asn Lys His Asn Asn Ser Ile Asn

-continued

```
                245                 250                 255
Asp Ile Leu Leu Thr Asp Asn Thr Pro Gly Val Ser Phe Tyr Lys Asn
                260                 265                 270

Gln Leu Lys Ala Asp Asn Lys Ile Met Leu Asn Phe Tyr Asn Ile Leu
                275                 280                 285

His Ser Lys Asp Asn Leu Ile Lys Phe Leu Asn Lys Glu Ile Ala Val
                290                 295                 300

Leu Lys Lys Gln Thr Thr Gln Arg Ala Lys Ala Arg Ile Gln Asn His
305                 310                 315                 320

Leu Ser
```

<210> SEQ ID NO 49
<211> LENGTH: 231
<212> TYPE: PRT
<213> ORGANISM: Haemophilus influenzae
<220> FEATURE:
<223> OTHER INFORMATION: putative ORF from GenBank #U32720

<400> SEQUENCE: 49

```
Met Gln Leu Ile Lys Asn Asn Glu Tyr Glu Tyr Ala Asp Ile Ile Leu
1               5                   10                  15

Ser Ser Phe Val Asn Leu Gly Asp Ser Glu Leu Lys Lys Ile Lys Asn
                20                  25                  30

Val Gln Lys Leu Leu Thr Gln Val Asp Ile Gly His Tyr Tyr Leu Asn
                35                  40                  45

Lys Leu Pro Ala Phe Asp Ala Tyr Leu Gln Tyr Asn Glu Leu Tyr Glu
            50                  55                  60

Asn Lys Arg Ile Thr Ser Gly Val Tyr Met Cys Ala Val Ala Thr Val
65                  70                  75                  80

Met Gly Tyr Lys Asp Leu Tyr Leu Thr Gly Ile Asp Phe Tyr Gln Glu
                85                  90                  95

Lys Gly Asn Pro Tyr Ala Phe His His Gln Lys Glu Asn Ile Ile Lys
                100                 105                 110

Leu Leu Pro Ser Phe Ser Gln Asn Lys Ser Gln Ser Asp Ile His Ser
            115                 120                 125

Met Glu Tyr Asp Leu Asn Ala Leu Tyr Phe Leu Gln Lys His Tyr Gly
        130                 135                 140

Val Asn Ile Tyr Cys Ile Ser Pro Glu Ser Pro Leu Cys Asn Tyr Phe
145                 150                 155                 160

Pro Leu Ser Pro Leu Asn Asn Pro Ile Thr Phe Ile Leu Glu Glu Lys
                165                 170                 175

Lys Asn Tyr Thr Gln Asp Ile Leu Ile Pro Lys Phe Val Tyr Lys
                180                 185                 190

Lys Ile Gly Ile Tyr Ser Lys Pro Arg Ile Tyr Gln Asn Leu Ile Phe
            195                 200                 205

Arg Leu Ile Trp Asp Ile Leu Arg Leu Pro Asn Asp Ile Lys His Ala
        210                 215                 220

Leu Lys Ser Arg Lys Trp Asp
225                 230
```